(12) United States Patent
Emalfrab et al.

(10) Patent No.: US 6,573,086 B1
(45) Date of Patent: Jun. 3, 2003

(54) TRANSFORMATION SYSTEM IN THE FIELD OF FILAMENTOUS FUNGAL HOSTS

(75) Inventors: Mark Aaron Emalfrab, Jupiter, FL (US); Richard Paul Burlingame, Manitowoc, WI (US); Philip Terry Olson, Manitowoc, WI (US); Arkady Panteleimonovich Sinitsyn, Moscow (RU); Martine Parriche, Toulouse (FR); Jean Christophe Bousson, Quint-Fonsegrives (FR); Christine Marie Pynnonen, Manitowoc, WI (US); Peter Jan Punt, Houten (NL); Cornelia Marie Johanna Van Zeijl, Vieuten-De Meern (NL)

(73) Assignee: Dyadic International, Inc., Jupiter, FL (US)

( * ) Notice: Subject to any disclaimer, the term of this patent is extended or adjusted under 35 U.S.C. 154(b) by 0 days.

(21) Appl. No.: 09/548,938

(22) Filed: Apr. 13, 2000

Related U.S. Application Data

(63) Continuation-in-part of application No. PCT/NL99/00618, filed on Oct. 6, 1999, which is a continuation-in-part of application No. PCT/EP98/06496, filed on Oct. 6, 1998.

(51) Int. Cl.$^7$ .................................................. C12N 1/15
(52) U.S. Cl. ................................. 435/254.11; 435/69.1; 435/209
(58) Field of Search ........................... 435/254.11, 69.1, 435/209

(56) References Cited

U.S. PATENT DOCUMENTS 5,763,254 A    6/1998   Wöldike et al.

FOREIGN PATENT DOCUMENTS

| WO | WO 97/13853 | 4/1997 |
| WO | WO 97/27363 | 7/1997 |
| WO | WO 98/15633 | 4/1998 |
| WO | WO 00/20555 | 4/2000 |

OTHER PUBLICATIONS

Iikura Hiroshi, et al: "Cloning of a Gene Encoding a Putative Xylanase with a Cellulose–Binding Domain from *Humicola Grisea*", Bioscience Biotechnology And Biochemistry, 61, No. 9, 1997, pp. 1593–1595.

Gunf–Fusox, accession No. p46239, Nov. 1, 1995, P.O. Sheppard, et al.: "The Use of Conserved Cellulase Family–Specific Sequences to Clone Cellulase Homologue cDNAs from Fusarium Oxysporum."

Accession No. o59937, Aug. 1, 1998, M.C. Ruiz–Roldan et al.: "Fusarium Oxysporum f.s.p. lycopersici. family F xylanase (XYL3).

Accession No. D63515; Aug. 21, 1995, S. Takishima et al.: "Cloning, Sequencing, and Eepression of the Cellulase Genes of Humicola Grisea Var. Thermoida."

P. O. Sheppard, et al:, Gene: 150, 1994, pp. 163–167.

Accession No. Q12621, Nov. 1, 1996, S. Takishima et al.: "Cloning, Sequencing, And Expression of the Cellulase Genes of Humicola Grisea Var. Thermoidea".

K. Eriksson, et. al.: "Extracellular Enzyme System Utilized by the Fungus *Sporotrichum Pulverulentum* (*Chrysosporium Lignorum*) for the Breakdown of Cellulose." 1, Separation, Purification And Physico–Chemical Characterisation of Five Endo–1, 4–Beta–Glucanases *European Journal of Biochemistry*, 51, 1975, pp. 193–206.

Communication, dated Dec. 28, 2000, European Search Report.

*Primary Examiner*—James Ketter
(74) *Attorney, Agent, or Firm*—Morgan & Finnegan, LLP

(57) ABSTRACT

A novel transformation system in the field of filamentous fungal hosts for expressing and secreting heterologous proteins or polypeptides is described. The invention also covers a process for producing large amounts of polypeptide or protein in an economical manner. The system comprises a transformed or transfected fungal strain of the genus Chrysosporium, more particularly of *Chrysosporium lucknowense* and mutants or derivatives thereof. It also covers transformants containing Chrysosporium coding sequences, as well expression-regulating sequences of Chrysosporium genes. Also provided are novel fungal enzymes and their encoding sequences and expression-regulating sequences.

25 Claims, 36 Drawing Sheets

Fig. 13a
45kD endo (pI 6.0)
Fig. 13b
55 kD endo (pI 4.9)
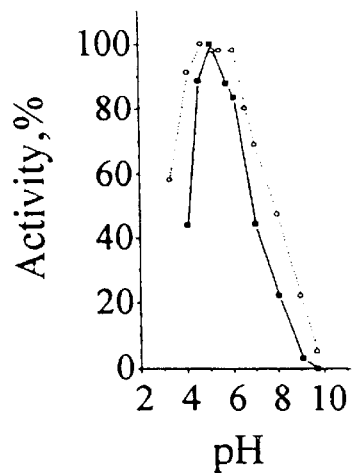
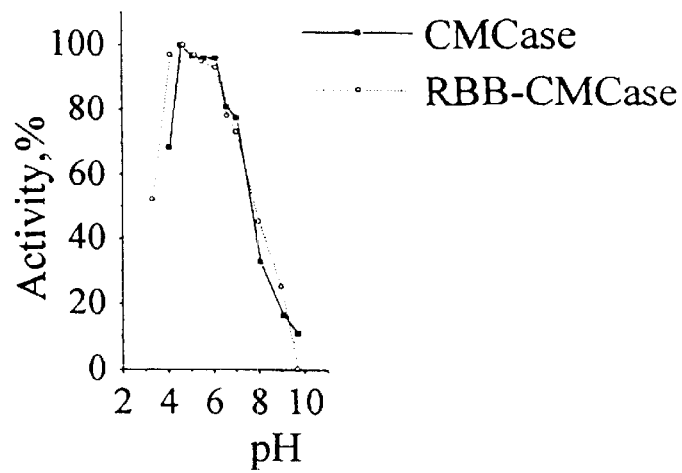
Fig. 13c
30kD Xyl (pI 9.1)
Fig. 13d
51kD Xyl (pI 8.7)
Fig. 13e
60 kD Xyl (pI 4.7)
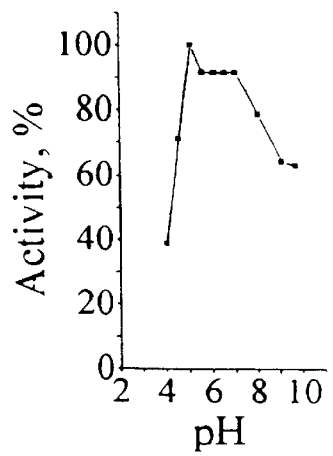
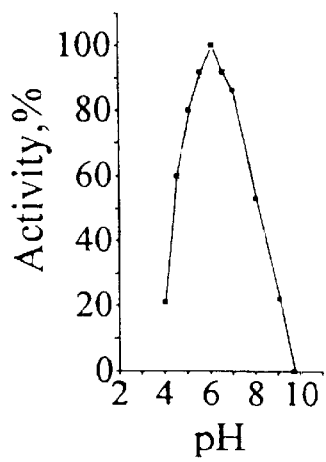
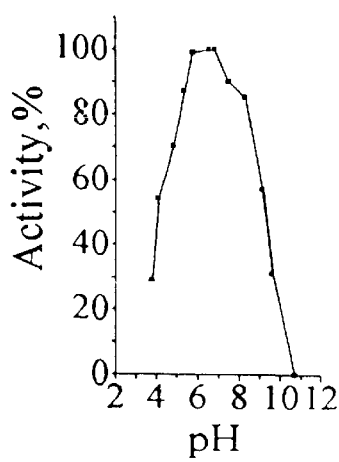
— Xylanase 45 kD Endo (pI 6.0)

55 kD Endo (pI 4.9)

30 kD Xyl (pI 9.1)

51 kD Xyl (pI 8.7)

Fig. 16a
45 kD endo (pI 6.0)
Fig. 16b
55kD endo (pI 4.9)
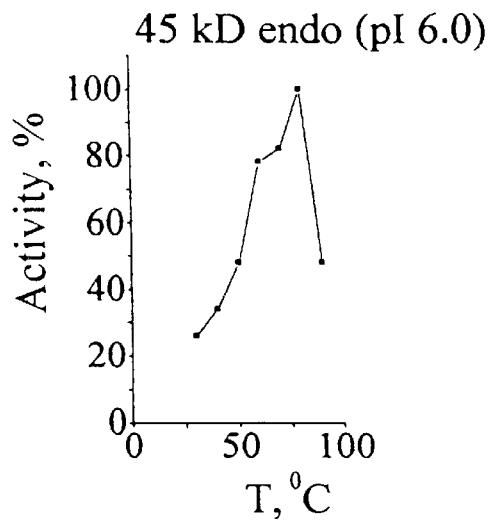
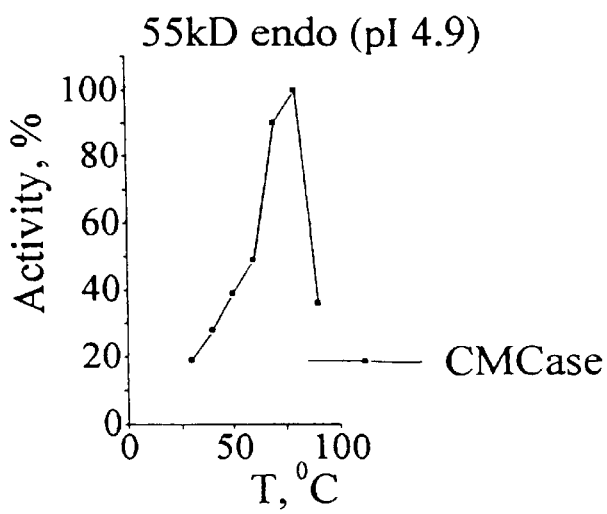
Fig. 16c
30 kD Xyl (pI 9.1)
Fig. 16d
51 kD Xyl (pI 8.7)
Fig. 16e
60 kD Xyl (pI 4.7)
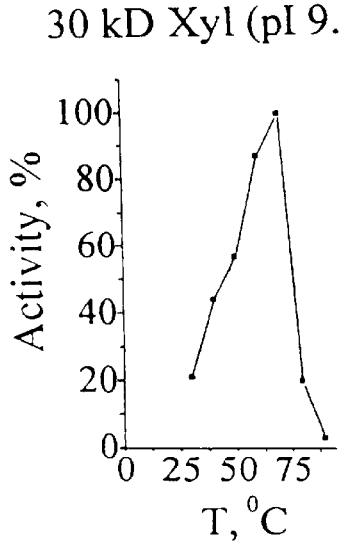
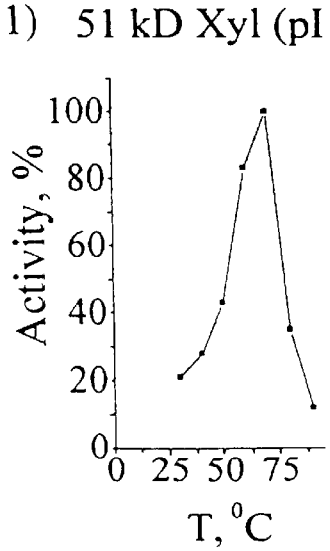
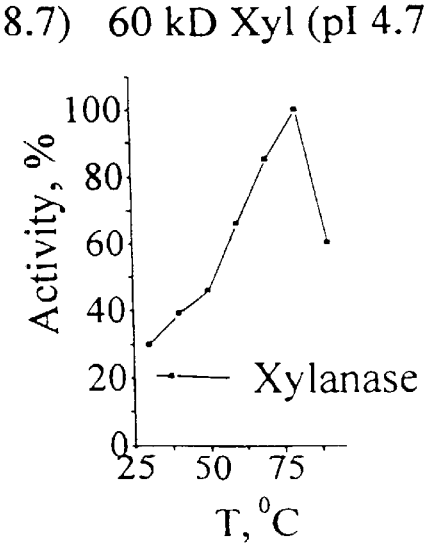

SEQUENCE LISTING

<160> NUMBER OF SEQ ID NOS: 19

<210> SEQ ID NO 1
<211> LENGTH: 4451
<212> TYPE: DNA
<213> ORGANISM: Chrysosporium lucknowense
<220> FEATURE:
<221> NAME/KEY: modified_base
<222> LOCATION: (2941)
<223> OTHER INFORMATION: a, t, c, g, other or unknown

<400> SEQUENCE: 1

```
aaggtatccg atttggggaa cgtcgatgaa agtattgcaa aagtgacgag agttgcgcaa    60
ctaactcgct gccgaagaag ctgcggaaga aagagaacac cgaaagtgga ataacgttac   120
ggatgtcctg acctcaaagt tgaaaccagc ccttcctgct ctatttggga aagcggcttg   180
cccttgaatg cgctgcactg tggcacgact accagtgatc gggaggagca aactaccctg   240
gtccgttcct tggtggggcg gcactaggcc caacttaggg tgatcggagg tcgatgccgc   300
ggtcctcgtt ggtctgggct cttctcattt cccggtttgc acccccgtt gcacctgctg    360
atcgcccgcc aacgccgatg aggttgcgcc cagaccgaca atcaccgcgg ctgcattccc   420
aagtatattg aagatggcac caggtacccg gttttgcgtc ccagtcgttt ggtgccaaat   480
ttgggagttt ttgagcctca agatctgggg aaatcgacct caacttccat acaagttaaa   540
gtcgcacaca cggcgagttc cacgaagaga cacatttttt tctgaaggcc tctctccccg   600
cacatcagaa accaccaaat accaagactg cagaagccgg ggtaagtggg ccaccgggac   660
tacactaaaa tgcggggaga agcgagatcc gttgcgaagg gaagggatgg ggtgtgctgc   720
ggctttctcc gctctcgtgc gcctttgct tgaatctagt gtacaccagg gtaggctccg    780
```

```
aaggagtatc tacggcagcg ctgttcgtgc tgcgttgaga gtcagggcgg agacgagcag    840
gcgacaggag cctcgcaccg gcacttcgga tcgcatttgc gcggagcgtc aaatacgctc    900
ttctgcggtc atcagagagc atcgtgaacc aaggttcttc cgcagggcgg cctgggcttc    960
gcagagtcgc actcggcgga cgccttccgt gtcacccctg ataacctggc tgccgcgccc   1020
agactcctcc aatgaggtgt gtggttgccc tcgccgaccc ttcagcaacc ttaatcgctt   1080
ccatcgcacg gctccacgtc ctcgaacgat gccctcagtc cgtgcccggc cgtggcaacc   1140
ataacgtgac atcgccgccc agcctactag ccgctatcga ccggttaggc ttgtcaccgc   1200
agcgcccatt ctccatcggg cctctactct gatccacctc acccaccgca agcactagcg   1260
agcctcacca gagtgcaagc gacacgaccc gcttggccct tcgtccttga ctatctccca   1320
gacctcttgc catcttgccg acgccgcccc cttttttttc tcctcccct gccggcaggt    1380 cggtggcccc agtcccgaga tggcattgct ccgttgtcca tgacgaccca tcattcgatg   1440
gctgactggc acactcgtct tgtttgagca tcgacggccc gcggcccgtc tcccacggta   1500
cggaacctcg ttgtacagta cctctcgtaa tgatacccaa caccggggcc gagcgctggg   1560
agggcggcgt tcccgagaag ccgggaaggc ggctggccgg ctgacctttg tgacttggcg   1620
atggatgcgc ccatggagaa tgtccgtccg aagcgacgcg acaattagcc tggctaccat   1680
cgatataaat tgggtgattc ccagctcttg atgggcgtgt cttctgcctg gcagccctcg   1740
tcttcagatc aagcaactgt gtgctgatcc tcttccgcca tgtacgccaa gttcgcgacc   1800
ctcgccgccc ttgtggctgg cgccgctgct cagaacgcct gcactctgac cgctgagaac   1860 caccccctcgc tgacgtggtc caagtgcacg tctggcggca gctgcaccag cgtccagggt   1920
tccatcacca tcgacgccaa ctggcggtgg actcaccgga ccgatagcgc caccaactgc   1980
tacgagggca acaagtggga tacttcgtac tgcagcgatg gtccttcttg cgcctccaag   2040
tgctgcatcg acggcgctga ctactcgagc acctatggca tcaccacgag cggtaactcc   2100
ctgaacctca gttcgtcac caagggccag tactcgacca acatcggctc gcgtacctac   2160
ctgatggaga gcgacaccaa gtaccagagt aagttcctct cgcacccggc cgccgggaga   2220
tgatggcgcc cagcccgctg acgcgaatga cacagtgttc cagctcctcg gcaacgagtt   2280
caccttcgat gtcgacgtct ccaacctcgg ctgcggcctc aatggcgccc tctacttcgt   2340
gtccatggat gccgatggtg gcatgtccaa gtactcgggc aacaaggcag gtgccaagta   2400
cggtaccggc tactgtgatt ctcagtgccc ccgcgaccctc aagttcatca acggcgaggc   2460
caacgtagag aactggcaga gctcgaccaa cgatgccaac gccggcacgg gcaagtacgg   2520
cagctgctgc tccgagatgg acgtctggga ggccaacaac atggccgccg ccttcactcc   2580
ccacccttgc accgtgatcg gccagtcgcg ctgcgagggc gactcgtgcg gcggtaccta   2640
cagcaccgac cgctatgccg gcatctgcga ccccgacgga tgcgacttca actcgtaccg   2700
ccagggcaac aagaccttct acggcaaggg catgacggtc gacacgacca agaagatcac   2760
ggtcgtcacc cagttcctca agaactcggc ggcgagctc tccgagatca gcggttcta   2820 cgtccagaac ggcaaggtca tccccaactc cgagtccacc atcccgggcg tcgagggcaa   2880
ctccatcacc caggactggt gcgaccgcca gaaggccgcc ttcggcgacg tgaccgactt   2940
ncaggacaag gcggcatgg tccagatggg caaggccctc gcggggccca tggtcctcgt   3000
catgtccatc tgggacgacc acgccgtcaa catgctctgg ctcgactcca cctggcccat   3060
cgacggcgcc ggcaagccgg gcgccgagcg cggtgcctgc cccaccacct cgggcgtccc   3120
```

-continued

```
cgctgaggtc gaggccgagg cccccaactc caacgtcatc ttctccaaca tccgcttcgg   3180
ccccatcggc tccaccgtct ccggcctgcc cgacggcggc agcggcaacc ccaacccgcc   3240
cgtcagctcg tccaccccgg tcccctcctc gtccaccaca tcctccggtt cctccggccc   3300
gactggcggc acgggtgtcg ctaagcacta tgagcaatgc ggaggaatcg ggttcactgg   3360
ccctacccag tgcgagagcc cctacacttg caccaagctg aatgactggt actcgcagtg   3420
cctgtaaacg aacctctctg aaggaggttc tgagacacgc gcgattcttc tgtatatagt   3480
tttatttttc actctggagt gcttcgctcc accagtacat aaacctttt tttcacgtaa    3540 caaaatggct tcttttcaga ccatgtgaac catcttgatg ccttgacctc ttcagttctc   3600
actttaacgt agttcgcgtt agtctgtatg tcccagttgc atgtagttga gataaatacc   3660
cctggaagtg ggtctgggcc tttgtgggac ggagccctct ttctgtggtc tggagagccc   3720
gctctctacc gcctaccttc ttaccacagt acactactca cacattgctg aactgaccca   3780
tcataccgta ctttatcctg ttaattcgtg gtgctgtcga ctattctatt tgctcaaatg   3840
gagagcacat tcatcggcgc agggatacac ggtttatgga ccccaagagt gtaaggacta   3900
ttattagtaa tattatatgc ctctaggcgc cttaacttca acaggcgagc actactaatc   3960
aacttttggt agaccccaatt acaaacgacc atacgtgccg gaaattttgg gattccgtcc   4020
gctctcccca accaagctag aagaggcaac gaacagccaa tcccggtgct aattaaatta   4080
tatggttcat ttttttttaaa aaattttttt cttcccattt tcctctcgct tttcttttc    4140 gcatcgtagt tgatcaaagt ccaagtcaag cgagctattt gtgctatagc tcggtggcta   4200
taatcagtac agcttagaga ggctgtaaag gtatgatacc acagcagtat tcgcgctata   4260
agcggcactc ctagactaat tgttacggtc tacagaagta ggtaataaaa gcgttaattg   4320
ttctaaatac tagaggcact tagagaagct atctaaatat atattgaccc tagcttatta   4380
tccctattag taagttagtt agctctaacc tatagatagc caaatgctat aataggtacc   4440
agggttcaaa a                                                       4451
```

<210> SEQ ID NO 2
<211> LENGTH: 3028
<212> TYPE: DNA
<213> ORGANISM: Chrysosporium lucknowense
<220> FEATURE:
<221> NAME/KEY: modified_base
<222> LOCATION: (46)..(47)
<223> OTHER INFORMATION: a, t, c, g, other or unknown
<220> FEATURE:
<221> NAME/KEY: modified_base
<222> LOCATION: (374)
<223> OTHER INFORMATION: a, t, c, g, other or unknown

<400> SEQUENCE: 2

```
tcatcaactt ggcgtttgga tgtactaata ttacacgtcg tttgcnnagc ggagtctgtg     60
tcatctccgt ggggtcgggt gctccagacg acgcttcggg ccgatcctga attcgggaag   120
gaaacggttc ggctaatcag gtcctctaaa atataacgaa gcactacaga gggagttcct   180
cagaggacat cgtatcaacc gaagaacgaa gcgccgaaag gactgatcaa acaggagta    240 ggtagggatg tgtgagtacc taaactttcc ataccctgaca taaaatcatc atggtgcttc   300
agacctgttt gatgaggcga gggcggaggc cgcattgtat tttcgttcct ccttcttttt   360
tgttagtata tctnagggtt ccatcgtaaa atggaatctt ccagctctac tagtaattag   420
aacaatagtt ctgatgtcgt gcgccaagct tttcagatg actgccaaaa acccatcatg    480
ggtatggaca aaagcagtaa tcggagtcac aacgccgcat tttccttcat gatttccgtc   540
```

```
aaccggagag gtcggaggag gactccggcc acatgtgatg cgaagaagta catggcgcca    600
tggttctaac ctcttatagt ctgaaaatgc gcggaggcca gcgaagccaa gcccgggaac    660
cgttcttgtc atggtttcag tattgtttcg ctaaacattc tatccgattc gcgataggtg    720
cggctgccac cgaaggttgt atccttaaag ctttggtaag tacggagtac ggaaatggaa    780
acgcgccgca gtcctggttc catcggtatc ctccgcatgc tccgccaaaa aaagaaaacc    840
cgggtatgtt tacaaaggat ataagagaca agatgcacca cccgccccct tcccatctgc    900
cggttgccca cgtcgccgtc gactgcttgt ccgcttccta cctgcagcct cttttcagaga   960
ccatcaaaca tgcgtactct tacgttcgtg ctggcagccg ccccggtggc tgtgcttgcc   1020
caatctcctc tgtggggcca gtgtatgtaa ttgccttact cggaaaatag tcaccactag   1080
agggacttaa gctcactact tcctgtttca aataggcgg cggtcaaggc tggacaggtc    1140
ccacgacctg cgtttctggc gcagtatgcc aattcgtcaa gtcagtaact gcttttattt   1200
cttttctctc tgggattacg atttcgtttt gcacttagct tggttctgca tttcattgtt   1260
gtattgttct cttttgtgt gtgagaggtt ttattaccac ctaaaggcca tttgctaaca    1320
aatctcccca gtgactggta ctcccaatgc gtgcccggat cgagcaaccc tcctacgggc   1380
accaccagca gcaccactgg aagcaccccg gctcctactg gcggcggcgg cagcggaacc   1440
ggcctccacg acaaattcaa ggccaagggc aagctctact tcggaaccga gatcgatcac   1500
taccatctca acaacaatgc cttgaccaac attgtcaaga agactttggg tcaagtcact   1560
cacgagaaca gcttgaagtg ggatgctact gagcgtgagt gacctctcct ccttctcccg   1620
acaataatag ataattacga gccggttcga ggctgacatt gcgcgattct agcgagccgc   1680
aatcaattca actttgccaa cgccgacgcg gttgtcaact ttgcccaggc caacggcaag   1740
ctcatccgcg gccacaccct cctctggcac tctcagctgc cgcagtgggt gcagaacatc   1800
aacgaccgca acaccttgac ccaggtcatc gagaaccacg tcaccaccct tgtcactcgc   1860
tacaagggca agatcctcca ctgggacgtc gttaacgaga tctttgccga ggacggctcg   1920
ctccgcgaca gcgtcttcag ccgcgtcctc ggcgaggact ttgtcggcat cgccttccgc   1980
gccgccgcg ccgccgatcc caacgccaag ctctacatca acgactacaa cctcgacatt    2040
gccaactacg ccaaggtgac ccggggcatg gtcgagaagg tcaacaagtg gatcgcccag   2100
ggcatcccga tcgacggcat cggcacccag tgccacctgg ccgggcccgg cgggtggaac   2160
acggccgccg gcgtccccga cgccctcaag gccctcgccg cggccaacgt caaggagatc   2220
gccatcaccg agctcgacat cgccggcgcc tccgccaacg actacctcac cgtcatgaac   2280
gcctgcctcc aggtctccaa gtgcgtcggc atcaccgtct gggcgtctc tgacaaggac    2340
agctggaggt cgagcagcaa cccgctcctc ttcgacagca actaccagcc aaaggcggca   2400
tacaatgctc tgattaatgc cttgtaagag gaggtatatt atttttagag gcaatgaagc   2460
taggaggaaa gagggaagt gaggtaatta gctaggacag gcaaatctag cagcaattat    2520
aagtcaacac tatataaaat attcctataa tggcttgtgc ttcggtgtgc aaaaaaaaaa   2580
aaaaaaaaaa aaaaaaaaa aaaaaaaac tcaaaacaa aatgatcca acatgattcg       2640
aaatggcgac cttgcaaatg cacacctcag ataataccac tatacaatac accttaaatg   2700
gcacctaaat ccatttgtct gcggtcatag acggggctta agaagcctgg gatgcaggtg   2760
tcgatgcaag ggtacgtcga gtgtatgata tgagtatgaa ccatgctgtc tgggtaattc   2820
tccactttcc ctcccttac gactcttcgg gtgtgcctct ctagaaagtc gactcctggc    2880
```

```
gcctcagatc gcccttggc tctgttcggt acaatgacgt ccgctggttt cttccaaaga    2940
ccaggtattt ctcccgtggc aacaaagaat accaaatacc tatatcgaac cgtagtcttc    3000
tgataattag atgtctctca aggcgcgg                                        3028

<210> SEQ ID NO 3
<211> LENGTH: 3036
<212> TYPE: DNA
<213> ORGANISM: Chrysosporium lucknowense

<400> SEQUENCE: 3
ccgccctgga gcgtggaccg tggggacagg cggcaaatga gaccctattg gggcgcatcg      60
acggtgcaga accgaggttc cgggaccttg cagagcggc ccagggaccc cgccatccag     120
ctatgcgcct ccacagaagc cgaccgatgc tcgggttgca tcccgagatc gtcggtatta     180
aggagagggg agaagaagaa gggggggggg gggggggaat gagacaacaa cactcaggcg     240
cgccaattag aacttcaacg agcctccttc ctgcatccag acaagaccga ggtcgagccg     300
ggtactatgc aagcgtcccg tgccgcgtga tgtcgctcgt aggtgttgac aggttctcag     360
ctgtttcttg aatccccggg aggtggacta aaggggcaag agaccatggt aagctccgtc     420
gccagccctc ccgttgcgga gcggaagccg aggaccgacc ttcttctgga gaacccgggc     480
tgcccgggcg gaggcgggtt ccgccttttt tttaaccagt ccgagttgtt gtcgcgaact     540
gcgctcggtt gcaacgtcag tgtccaatcg gcaggcgtat cgcgacccgg taaggggggtt     600 acggcatgtg ttctcggctt ccgcacatca aaacttactc gtattcgtcc tgaccttggt     660
aattaattat gtcgcaagac aaggagttgt ttgagacgac tccggcgcgc ataattacac     720
agtggtgcag tattatatat ctttctcccg tagggacgac gacaaagacc cgtcagtgat     780
taataataat tagtagcagt ttctttcttt caagactcaa gaatactcct ttccgccatc     840
gtggcagcgt ttagattcat catgcagccg tttctgctct tgttcctctc gtcggtcacg     900
gcggcgagcc ccctgacggc gctcgacaag cggcagcagg cgacgttgtg cgagcagtac     960
ggctactggt cggcaacgg ttacgaggtc aacaacaaca actggggcaa ggattcggcc    1020
tcgggcggcc atcagtgcac ctacgtcgac agcagcagct ccagcggcgt cgcctggcac    1080
acgacctggc agtgggaagg aggccagaac caggtcaaga gcttcgccaa ctgcggcctg    1140
caggtgccca agggcaggac catctcgtcc atcagcaacc tgcagacctc catctcgtgg    1200
tcctacagca caccaacat ccgcgccaac gtggcctacg acctcttcac cgcggcagac    1260
ccgaaccacg cgaccagcag cggcgactac gagctcatga tctggtcagt ttttttttc    1320 tttttcttt tcttctcttt tcttttcttt tcctttctcc tgttttattt tcttatccat    1380
tgcttcgccc tctttcctta accctgctga ctctctcttc ttgtcaatga tactgtaata    1440
ggctggcgag attcggcgac gtctaccca tcggctcgtc ccaggccac gtcaacgtgg    1500 ccggccagga ctgggagctg tggacgggct tcaacggcaa catgcgggtc tacagcttcg    1560
tagcgcccag ccccgcaac agcttcagcg ccaacgtcaa ggacttcttc aactatctcc    1620
agtccaacca gggcttcccg ccagcagcc aataccttct cagtaaggag acgagatctc    1680
gaacagcata ccatatatgc gtgcggtaca agtgcactaa ccccctttt tttcccgttc    1740 gcagtcttcc aggcgggcac cgagcccttc accggcggcg agaccaccct taccgtcaac    1800
aactactctg caaggggttgc ttaaacagga aggccgagga tggcccccaa ggccgttgcg    1860
ggttcacgag ctctcttctt ttcaagtgct gtacatacat aattagcgta ccaagtcata    1920 gctgttttgtc agcttcaaac taagtgctcg cccacaaaag agggggagg ggaaaataac    1980
```

-continued

```
aaattgccga acgcagtgat aagcttctgg gagcgttgaa agcagtctac agtaggtggc    2040
tgyacgaagg aaaagagtgc cttattaaag ctatctacaa aggagacaaa acgactgata    2100
tttatggaca aagggactgg ccaatgcgtt aaacagcctc atacagctgt agcatatata    2160
tggctaatac gtttggaagc tctatagctt ccgacacacc ccctagttaa acgtagtagt    2220
cgtttaacta cgctttgygg tgatactgtt cttggtatta tatcctttgt cgctcttacc    2280
tcgatagctc cttcagggg cctgccttct gtattcggaa gtctaaaaga gtcgagtata    2340
gtagagcgat tcctttaaag ctatagatca aatatggcca ttataactat agtagtaata    2400
gtattactag tttaatcat aatagtaata ataggatgac gcctcttatg cttgaatcaa     2460
tagatgactc gttaggtcta cctattacaa acactataac tgctagtagg tcgactcctg    2520
ctcctataac acctcgtaag tataagtata ctaaagcttc tataccgtaa gtgttcctat    2580
tgtccctatt tgattaactt tattactagt tttgtagttt tcttagtagt tctagcgatt    2640
taagcgagtt tacgtggttc ggcttcttct ggttaatttg atagcgactc tatcacagtt    2700
tctagcgctt tactagtcac gtctagatcg tttaagctga ctaaatatag caacatcgaa    2760
gctagcgagc tttgtaaggt accctataga atatatatac ggtcggctct agtaggacgt    2820
tcttttagca aatgtcacga tcattccggc gttagctcct actattacta ttatacctat    2880
agttcctata agtgtaggga gatatacgtt aatcgcctat acgtctaata gctcttataa    2940
tacttatact aactataatg gtagtcttgc ttcttatatt aggtcggcta aggacttaac    3000
gaaggctcta atggatagag ctaaggcttc tataag                              3036
```

<210> SEQ ID NO 4
<211> LENGTH: 2547
<212> TYPE: DNA
<213> ORGANISM: Chrysosporium lucknowense

<400> SEQUENCE: 4

```
tgagcagcaa tgagcagcaa tgagcattcc tgggccaccg agtctgagtg ccagtacgga     60
gtatcgtact tcgtaccggg gtttgatttg gtgacggtgc ttttcacctc tcgatgcccg    120
aaatcgggtc taagctgagt ttgatcaaat atgtgactcc aacatcgccc ccttcggcaa    180 acccgtcga cacgtgtgtc atccttccat tgcaagcgat cactcgcagg gcgtgacgat     240
gaacgagatt tttgcccgga ccgattcgcg gatatagcgg cagccgacca gcccaccac     300 actgatggcc gtgtcactag tgtatgctcc cagaaccgca agcatacact gggcaatgct    360
tggtatgcag ttgaggcagc tttatgtttc catacccttc cacttcggct cggggactcg    420
gcggggtcgc ggaagtttga cggcagccgt cgggccttag gccagatta ccgtggttgt     480 ggcccagttt tagccgttcc cgtccgtttc ctaccggacc atgatttcg tgaaccattg     540 caatcccgaa gcgcatttcc gacgttaagg agttacctcc gctgcccaga attcatgatc    600
gtggccggct caaggcagcg tggcgggca tccgtgtcaa gctcccagga ggaggtgcgc     660
gatttcaaat ccgggccaaa acaggccaag actggctggc caaaaaaagg agcgtagacg    720
gcccgggaca tcggacgtca gctcgcagcc acccaaaacc ggtccgatct actcgcttac    780
tgtggtagtt caggtacttt tgagtagtaa aaacgctacg gcagggccgg ggggttcccc    840
ggtgacggag gtgcctctgc ggtggcgaac atcccacgca ctctcgagct acggtgacac    900
ctcgtgtcct gttggtcttg caatgctggg gcggcaggaa atgcgtcgcg ctcctcccgg    960
ccaagaccta aaacagacag cgccgcaaag tcgctcacta gcaccgcgaa acgaagatgc   1020
```

-continued

```
cccacctcaa cgcaatctgt gatgcaagca attgggaagg ctcaccccac ctcagcgagg      1080
ggctcaacca tttttattat cagctcatgc caccacaaca tgactgtttt cttttccttgc    1140 tcatcccaca tttgacaaaa atcgtcgatt aatctctttc catacaggcc gtccgcgctc     1200
tgataaccac ataaaagtct cttcagtcaa cagctcaaag ctccctcatc cctccaggta    1260
agcagccaaa gagctccccc acggaccccg cactgcctca tcccgcctgt atcggacctg    1320
cgcgacccag cagagaatcc caaacctttg ctgcttgctg cccggttccg gactgagctg    1380
caacccaagc ctttaaaaag cttttccctt ctcccacggt gtcaactctg tcctatccct   1440
ccgacatccg ttgagctcaa caactccccg aaccttttac cccgcgccga gctacccctc    1500
catcaaacca ccctgacagc tcgctcactc acctccccac atcacagaaa tcaaaatgac    1560
tatcaaggtc ggcatcaacg gtttcggccg tatcggccgt atcgtcttcc gcaactccat    1620
cgagcactcg gatgtcgaga tcgttgccgt caacgacccc ttcattgagc ccaagtacgc    1680
tgtaagtagt ttttttttc cttcctcgcg ttctttcctg ttccatcgac agtacgagat     1740
gatcttgcag gcggatcgga gctaaccgcg attgtcgtac aggagtacat gctcaagtat    1800
gactcgaccc acggtatctt caacggcacc atcgccgtcg agggcaacga cctcattgtc    1860
aacggcaaga gggtcaagtt ctacactgag cgggmccccg ccaacattcc ctggarggaa   1920
actggtgccg agtacatmrt cgagtcgacc ggtgtgttca ccamcaccsa gaaggctagc    1980
gcccacctca agggcggcgc caagcgcgtc atcatctctg ctccctcggc cgatgccccc    2040
atgtacgtca tgggcgtcaa cgagaagacc tacgacggca aggcccaggt catctctaac   2100
gcctcgtgca ccaccaactg cctggctccc ctcgccaagg tcatccacga caagttcggc    2160
ctcgttgagg gtctcatgac caccgtccac tcctacactg ccaccagaa gaccgtcgat     2220 ggtccctctg ccaaggactg gcgtggtggc cgtggtgctg ctcagaacat catccccagc    2280
agcactggcg ccgccaaggc cgtcggcaag gtcatccctg agctcaacgg caagctcacc    2340
ggcatgtccc tccgtgtccc cacccccaac gtttccgttg tcgacctcac ctgccgcctc    2400
gagaaggagg ctacctacga cgacatcaag gccgccatca aggaggccgc cgccggcccc    2460
ctcaagggtg agttatctgg ttccttttt ttttttgga gaacgacaca tgctgataaa     2520
acccaggcat cctcgactac actgagg                                       2547
```

<210> SEQ ID NO 5
<211> LENGTH: 5046
<212> TYPE: DNA
<213> ORGANISM: Chrysosporium sp.

<400> SEQUENCE: 5

```
gcttaggaga atcacgagaa gctaattggg ctctatagta tccgacaaga tgacccagag     60
cgagattgag gatctcgagg gaaccctgaa gcagagcagc aacaacgaca ccagcctcct    120
ccgcgacctg ctcgacaaga ttcccgatgg cctcctcggc ggcaacaaca aatccaagct    180
ggacgatatc cagagcaacg cgcaggccgc gcagatggag aacctgagcg tctcgccgcg    240
ggaacccgag gagctgacca gatacgtcca ggaagtgttc cgtcagatca tgcccgccat    300
caagttccat gaccagcttc tccaggacat ctcggaggcc atcgacaaga tcccggtgct    360
gcccaagatt gtggagcagc tggaggagca gatgtccatc tttgtattcc agatcatggc    420
cccgttcgtg gttccgctta tcgagcagat caagaacgag ctcgcgactg gctccagcga    480
gatcatccag agcagcaggg ctgagcagca caacgtcttt gaggacgaca acgccaccga    540
cccgactcac tcgatgttgg ccaaggacca ctttagtaac gtaaagccga ccctaatcag    600
```

```
aagctcgcat gtagaattga gttagactga cgcgacttgt ttcccgtctc tgtagatcct      660
caacgagatc ggcggtcgcg ccgcctccaa ggtcgtctcc tgggtcgtcc cgcagctcat      720
ggaggcctgg gacgatgaca cgtcgacgt ggaccgcctg cttgacaaga tcatttacgg       780
agtgttccac catcccgcgc agcgcaccat gggccctgag ggggcgtccg agggccggga      840
gctcatcttc aacatggtgc gcgagtggtg ggaggacatg agcgacgggc agcgcgacga     900
gtaccggggc aagctgagcc gcgagggagt cgagagaggc gacaaccacc gcgagggcca     960
gcacgactgc ggccacggct gcgggggcaa gctcaagatg cacaagaact tccggaacga    1020
ggcgccccag acggtagagg accagatcgc gggcgccgcc gcggaggcca tcatgggagg    1080
cgtcaagcag ggcctgtcgc aggccgtgca gaacgccgcc ggccgccagg agtcgtcgga    1140
gagcagcggc ctgggtgggt tcatcagcag cgtcgcgggc ggcctcctgg gcggcgccct    1200
caagagggac gagacagagt cgtaccaggc cggcggccgc accgaggacg gcgggtacac    1260
gcagaccacg accgagtacg gctactccgg aggccgctac ggccaggccc agtacacgga    1320
gacgcagtac ggcggcggcg gcggcggccg cagcgagtac cgccgctacg agcagcgcga    1380
ggatgatgac ggccgggtcc agagctacgg atacacggaa cagcgcaccg agacgcgcta    1440
cgacagctac tcggtggct atggcggccg cgaggagacc agcagctatg gcggcggcgg    1500
cagcgcgagc gaatacattc gtagctccca gcagagtagc tacggtggca gcggctatgg    1560
cagtgggtac ggtcgtcgtg atgaagaaga gagcagcggc tatggaagtg gttacggtcg    1620
tcgtgatgaa gaggagagtg gtggttatgg tggcggctat ggccgccgtc aggaagaaga    1680
gagtagcagc tatggaagcg gttatggtcg tcgtcgtgat gaagaagaga gcggcggtta    1740
tggtggtggc tacggccgcc gtcaggaaga agagagtagc ggctatggaa gtggttacgg    1800
tcgtcgtgat gaagaaggga gcggcggtta tggtggtggc tacggccgcc gtcatgagga    1860
agagagcagt ggttacggca gcggctatgg tcgtcgccat gaagaggagg gcggtggcta    1920
cggcagtggt tacggccgcc ggcgcaacga cgaggaggaa gaggaggatg gcggacgccg    1980
gaggtggggt tactagggtg aactcttccg gccggtctct tgttgtgaac cttgctgttg    2040
catgggcagg accggtgcat catgaacagg acggtgcgct gtgttttttt tttctcgggg    2100
tcttgattgt ttgttgaatc tccctttcg aggatacgag ctctctcggg gacgaataga    2160
tgaaggcaat ctgacagatt tgctctcaaa aaaagactga tatctcttcc accatgcact    2220
gtatgtacat tacatacatt atccccctcc actggattcg cacaacggaa agcaatggcg    2280
cgctgattca agaaccatca gggctgtcat tggcttgttt tgtgccgtgg ccgcggtgac    2340
gcccactatg actctctggg caggcggcaa ctgggtgcca gatatattaa tccggggcat    2400
agcgcatatc ttccttgatt tgtagagtac tagtacacta accccttct ccacatgggg     2460 ccactgttcg gtagatctgc ccgaagtgca agtgcggggg gggccaaact aggtaatatc    2520
ctcccgctct cccgagtgcg cggactaacc gtcattgctc ccagaggctt gcactctatc    2580
gcaggccttt tccaataagg atgggccgtt cggcggtgat gatgccggtc gtgcggggca    2640
tacggggagg gtagatagaa aataacgacg ctggtgtttt ggagaggga gggggactat     2700 taggggaggg aaatacaggg gcaggggtg agacgggtga cgttccggcg gaacctcgcg     2760
cttgtcaaac aagcagccct gttaggttgc tctagactag tgtacataca tacatatgta    2820
catactgtat gtactgcaca tactttaact tggtgcttcc ctgtgagccg ccaggaacat    2880
cacaactgca agcggaaaag gccccatata cggggcggct tgtcgggatg gctccccct     2940
```

-continued

```
tcggaacggg tctgacttcc gaggatttta cctgcttcat ttgggtattc tgcgatggcc   3000
tgttcaaccc ttcccctggc cgaaccgttt cttggctcga tcctagtgta cactacacta   3060
ctcgtagact gcctgcccga cgatccgcgg gaacgggcca ggagtgtgga gtggagacgg   3120
gcggcggtga tgtcgtgtaa ttaaatatat aagtgagagt gttttttgac tgccccgggt   3180
tctggtagtt gaagggaagt tcgatgctct ctgctgtcgt cgctctcgtc gctctcgtcg   3240
gcatcctcca tccgtccgcc tttgataacc cgctcccga ctcagtcaag acgacgcata   3300
cttggcacca tgcatctctc cgccaccacc gggttcctcg ccctcccggc cctggccctg   3360
gcccagctct cgggcagcgg ccagacgacc cggtactggg actgctgcaa gccgagctgc   3420
gcctggcccg gcaagggccc ctcgtctccg gtgcaggcct cgacaagaa cgacaacccg   3480
ctcaacgacg gcggctccac ccggtccggc tgcgacgcgg gcggcagcgc ctacatgtgc   3540
tcctcccaga gccctgggc cgtcagcgac gagctgtcgt acggctgggc ggccgtcaag   3600
ctcgccggca gctccgagtc gcagtggtgc tgcgcctgct acgagctgac cttcaccagc   3660
gggccggtcg cgggcaagaa gatgattgtg caggcgacca caccggtgg cgacctgggc   3720
gacaaccact ttgacctggc cgtgagttgc ctccccttct ccccggaccg ctcagattag   3780
atgagattag actttgctcg taaatcggtc caagattccc ttgactgacc aacaaacatc   3840
atacgggcag atccccggtg gcggtgtcgg tattttcaac ggtaagctgg tgcccccgga   3900
cccctcccg gacccctccc ccttttcctc cagcgagccg agttgggatc gccgagatcg   3960
agaactcaca caacttctct ctcgacagcc tgcaccgacc agtacggcgc tcccccgaac   4020
ggctggggcg accgctacgg cggcatccat tccaaggaag agtgcgaatc cttcccggag   4080
gccctcaagc ccggctgcaa ctggcgcttc gactggtacg ttgctttgac ataccggaac   4140
ccaattcctc caaccccccc ccttttctcc cccaactccg ggggtagtcg gaatgtcgcg   4200
actgacccta tttcaggttc caaaacgccg caacccgtc ggtcaccttc caggaggtgg   4260
cctgcccgtc ggagctcacg tccaagagcg gctgctcccg ttaagaggga agagaggggg   4320
ctggaaggac cgaaagattc aacctctgct cctgctgggg aagctcgggc gcgagtgtga   4380
aactggtgta atattgtgg cacacacaag ctactacagt ccgtctcgcc gtccggctaa   4440
ctagccttgc tgcggatctg tccatcttcg gtccgaactg tccgttgctg ttttggctcg   4500
gtgcctcatc ttctcccaac ctagtcaaga atgaatcgtg agagaggctg agagagataa   4560
gatcgacttc agaaatccag ggttgaaagc aataaaaaaa attcctgtgg gatgaatatc   4620
tcgtgatgca acgaccctcc taggaaacct tgacgaaatt tgctgacggc aaattcttca   4680
aagactcgtt aaccggtcgc ccgtagtggt cctgttgccc caatccgttt gtgttgaaat   4740
gacattgcgc gtaacgccgg actcatatca actgcgtacc gaaagccaat ccctccccaa   4800
acacgccctc tctaataagc tctcccaaac aagacctctt gagacagaaa atacgcccag   4860
atgctgagga cttgacaagc cgggggggggg gggggcttg tcaagtgcaa aaacttgccc   4920
atttcatgct ggtatcaaaa aaacaaaaaa aaaaaaaaac atttcaagtc gcggatgccc   4980
catttacatt gcttgcgtgc gccaatagaa acttgcaaca cgtcagtgtc atcttgcacg   5040
ccttgg                                                               5046
```

<210> SEQ ID NO 6
<211> LENGTH: 4376
<212> TYPE: DNA
<213> ORGANISM: Chrysosporium sp.

<400> SEQUENCE: 6

-continued

```
ggatccacac ctaccatacc ggatagtatg ctacccaagt gacataggqt tggtaaagta      60
atacgagaac tcagagagca ctgcccatat ggctcgccaa tgacctcaag tgccaggtca     120
gctttgcgag acagacctga gcgcgtcgga tgtgtgacat ggaacgcgcc ggatcgcctt     180
gttgattaat tataqqqaag tagcgaggaa ggtttcagca attgacgtga gcgtacatta     240
aaagctgtat gatttcagga agacgagcca tggaccaggt ttcaaggctg aatggcttga     300
cgacttaagc accgaacgag gaatgaaaga atgaaaagtg ggggatcatt ctggcccctc     360
ctcgtatgtc gagtgttaaa gaaggcggtt ctacggagga cctaaagagc tccaatttgc     420
tctgttgagc ttaagccaca tatctcaaga tgaatacatg tcaggcatag tcaccctgat     480
cttgttcatc agtccacaca cttttcagtt cagcatgttg attcctcatc catatcactt     540
tccattacta tctctttatg tccttggtca agactccaag gaaccgatag gtgagcatcg     600
gtgaggctcc ctcaaggtac caagtagcc atcatcaccg aggtctggga atggcgccgt      660
gcccgatctg agtcctccaa ctccacggta cgacgacagc acgtcacatt gacgcaccac     720
ggttgaacaa gcagagaggg acacgtcttg ctacgcgaat cctggcactg gatggagacg     780
cgtgtgagca ggtttccgga accatgacgg cctggtccgg cttctcgaac aaagaagtgg     840
aacacaaaaa gaaccgaaac ggaaacgcag gcacggcatc gacgaccgga ttgtcccacg     900
gggacctcgg ccagtcaagc gttgccctgg ccgtcagctc cctggcgacg gggattcagc     960
acatctcacg ttataggcga cctcatcccc cttccgtctt gtgcggtcgt tgctccgtgc    1020
cgagtaccca ggcgtgccgg ggcctttagc cggggcggaa tcagagtcaa gatgcggccg    1080
aattggacgg cagacgaagt ttcgtagagg gtcatgatcg gcactgacga cacccacccc    1140
tgcgtgatcc cgtggccctg ggctgggaat tgccggctaa taatctacgg cttaatagat    1200
atgcactttg cacgcggtgc agataaataa gctgtggttt caaacactgg cctccgtact    1260
ttacccacca actgccgctt agcgccggga cctgagtctt gggagtgcgc ggagcggcag    1320
ccacctcggg ttagcgtaca cacgacggct gcatgcgggg atgccgcgtg catggcttca    1380
tagtgtacga cagaccgtca agtccaaatc tgggtgatgc ttgatgagat gacagcgagc    1440
cccgtcggcg gcaccccggc tatgcatcgc gaattgacaa cactctcagc tctattgcga    1500
cccatcggat aaaagaagaa gaaaaaaatg gaccttgagt acgggcgtca gaaaccaaaa    1560
aaaaactccg gaaccaaata tgtcgggcat ggccggggtg aacgaccgct actcccgtt     1620
cccttcttcg caaacagaac gctacagagg gtttctggt tgtcaaaga gttcggaggt     1680
cctctgctcc gcgaatgcgt ggtgaaccca ccagcagcca ttgttcttgc atgcgtggcg    1740
gaccgttagc cgctgatcga catggcgagc ttcccacctc agacctggag cagacggttg    1800
cgaggagcaa ggggctgccc tcccctgac ggtcggaccc caatgacttc cccaaacggg     1860
gacatcgagg gtcgtgcatg atggtggaaa gtagttgcag tatgggaagt accccggqtt    1920
gccaggaacc gttgttcggc cccccacatt ttctctctgc catgtcaact gtgtgtcgtt    1980
cgagagttcc tggctccggc ccccgtcca attccctaac gggaccgcgg ggcatcgcct     2040
gtaactaact tccaaatgaa gccggatatg agggagggag attggatctg caagccagc     2100
cattcgctgc gatcggcact cgtccgtcag ccccgcagtc catatcccca aaggcaactg    2160
ctcggcgcgg ctcaagtctt cttcggaacg tccagcccga aggcgcgcgc cagcaccggc    2220
cctatgttcc tgattgcgat cctcgatctc cagagacggg tcacctcgcc tcgaggacgt    2280
tgcaggggca tcggcttcgc ttcctagagc tccgggctgt gtgtggtcaa ggggagaagg    2340
```

-continued

```
cggcggcgcc aaggtgcgtc tcggcgcact cacccatcgc ctttaccccc ctcccccca    2400 gtatataaaa gatggccatc gtctcctcgt ctgcttggga agaaaggatc tctcgaccat    2460
gcaccacagc ctagctctaa cccagcttgt cgtgtgttgt tgcccagcat gaagttcgtg    2520
cagtccgcca ccctggcgtt cgccgccacg gccctcgctg cgccctcgcg cacgactccc    2580
cagaagcccc gccaggcctc ggcggctgc gcgtcggccg tgacgctcga tgccagcacc    2640
aacgtgttcc agcagtacac gctgcacccc aacaacttct accgtgccga ggtcgaggct    2700
gccgccgagg ccatctccga ctcggcgctg gccgagaagg cccgcaaggt cgccgacgtc    2760
ggtaccttcc tgtggctcga caccatcgag aacattggcc ggctggagcc cgcgctcgag    2820
gacgtgccct gcgagaacat cgtgggtctc gtcatctacg acctcccggg ccgtgactgc    2880
gcggccaagg cctccaacgg cgagctcaag gtcggcgagc tcgacaggta caagaccgag    2940
tacatcgaca gtgagttaac cctttgtggc cccttctttt cccccgagag agcgtctggt    3000 tgagtgggt tgtgagagag aaaatggggc gagcttaaag actgacgtgt tggctcgcag    3060
agatcgccga gatcctcaag gcccactcca acacggcctt cgccctcgtc atcgagcccg    3120
actcgctccc caacctggtc accaatagcg acctgcagac gtgccagcag agcgcttccg    3180
gctaccgcga gggtgtcgcc tatgccctca agcagctcaa cctccccaac gtggtcatgt    3240
acatcgatgc cggccacggt ggctggctcg gctgggacgc caacctcaag cccggcgccc    3300
aggagctcgc cagcgtctac aagtctgctg gttcgccctc gcaagtccgc ggtatctcca    3360
ccaacgtggc tggttggaac gcctggtaag acactctatg tcccctcgt cggtcaatgg    3420 cgagcggaat ggcgtgaaat gcatggtgct gacctttgat cttttccccc tcctataggg    3480
accaggagcc cggtgagttc tcggacgcct cggatgccca gtacaacaag tgccagaacg    3540
agaagatcta catcaacacc tttggcgctg agctcaagtc tgccggcatg cccaaccacg    3600
ccatcatcga cactggccgc aacggtgtca ccggtctccg cgacgagtgg ggtgactggt    3660
gcaacgtcaa cggcgccggc ttcggtgtgc gcccgactgc caacactggc gacgagctcg    3720
ccgacgcctt cgtgtgggtc aagcccggtg gcgagtccga cggcaccagc gactcgtcgg    3780
cggcgcgcta cgacagcttc tgcggcaagc ccgacgcctt caagcccagc cccgaggccg    3840
gtacctggaa ccaggcctac ttcgagatgc tcctcaagaa cgccaacccg tccttctaag    3900
ctcctcgacg gcttcttgct gtcagtcgct ctgacggtgg tgtgctggtg gtgcccctgc    3960
tcctgctgct gctgctccgc ggggaggga ggcaacgaaa atgaagtcct gcttcaaaac    4020
aaaacagaaa caagcgaggc gcggtgcaat ggtcgtgcgt tcgtcttttt tcatgttccc    4080
ttctagtgta gtagtttgat agtcgtacat aaggggtttc agaaccgtct ctctgtctcg    4140 gtcttttttgc gagttgttgc gactcgtgat tatggccttt gttgctcgtt gcggcagagt    4200
agaaccacag cgtgttgggg tagcagcttg ctccgtagga cgtagggaaa caacctgaga    4260
ctctggaatt gcagtcagcc tgcgtcgccc ctctaggaaa cgaaggggag aaccagtagt    4320
ggctgcagct tacaaacgcg agcatggtga acatctccga gaaagggag ggatcc        4376
```

<210> SEQ ID NO 7
<211> LENGTH: 440
<212> TYPE: DNA
<213> ORGANISM: Chrysosporium sp.

<400> SEQUENCE: 7

```
tgaccttctc ctccttctcc cgaacaataa tagataatta cgagccggtt cgaggctgac      60
attgcgcgat tctagcgagc cgcaatcaat tcaactttgc caacgccgac gcggttgtca     120
```

```
actttgccca ggccaacggc aagctcatcc gcggccacac cctcctctgg cactctcagc      180
tgccgcagtg ggtgcagaac atcaacgacc gcaacacctt gacccaggtc atcgagaacc      240
acgtcaccac ccttgtcact cgctacaagg gcaagatcct ccactgggac gtcgttaacg      300
agatctttgc cgaggacggc tcgctccgcg acagcgtctt cagccgcgtc ctcggcgagg      360
actttgtcgg catcgccttc cgcgccgccc gcgccgccga tcccaacgcc aagctctaca      420
tcaacgacta caggtcgaca                                                  440
```

<210> SEQ ID NO 8
<211> LENGTH: 487
<212> TYPE: DNA
<213> ORGANISM: Chrysosporium sp.
<220> FEATURE:
<221> NAME/KEY: modified_base
<222> LOCATION: (61)
<223> OTHER INFORMATION: a, t, c, g, other or unknown
<220> FEATURE:
<221> NAME/KEY: modified_base
<222> LOCATION: (260)
<223> OTHER INFORMATION: a, t, c, g, other or unknown
<220> FEATURE:
<221> NAME/KEY: modified_base
<222> LOCATION: (263)
<223> OTHER INFORMATION: a, t, c, g, other or unknown
<220> FEATURE:
<221> NAME/KEY: modified_base
<222> LOCATION: (295)
<223> OTHER INFORMATION: a, t, c, g, other or unknown
<220> FEATURE:
<221> NAME/KEY: modified_base
<222> LOCATION: (308)
<223> OTHER INFORMATION: a, t, c, g, other or unknown

<400> SEQUENCE: 8

```
gaattcgggg attacgagct aatgatctgg tcagtttttt ttttcttttt tcttttcttc       60
ncttttcttt tcttttcctt tctcctgttt tattttctta tccattgctt cgccctcttt      120
ccttaaccct gctgactctc tcttcttgtc aatgatactg taataggctg gcagagattcg     180 gcgacgtcta ccccatcggc tcgtcccagg gccacgtcaa cgtggccggc caggactggg      240
agctgtggac gggcttcaan ggnaacatgc gggtctacag cttcgtagcg cccanccccc      300
gcaacagntt cagcgccaac gtcaaggact tcttcaacta tctccagtcc aaccagggct      360
tcccggccag cagccaatac cttctcaagt aaggagacga gatctcgaac agcataccat      420
atatgcgtgc ggtacaagtg cactaacccc cttttttttcc cgttcgcagt cttccagttc     480
ggcactg                                                                487
```

<210> SEQ ID NO 9
<211> LENGTH: 472
<212> TYPE: DNA
<213> ORGANISM: Chrysosporium sp.
<220> FEATURE:
<221> NAME/KEY: modified_base
<222> LOCATION: (4)
<223> OTHER INFORMATION: a, t, c, g, other or unknown
<220> FEATURE:
<221> NAME/KEY: modified_base
<222> LOCATION: (468)
<223> OTHER INFORMATION: a, t, c, g, other or unknown

<400> SEQUENCE: 9

```
tttngggcgc cgtcttactc ctaccttgca ccgtgatcgg ccagtcgcgc tgcgagggcg       60
actcgtgcgg cggtacctac agcaccgacc gctatgccgg catctgcgac cccgacggat      120
```

```
gcgacttcaa ctcgtaccgc cagggcaaca agaccttcta cggcaagggc atgacggtcg    180
acacgaccaa gaagatcacg gtcgtcaccc agttcctcaa gaactcggcc ggcgagctct    240
ccgagatcaa gcggttctac gtccagaacg gcaaggtcat ccccaactcc gagtccacca    300
tcccgggcgt cgagggcaac tccatcaccc aggactggtg cgaccgccag aaggccgcct    360
tcggcgacgt gaccgacttc caggacaagg gcggcatggt ccagatgggc aaggccctcg    420
cggggcccat ggtcctcgtc atgtccatat gggacgacca cgccagtnaa ca            472
```

<210> SEQ ID NO 10
<211> LENGTH: 526
<212> TYPE: PRT
<213> ORGANISM: Chrysosporium lucknowense
<220> FEATURE:
<221> NAME/KEY: MOD_RES
<222> LOCATION: (249)
<223> OTHER INFORMATION: Variable amino acid
<220> FEATURE:
<221> NAME/KEY: MOD_RES
<222> LOCATION: (365)
<223> OTHER INFORMATION: Variable amino acid

<400> SEQUENCE: 10

```
Met Tyr Ala Lys Phe Ala Thr Leu Ala Ala Leu Val Ala Gly Ala Ala
 1               5                  10                  15

Ala Gln Asn Ala Cys Thr Leu Thr Ala Glu Asn His Pro Ser Leu Thr
            20                  25                  30

Trp Ser Lys Cys Thr Ser Gly Gly Ser Cys Thr Ser Val Gln Gly Ser
        35                  40                  45

Ile Thr Ile Asp Ala Asn Trp Arg Trp Thr His Arg Thr Asp Ser Ala
    50                  55                  60

Thr Asn Cys Tyr Glu Gly Asn Lys Trp Asp Thr Ser Tyr Cys Ser Asp
65                  70                  75                  80

Gly Pro Ser Cys Ala Ser Lys Cys Cys Ile Asp Gly Ala Asp Tyr Ser
                85                  90                  95

Ser Thr Tyr Gly Ile Thr Thr Ser Gly Asn Ser Leu Asn Leu Lys Phe
            100                 105                 110

Val Thr Lys Gly Gln Tyr Ser Thr Asn Ile Gly Ser Arg Thr Tyr Leu
        115                 120                 125

Met Glu Ser Asp Thr Lys Tyr Gln Met Phe Gln Leu Leu Gly Asn Glu
    130                 135                 140

Phe Thr Phe Asp Val Asp Val Ser Asn Leu Gly Cys Gly Leu Asn Gly
145                 150                 155                 160

Ala Leu Tyr Phe Val Ser Met Asp Ala Asp Gly Gly Met Ser Lys Tyr
                165                 170                 175

Ser Gly Asn Lys Ala Gly Ala Lys Tyr Gly Thr Gly Tyr Cys Asp Ser
            180                 185                 190

Gln Cys Pro Arg Asp Leu Lys Phe Ile Asn Gly Glu Ala Asn Val Glu
        195                 200                 205

Asn Trp Gln Ser Ser Thr Asn Asp Ala Asn Ala Gly Thr Gly Lys Tyr
    210                 215                 220

Gly Ser Cys Cys Ser Glu Met Asp Val Trp Glu Ala Asn Asn Met Ala
225                 230                 235                 240

Ala Ala Phe Thr Pro His Pro Cys Xaa Val Ile Gly Gln Ser Arg Cys
                245                 250                 255

Glu Gly Asp Ser Cys Gly Gly Thr Tyr Ser Thr Asp Arg Tyr Ala Gly
            260                 265                 270
```

-continued

```
Ile Cys Asp Pro Asp Gly Cys Asp Phe Asn Ser Tyr Arg Gln Gly Asn
        275                 280                 285

Lys Thr Phe Tyr Gly Lys Gly Met Thr Val Asp Thr Thr Lys Lys Ile
    290                 295                 300

Thr Val Val Thr Gln Phe Leu Lys Asn Ser Ala Gly Glu Leu Ser Glu
305                 310                 315                 320

Ile Lys Arg Phe Tyr Val Gln Asn Gly Lys Val Ile Pro Asn Ser Glu
                325                 330                 335

Ser Thr Ile Pro Gly Val Glu Gly Asn Ser Ile Thr Gln Asp Trp Cys
            340                 345                 350

Asp Arg Gln Lys Ala Ala Phe Gly Asp Val Thr Asp Xaa Gln Asp Lys
        355                 360                 365

Gly Gly Met Val Gln Met Gly Lys Ala Leu Ala Gly Pro Met Val Leu
    370                 375                 380

Val Met Ser Ile Trp Asp Asp His Ala Val Asn Met Leu Trp Leu Asp
385                 390                 395                 400

Ser Thr Trp Pro Ile Asp Gly Ala Gly Lys Pro Gly Ala Glu Arg Gly
                405                 410                 415

Ala Cys Pro Thr Thr Ser Gly Val Pro Ala Glu Val Glu Ala Glu Ala
            420                 425                 430

Pro Asn Ser Asn Val Ile Phe Ser Asn Ile Arg Phe Gly Pro Ile Gly
        435                 440                 445

Ser Thr Val Ser Gly Leu Pro Asp Gly Gly Ser Gly Asn Pro Asn Pro
    450                 455                 460

Pro Val Ser Ser Ser Thr Pro Val Pro Ser Ser Ser Thr Thr Ser Ser
465                 470                 475                 480

Gly Ser Ser Gly Pro Thr Gly Gly Thr Gly Val Ala Lys His Tyr Glu
                485                 490                 495

Gln Cys Gly Gly Ile Gly Phe Thr Gly Pro Thr Gln Cys Glu Ser Pro
            500                 505                 510

Tyr Thr Cys Thr Lys Leu Asn Asp Trp Tyr Ser Gln Cys Leu
        515                 520                 525
```

<210> SEQ ID NO 11
<211> LENGTH: 383
<212> TYPE: PRT
<213> ORGANISM: Chrysosporium lucknowense

<400> SEQUENCE: 11

```
Met Arg Thr Leu Thr Phe Val Leu Ala Ala Ala Pro Val Ala Val Leu
  1               5                  10                  15

Ala Gln Ser Pro Leu Trp Gly Gln Cys Gly Gly Gln Gly Trp Thr Gly
             20                  25                  30

Pro Thr Thr Cys Val Ser Gly Ala Val Cys Gln Phe Val Asn Asp Trp
         35                  40                  45

Tyr Ser Gln Cys Val Pro Gly Ser Ser Asn Pro Pro Thr Gly Thr Thr
     50                  55                  60

Ser Ser Thr Thr Gly Ser Thr Pro Ala Pro Thr Gly Gly Gly Gly Ser
 65                  70                  75                  80

Gly Thr Gly Leu His Asp Lys Phe Lys Ala Lys Gly Lys Leu Tyr Phe
                 85                  90                  95

Gly Thr Glu Ile Asp His Tyr His Leu Asn Asn Asn Ala Leu Thr Asn
            100                 105                 110

Ile Val Lys Lys Asp Phe Gly Gln Val Thr Glu Asn Ser Leu Lys Trp
        115                 120                 125

```
Asp Ala Thr Glu Pro Ser Arg Asn Gln Phe Asn Phe Ala Asn Ala Asp
        130                 135                 140

Ala Val Val Asn Phe Ala Gln Ala Asn Gly Lys Leu Ile Arg Gly His
145                 150                 155                 160

Thr Leu Leu Trp His Ser Gln Leu Pro Gln Trp Val Gln Asn Ile Asn
                165                 170                 175

Asp Arg Asn Thr Leu Thr Gln Val Ile Glu Asn His Val Thr Thr Leu
            180                 185                 190

Val Thr Arg Tyr Lys Gly Lys Ile Leu His Trp Asp Val Val Asn Glu
        195                 200                 205

Ile Phe Ala Glu Asp Gly Ser Leu Arg Asp Ser Val Phe Ser Arg Val
    210                 215                 220

Leu Gly Glu Asp Phe Val Gly Ile Ala Phe Arg Ala Ala Arg Ala Ala
225                 230                 235                 240

Asp Pro Asn Ala Lys Leu Tyr Ile Asn Asp Tyr Asn Leu Asp Ile Ala
                245                 250                 255

Asn Tyr Ala Lys Val Thr Arg Gly Met Val Glu Lys Val Asn Lys Trp
            260                 265                 270

Ile Ala Gln Gly Ile Pro Ile Asp Gly Ile Gly Thr Gln Cys His Leu
        275                 280                 285

Ala Gly Pro Gly Gly Trp Asn Thr Ala Ala Gly Val Pro Asp Ala Leu
    290                 295                 300

Lys Ala Leu Ala Ala Ala Asn Val Lys Glu Ile Ala Ile Thr Glu Leu
305                 310                 315                 320

Asp Ile Ala Gly Ala Ser Ala Asn Asp Tyr Leu Thr Val Met Asn Ala
                325                 330                 335

Cys Leu Gln Val Ser Lys Cys Val Gly Ile Thr Val Trp Gly Val Ser
            340                 345                 350

Asp Lys Asp Ser Trp Arg Ser Ser Asn Pro Leu Leu Phe Asp Ser
        355                 360                 365

Asn Tyr Gln Pro Lys Ala Ala Tyr Asn Ala Leu Ile Asn Ala Leu
    370                 375                 380

<210> SEQ ID NO 12
<211> LENGTH: 247
<212> TYPE: PRT
<213> ORGANISM: Chrysosporium lucknowense

<400> SEQUENCE: 12

Met Gln Pro Phe Leu Leu Leu Phe Leu Ser Ser Val Thr Ala Ala Ser
1               5                   10                  15

Pro Leu Thr Ala Leu Asp Lys Arg Gln Gln Ala Thr Leu Cys Glu Gln
            20                  25                  30

Tyr Gly Tyr Trp Ser Gly Asn Gly Tyr Glu Val Asn Asn Asn Asn Trp
        35                  40                  45

Gly Lys Asp Ser Ala Ser Gly Gly His Gln Cys Thr Tyr Val Asp Ser
    50                  55                  60

Ser Ser Ser Gly Val Ala Trp His Thr Thr Trp Gln Trp Glu Gly
65                  70                  75                  80

Gly Gln Asn Gln Val Lys Ser Phe Ala Asn Cys Gly Leu Gln Val Pro
                85                  90                  95

Lys Gly Arg Thr Ile Ser Ser Ile Ser Asn Leu Gln Thr Ser Ile Ser
            100                 105                 110

Trp Ser Tyr Ser Asn Thr Asn Ile Arg Ala Asn Val Ala Tyr Asp Leu
```

```
                115                 120                    125
Phe Thr Ala Ala Asp Pro Asn His Ala Thr Ser Ser Gly Asp Tyr Glu
        130                 135             140

Leu Met Ile Trp Leu Ala Arg Phe Gly Asp Val Tyr Pro Ile Gly Ser
145                 150                 155                 160

Ser Gln Gly His Val Asn Val Ala Gly Gln Asp Trp Glu Leu Trp Thr
                165                 170                 175

Gly Phe Asn Gly Asn Met Arg Val Tyr Ser Phe Val Ala Pro Ser Pro
                180                 185             190

Arg Asn Ser Phe Ser Ala Asn Val Lys Asp Phe Phe Asn Tyr Leu Gln
                195                 200             205

Ser Asn Gln Gly Phe Pro Ala Ser Ser Gln Tyr Leu Leu Ile Phe Gln
        210                 215                 220

Ala Gly Thr Glu Pro Phe Thr Gly Gly Glu Thr Thr Leu Thr Val Asn
225                 230                 235                 240

Asn Tyr Ser Ala Arg Val Ala
                245

<210> SEQ ID NO 13
<211> LENGTH: 277
<212> TYPE: PRT
<213> ORGANISM: Chrysosporium lucknowense
<220> FEATURE:
<221> NAME/KEY: MOD_RES
<222> LOCATION: (80)
<223> OTHER INFORMATION: Variable amino acid
<220> FEATURE:
<221> NAME/KEY: MOD_RES
<222> LOCATION: (87)
<223> OTHER INFORMATION: Variable amino acid
<220> FEATURE:
<221> NAME/KEY: MOD_RES
<222> LOCATION: (95)
<223> OTHER INFORMATION: Variable amino acid
<220> FEATURE:
<221> NAME/KEY: MOD_RES
<222> LOCATION: (103)
<223> OTHER INFORMATION: Variable amino acid
<220> FEATURE:
<221> NAME/KEY: MOD_RES
<222> LOCATION: (105)
<223> OTHER INFORMATION: Variable amino acid

<400> SEQUENCE: 13

Met Thr Ile Lys Val Gly Ile Asn Gly Phe Gly Arg Ile Gly Arg Ile
1               5                   10                  15

Val Phe Arg Asn Ser Ile Glu His Ser Asp Val Glu Ile Val Ala Val
                20                  25                  30

Asn Asp Pro Phe Ile Glu Pro Lys Tyr Ala Glu Tyr Met Leu Lys Tyr
            35                  40                  45

Asp Ser Thr His Gly Ile Phe Asn Gly Thr Ile Ala Val Glu Gly Asn
        50                  55                  60

Asp Leu Ile Val Asn Gly Lys Arg Val Lys Phe Tyr Thr Glu Arg Xaa
65                  70                  75                  80

Pro Ala Asn Ile Pro Trp Xaa Glu Thr Gly Ala Glu Tyr Ile Xaa Glu
                85                  90                  95

Ser Thr Gly Val Phe Thr Xaa Thr Xaa Lys Ala Ser Ala His Leu Lys
                100                 105                 110

Gly Gly Ala Lys Arg Val Ile Ile Ser Ala Pro Ser Ala Asp Ala Pro
            115                 120                 125

Met Tyr Val Met Gly Val Asn Glu Lys Th

```
                130                 135                 140
Val Ile Ser Asn Ala Ser Cys Thr Thr Asn Cys Leu Ala Pro Leu Ala
145                 150                 155                 160

Lys Val Ile His Asp Lys Phe Gly Leu Val Glu Gly Leu Met Thr Thr
                165                 170                 175

Val His Ser Tyr Thr Ala Thr Gln Lys Thr Val Asp Gly Pro Ser Ala
                180                 185                 190

Lys Asp Trp Arg Gly Arg Gly Ala Ala Gln Asn Ile Ile Pro Ser
                195                 200                 205

Ser Thr Gly Ala Ala Lys Ala Val Gly Lys Val Ile Pro Glu Leu Asn
                210                 215                 220

Gly Lys Leu Thr Gly Met Ser Leu Arg Val Pro Thr Pro Asn Val Ser
225                 230                 235                 240

Val Val Asp Leu Thr Cys Arg Leu Glu Lys Glu Ala Thr Tyr Asp Asp
                245                 250                 255

Ile Lys Ala Ala Ile Lys Glu Ala Ala Gly Pro Leu Lys Gly Ile
                260                 265                 270

Leu Asp Tyr Thr Glu
                275

<210> SEQ ID NO 14
<211> LENGTH: 225
<212> TYPE: PRT
<213> ORGANISM: Chrysosporium sp.

<400> SEQUENCE: 14

Met His Leu Ser Ala Thr Thr Gly Phe Leu Ala Leu Pro Ala Leu Ala
  1               5                  10                  15

Leu Ala Gln Leu Ser Gly Ser Gly Gln Thr Thr Arg Tyr Trp Asp Cys
                 20                  25                  30

Cys Lys Pro Ser Cys Ala Trp Pro Gly Lys Gly Pro Ser Ser Pro Val
                 35                  40                  45

Gln Ala Cys Asp Lys Asn Asp Asn Pro Leu Asn Asp Gly Gly Ser Thr
     50                  55                  60

Arg Ser Gly Cys Asp Ala Gly Gly Ser Ala Tyr Met Cys Ser Ser Gln
 65                  70                  75                  80

Ser Pro Trp Ala Val Ser Asp Glu Leu Ser Tyr Gly Trp Ala Ala Val
                 85                  90                  95

Lys Leu Ala Gly Ser Ser Glu Ser Gln Trp Cys Cys Ala Cys Tyr Glu
                100                 105                 110

Leu Thr Phe Thr Ser Gly Pro Val Ala Gly Lys Lys Met Ile Val Gln
                115                 120                 125

Ala Thr Asn Thr Gly Gly Asp Leu Gly Asp Asn His Phe Asp Leu Ala
                130                 135                 140

Ile Pro Gly Gly Gly Val Gly Ile Phe Asn Ala Cys Thr Asp Gln Tyr
145                 150                 155                 160

Gly Ala Pro Pro Asn Gly Trp Gly Asp Arg Tyr Gly Gly Ile His Ser
                165                 170                 175

Lys Glu Glu Cys Glu Ser Phe Pro Glu Ala Leu Lys Pro Gly Cys Asn
                180                 185                 190

Trp Arg Phe Asp Trp Phe Gln Asn Ala Asp Asn Pro Ser Val Thr Phe
                195                 200                 205

Gln Glu Val Ala Cys Pro Ser Glu Leu Thr Ser Lys Ser Gly Cys Ser
                210                 215                 220
```

```
Arg
225

<210> SEQ ID NO 15
<211> LENGTH: 395
<212> TYPE: PRT
<213> ORGANISM: Chrysosporium

<400> SEQUENCE: 15

Met Lys Phe Val Gln Ser Ala Thr Leu Ala Phe Ala Ala Thr Ala Leu
 1               5                  10                  15

Ala Ala Pro Ser Arg Thr Thr Pro Gln Lys Pro Arg Gln Ala Ser Ala
             20                  25                  30

Gly Cys Ala Ser Ala Val Thr Leu Asp Ala Ser Thr Asn Val Phe Gln
         35                  40                  45

Gln Tyr Thr Leu His Pro Asn Asn Phe Tyr Arg Ala Glu Val Glu Ala
     50                  55                  60

Ala Ala Glu Ala Ile Ser Asp Ser Ala Leu Ala Glu Lys Ala Arg Lys
 65                  70                  75                  80

Val Ala Asp Val Gly Thr Phe Leu Trp Leu Asp Thr Ile Glu Asn Ile
                 85                  90                  95

Gly Arg Leu Glu Pro Ala Leu Glu Asp Val Pro Cys Glu Asn Ile Val
            100                 105                 110

Gly Leu Val Ile Tyr Asp Leu Pro Gly Arg Asp Cys Ala Ala Lys Ala
        115                 120                 125

Ser Asn Gly Glu Leu Lys Val Gly Glu Leu Asp Arg Tyr Lys Thr Glu
    130                 135                 140

Tyr Ile Asp Lys Ile Ala Glu Ile Leu Lys Ala His Ser Asn Thr Ala
145                 150                 155                 160

Phe Ala Leu Val Ile Glu Pro Asp Ser Leu Pro Asn Leu Val Thr Asn
                165                 170                 175

Ser Asp Leu Gln Thr Cys Gln Gln Ser Ala Ser Gly Tyr Arg Glu Gly
            180                 185                 190

Val Ala Tyr Ala Leu Lys Gln Leu Asn Leu Pro Asn Val Val Met Tyr
        195                 200                 205

Ile Asp Ala Gly His Gly Gly Trp Leu Gly Trp Asp Ala Asn Leu Lys
    210                 215                 220

Pro Gly Ala Gln Glu Leu Ala Ser Val Tyr Lys Ser Ala Gly Ser Pro
225                 230                 235                 240

Ser Gln Val Arg Gly Ile Ser Thr Asn Val Ala Gly Trp Asn Ala Trp
                245                 250                 255

Asp Gln Glu Pro Gly Glu Phe Ser Asp Ala Ser Asp Ala Gln Tyr Asn
            260                 265                 270

Lys Cys Gln Asn Glu Lys Ile Tyr Ile Asn Thr Phe Gly Ala Glu Leu
        275                 280                 285

Lys Ser Ala Gly Met Pro Asn His Ala Ile Ile Asp Thr Gly Arg Asn
    290                 295                 300

Gly Val Thr Gly Leu Arg Asp Glu Trp Gly Asp Trp Cys Asn Val Asn
305                 310                 315                 320

Gly Ala Gly Phe Gly Val Arg Pro Thr Ala Asn Thr Gly Asp Glu Leu
                325                 330                 335

Ala Asp Ala Phe Val Trp Val Lys Pro Gly Gly Glu Ser Asp Gly Thr
            340                 345                 350

Ser Asp Ser Ser Ala Ala Arg Tyr Asp Ser Phe Cys Gly Lys Pro Asp
        355                 360                 365
```

```
Ala Phe Lys Pro Ser Pro Glu Ala Gly Thr Trp Asn Gln Ala Tyr Phe
    370                 375                 380

Glu Met Leu Leu Lys Asn Ala Asn Pro Ser Phe
385                 390                 395

<210> SEQ ID NO 16
<211> LENGTH: 121
<212> TYPE: PRT
<213> ORGANISM: Chrysosporium sp.

<400> SEQUENCE: 16

Ser Arg Asn Gln Phe Asn Phe Ala Asn Ala Asp Ala Val Val Asn Phe
  1               5                  10                  15

Ala Gln Ala Asn Gly Lys Leu Ile Arg Gly His Thr Leu Leu Trp His
             20                  25                  30

Ser Gln Leu Pro Gln Trp Val Gln Asn Ile Asn Asp Arg Asn Thr Leu
         35                  40                  45

Thr Gln Val Ile Glu Asn His Val Thr Thr Leu Val Thr Arg Tyr Lys
     50                  55                  60

Gly Lys Ile Leu His Trp Asp Val Val Asn Glu Ile Phe Ala Glu Asp
 65                  70                  75                  80

Gly Ser Leu Arg Asp Ser Val Phe Ser Arg Val Leu Gly Glu Asp Phe
                 85                  90                  95

Val Gly Ile Ala Phe Arg Ala Ala Arg Ala Ala Asp Pro Asn Ala Lys
             100                 105                 110

Leu Tyr Ile Asn Asp Tyr Arg Ser Thr
         115                 120

<210> SEQ ID NO 17
<211> LENGTH: 8
<212> TYPE: PRT
<213> ORGANISM: Chrysosporium sp.

<400> SEQUENCE: 17

Gly Asp Tyr Glu Leu Met Ile Trp
  1               5

<210> SEQ ID NO 18
<211> LENGTH: 73
<212> TYPE: PRT
<213> ORGANISM: Chrysosporium sp.
<220> FEATURE:
<221> NAME/KEY: MOD_RES
<222> LOCATION: (31)
<223> OTHER INFORMATION: Variable amino acid
<220> FEATURE:
<221> NAME/KEY: MOD_RES
<222> LOCATION: (43)
<223> OTHER INFORMATION: Variable amino acid
<220> FEATURE:
<221> NAME/KEY: MOD_RES
<222> LOCATION: (47)
<223> OTHER INFORMATION: Variable amino acid

<400> SEQUENCE: 18

Leu Ala Arg Phe Gly Asp Val Tyr Pro Ile Gly Ser Ser Gln Gly His
  1               5                  10                  15

Val Asn Val Ala Gly Gln Asp Trp Glu Leu Trp Thr Gly Phe Xaa Gly
             20                  25                  30

Asn Met Arg Val Tyr Ser Phe Val Ala Pro Xaa Pro Arg Asn Xaa Phe
         35                  40                  45
```

-continued

```
Ser Ala Asn Val Lys Asp Phe Phe Asn Tyr Leu Gln Ser Asn Gln Gly
            50              55                  60

Phe Pro Ala Ser Ser Gln Tyr Leu Leu
 65              70
```

<210> SEQ ID NO 19
<211> LENGTH: 154
<212> TYPE: PRT
<213> ORGANISM: Chrysosporium sp.

<400> SEQUENCE: 19

```
Gly Ala Val Leu Leu Leu Pro Cys Thr Val Ile Gly Gln Ser Arg Cys
 1               5                  10                  15

Glu Gly Asp Ser Cys Gly Gly Thr Tyr Ser Thr Asp Arg Tyr Ala Gly
             20                  25                  30

Ile Cys Asp Pro Asp Gly Cys Asp Phe Asn Ser Tyr Arg Gln Gly Asn
             35                  40                  45

Lys Thr Phe Tyr Gly Lys Gly Met Thr Val Asp Thr Thr Lys Lys Ile
         50                  55                  60

Thr Val Val Thr Gln Phe Leu Lys Asn Ser Ala Gly Glu Leu Ser Glu
 65                  70                  75                  80

Ile Lys Arg Phe Tyr Val Gln Asn Gly Lys Val Ile Pro Asn Ser Glu
                 85                  90                  95

Ser Thr Ile Pro Gly Val Glu Gly Asn Ser Ile Thr Gln Asp Trp Cys
             100                 105                 110

Asp Arg Gln Lys Ala Ala Phe Gly Asp Val Thr Asp Phe Gln Asp Lys
             115                 120                 125

Gly Gly Met Val Gln Met Gly Lys Ala Leu Ala Gly Pro Met Val Leu
         130                 135                 140

Val Met Ser Ile Trp Asp Asp His Ala Ser
145                 150
```

TRANSFORMATION SYSTEM IN THE FIELD OF FILAMENTOUS FUNGAL HOSTS

REFERENCE TO PRIOR APPLICATIONS

This is a continuation-in-part of international application PCT/NL99/00618, filed Oct. 6, 1999, which is a continuation-in-part of international application PCT/EP98/06496, filed Oct. 6, 1998.

SUMMARY OF THE INVENTION

The subject invention pertains to a novel transformation system in the field of filamentous fungal hosts for expressing and secreting heterologous proteins or polypeptides. The invention also covers a process for producing large amounts of polypeptide in an economical manner. The system comprises a transformed or transfected fungal strain of the genus Chrysosporium, more particularly of *Chrysosporium lucknowense* and mutants or derivatives thereof It also covers transformants containing Chrysosporium coding sequences. Novel mutant Chrysosporium strains are disclosed as are novel enzymes derived therefrom. The subject invention further relates to novel enzymes derived from filamentous fungi, especially from strains of the genus Chrysosporium, and to coding sequences and expression-regulating sequences for these enzymes.

BACKGROUND TO THE INVENTION

A number of hosts for gene expression and methods of transformation have been disclosed in the prior art. Bacteria are often mentioned e.g. *Escherichia coli*. *E. coli* is however a micro-organism incapable of secretion of a number of proteins or polypeptides and as such is undesirable as host cell for production of protein or polypeptide at the industrial level. An additional disadvantage for *E. coli*, which is valid also for bacteria in general, is that prokaryotes cannot provide additional modifications required for numerous eukaryotic proteins or polypeptides to be produced in an active form. Glycosylation of proteins and proper folding of proteins are examples of processing required to ensure an active protein or polypeptide is produced. To ensure such processing one can sometimes use mammalian cells; however, the disadvantage of such cells is that they are often difficult to maintain and require expensive media. Such transformation systems are therefore not practical for production of proteins or polypeptides at the industrial level. They may be cost efficient for highly priced pharmaceutical compounds requiring relatively low amounts, but certainly not for industrial enzymes.

A number of fungal expression systems have been developed e.g. *Aspergillus niger, Aspergillus awamori, Aspergillus nidulans, Trichoderma reesei*. A number of others have been suggested but for various reasons have not found wide-spread acceptance or use. In general terms the ideal host must fulfil a large number of criteria:

The ideal host must be readily fermented using inexpensive medium.

The ideal host should use the medium efficiently.

The ideal host must produce the polypeptide or protein in high yield, i.e. must exhibit high protein The ideal host should be capable of efficient secretion of the protein or polypeptide.

The ideal host must enable ease of isolation and purification of the desired protein or polypeptide.

The ideal host must process the desired protein or polypeptide such that it is produced in an active form not requiring additional activation or modification steps.

The ideal host should be readily transformed.

The ideal host should allow a wide range of expression regulatory elements to be used thus ensuring ease of application and versatility.

The ideal host should allow use of easily selectable markers that are cheap to use.

The ideal host should produce stable transformants.

The ideal host should allow cultivation under conditions not detrimental to the expressed protein or polypeptide e.g. low viscosity, low shear.

Fungal systems that have not yet found widespread use are described e.g. in U.S. Pat. No. 5,578,463 by Berka et al suggesting Neurospora, Podospora, Endothia, Mucor, Cochoibolus and Pyricularia together with Aspergillus and Trichoderma. However only illustrations of transformation and expression are provided for Aspergillus and Trichoderma and no details are provided for any of the other suggested hosts.

1 WO 96/02563 and U.S. Pat. Nos. 5,602,004, 5,604,129 and 5,695,985 to Novo Nordisk describe the drawbacks of Aspergillus and Trichoderma systems and suggests cultivation conditions for other fungi may be more suited to large scale protein production. The only examples provided for any transformed cultures are those of *Myceliophthora thermophila, Acremonium alabamense, Thielavia terrestris* and *Sporotrichum cellulophilum* strains. The Sporotrichum strain is reported to lyse and produce green pigment under fermentation conditions not leading to such results for the other strains. A non-sporulating mutant of *Thielavia terrestris* is described as being the organism of choice by virtue of its morphology. However it is also stated that the protoplasting efficiency of Thielavia and Acremonium (whereby the Acremonium strain used was the imperfect state of the Thielavia strain used) is low and that hygromycin was not useful as a selection marker. A large number of others are suggested as being potentially useful by virtue of their morphology but no transformation thereof is described. The suggested strains are Corynascus, Thermoascus, Chaetomium, Ctenomyces, Scytalidium and Talaromyces. The transformed hosts are mentioned as only producing low levels of the introduced Humicola xylanase with Thielavia producing the lowest amount; however, the information is ambiguous and could actually infer Thielavia was the best embodiment. The nomenclature of this reference is based on the ATCC names of Industrial Fungi of 1994. Thus it is apparent no high degree of heterologous expression was achieved and in fact no positive correlation could be derived between the postulated morphology and the degree of expression. If any correlation could be made, it was more likely to be negative. According to the 1996 ATCC fungal classification *Sporotrichum thermophilum* ATCC 20493 is a *Myceliophthora thermophila* strain. Currently the strain is still identified as *Myceliophthora thermophila*. The unpredicatability of the art is apparent from these recent disclosures.

Also Allison et al (*Curr. Genetics* 21:225–229, 1992) described transformation of *Humicola grisea* var. thermoidea using the lithium acetate method and a Humicola enzyme-encoding sequence, but no report of expression of heterologous protein from such a strain has been provided.

In 1997 a patent issued to Hawaii Biotechnology Group for transformed Neurospora for expression of mammalian peptide such as chymosin. The transformation of auxotrophic Neurospora crassa occurred with spheroplasts. Endogenous transcriptional regulatory regions were introduced and cotransformation was carried out. Nothing is mentioned concerning other hosts and other transformation protocols. Nothing is apparent from the disclosure concerning the degree of expression. It is doubtful whether the degree of expression is high, as immunotechniques (which are useful for detecting small amounts of protein) are the only techniques used to illustrate the presence of the protein. No actual isolation of the protein is disclosed.

WO 97/26330 of Novo Nordisk suggests a method of obtaining mutants of filamentous fungal parent cells having an improved property for production of heterologous polypeptide. The method comprises first finding a specific altered morphology followed by assessing whether a transformant produces more heterologous polypeptide than the parent. The method is illustrated only for strains of Fusarium A3/5 and *Aspergillus oryzae*. The method is suggested to be applicable for Aspergillus, Trichoderma, Thielavia, Fusarium, Neurospora, Acremonium, Tolyplocadium, Humicola, Scytalidium, Myceliophthora or Mucor. As stated above the unpredictability in the art and also the unpredictability of the method of the cited application do not provide a generally applicable teaching with a reasonable expectation of success.

DETAILED DESCRIPTION OF THE INVENTION

We now describe an alternative fungal expression system with the simplicity of use of the above-mentioned Aspergillus and Trichoderma fulfilling the above requirements. The new system has not been taught or suggested in the prior art. The new system according to the invention provides the additional advantages that transformation rates are higher than those for the frequently used *Trichoderma reesei* system. In addition the culture conditions offer the additional bonus of being advantageous for the expressed polypeptide.

We further describe a number of industrially interesting enzymes derived from the novel expressing system, together with full sequence information. We also describe novel promoter systems derived from Chrysosporium strains and useful for expressing homologous and heterologous genes.

The present invention is thus also concerned with glycosyl hydrolases of the families 7 (e.g. cellobiohydrolases), 10 (e.g. xylanases) and 12 (e.g. endoglucanases), and glyceraldehyde phosphate dehydrogenases, as identified by their amino acid sequence, as well as peptides derived from these enzymatic proteins, and with nucleic acid sequences encoding these peptides and proteins, as well as, in particular, with regulating sequences related to these genes.

In particular, the present invention pertains to isolated or recombinant enzymic proteins or active parts thereof of the four classes referred to above, including mutants thereof having at least a certain degree of sequence identity as specified in the further disclosure and in the claims, as well as nucleic acid sequences encoding these proteins or parts thereof, and/or nucleic acid sequences regulating their expression. These enzymes are especially: (1) a glycosyl hydrolase of family 7 (cellobiohydrolase, CBH1) having at least 75%, preferably at least 80% or even at least 85% amino acid identity with the sequence of SEQ ID No 1; (2) a glycosyl hydrolase of family 10 (endoxylanase XYLF or XYL1) having at least 70%, preferably at least 75% or even at least 80% amino acid identity with the sequence of SEQ ID No 2; (3) a glycosyl hydrolase family of 12 (endoglucanase, EG3) having at least 65%, preferably at least 70% or even at least 80% amino acid identity with the sequence of SEQ ID No. 3; and (4) a glyceraldehyde phosphate dehydrogenase (GPD1) having at least 86%, preferably at least 90% or even at least 93% amino acid identity with the sequence of SEQ ID No 4. Polypeptides and nucleic acid sequences encoding these polypeptides, having at least 20, preferably at least 30 contiguous amino acids of SEQ ID No's 1–4 are also a preferred part of the invention.

The recombinant enzymes may comprise essentially the complete protein, or a truncated protein having at least part of the enzymatic activity. Such truncated part may be the catalytic domain, or at least about 75% of the amino acids thereof. By way of example, the catalytic domain of the CBH1 according to the invention comprises the aminoacids 20–495 of the aminoacid sequence of SEQ ID No. 1, and the catalytic domain of the XYL1 according to the invention comprises the aminoacids 54–384 of the aminoacid sequence of SEQ ID No. 2. The catalytic domain may or may not be combined with a signal sequence originating from another protein and/or with a carbohydrate-binding domain from another enzymic protein. Alternatively, the cellulose-binding domain of the enzymes of the invention (CBH1 and XYL1) may be fused to catalytic domains of other enzymic proteins.

The nucleic acid sequences according to of the invention may be complete protein-encoding regions or oligonucleotides or, preferentially, expression-regulatingsequences. Oligonucleotides may be used also as probes for identifying genes corresponding to, but not identical to the genes of SEQ ID No.'s 1–4; these genes, when fulfilling the percentage identity criteria defined herein, as well as encoding and non-encoding parts thereof and their expression products are also part of the invention.

The invention also pertains to expression systems (cassettes) comprising either an expression-regulatingregion (including a promoter) of any of the four protein classes fused to a gene encoding another protein of interest, or an encoding region of any of these proteins fused to another expression regulating region, or both the expression-regulatingregion and the protein-encoding region of these novel proteins. The expression-regulating region comprises at least 60%, preferably at least 70%, more preferably at least 75% or even 80% of the 5'-non-coding region of SEQ ID No.'s 1–4, and/or at least 20, especially at least 40 contiguous nucleotides from these 5' non-coding regions. Terminating sequences similarly derived from the 3" non-coding regions of the genes of the invention are also useful in expressing cassettes, whether combined with homologous or heterologous genes.

These expression systems may be contained in a Chrysosporium host, such as a *Chrysosporium lucknowense* host, or in another non-fungal or, preferably, fungal host. Examples of other fungal hosts are other Chrysosporium species or strains, Fusarium species, Aspergillus species etc. Such host may be advantageously a host that does not itself, intrinsically or as a result of the culture conditions, produce a protein corresponding to the protein of interest, so as to simplify the recovery of the protein of interest.

Where reference is made in this specification and in the appending claims to "polypeptides" or "peptides" or "polypeptides of interest" or "peptides of interest" as the products of the expression system of the invention, this term also comprise proteins, i.e. polypeptides having a particular function and/or secondary and/or tertiary structure. Where reference is made to percentage amino acid identity, such identity relates to e complete protein or a to a specific part defined by initial and final amino acid number, as determined by the conventionally used BLAST algorithm.

In the production method of the invention, the pH of the culture medium can be neutral or alkaline thus no longer subjecting the produced protein or polypeptide to aggressive and potentially inactivating acid pH. It is also possible to culture at acid pH such as pH 4 for cases where the protein or polypeptide is better suited to an acidic environment. Suitably culture can occur at a pH between 4.0–10.0. A preference however exists for neutral to alkaline pH as the host strain exhibits better growth at such pH, e.g. between 6 and 9. Growth at alkaline pH which can be from pH 8 up and can even be as high as 10 is also a good alternative for some cases. Also the cultivation temperature of such host strains is advantageous to the stability of some types of produced polypeptide. The cultivation temperature is suitably at a temperature of 25–43° C. A temperature in the range from 40° C. down to 23° C. or 30° C. is also advantageously applied. Clearly such conditions are of particular interest for production of mammalian polypeptides. The selected temperature will depend on cost effectiveness of the cultivation and sensitivity of the polypeptide or cultivation strain. The conditions will be determined by the skilled person without undue burden on a case-by-case basis, as is common in the art.

It has also been ascertained that the biomass to viscosity relation and the amount of protein produced is exceedingly favourable for the host according to the invention. Comparisons have been carried out with *Trichoderma longibrachiatum* (formerly also known as *Trichoderma reesei*) and with *Aspergillus niger*. *Trichoderma longibrachiatum* gave 2.5–5 g/l biomass, *Aspergillus niger* gave 5–10 g/l biomass and the host according to the invention gave 0.5–1 g/l biomass under their respective optimised conditions. This thus offers 5–10 fold improvement over the commercially used strains. These commercial strains are strains which themselves are considered in the art to be high producers of proteins and they are successfully used for commercial protein production. They have been cultured under their optimal conditions developed and run viably in large-scale commercial fermenters. The same strains were used to illustrate enormous improvement in viscosity values for cultures of the host according to the invention. At the end of the fermentation process *Trichoderma longibrachiatum* gave a value of 200–600 cP (Centipoise), *Aspergillus niger* gave a value of 1500–2000 cP and the host according to the invention gave a value below 10 cP. This thus provides at least 20–200 fold improvement for viscosity values over the commercially used strains. A quite surprising further aspect was that the protein levels determined for the host cells according to the invention were much higher than for the commercial Aspergillus and *Trichoderma reesei* strains, even with the above mentioned surprisingly low biomass and viscosity levels. In summary an easy to use versatile improved transformation system and expression system with improved culturing conditions has hereby been introduced. The strains according to the invention produce surprisingly higher protein levels under these improved conditions and in addition they do such in a shorter fermenter time.

The subject invention is directed at mutant Chrysosporium strains comprising a nucleic acid sequence encoding a heterologous protein or polypeptide, said nucleic acid sequence being operably linked to an expression regulating region and optionally a secretion signal encoding sequence and/or a carrier protein encoding sequence. Preferably a recombinant strain according to the invention will secrete the polypeptide of interest. This will avoid the necessity of disrupting the cell in order to isolate the polypeptide of interest and also minimise the risk of degradation of the expressed product by other components of the host cell.

Chrysosporium can be defined by morphology consistent with that disclosed in Barnett and Hunter 1972, Illustrated Genera of Imperfect Fungi, 3rd Edition of Burgess Publishing Company. Other sources providing details concerning classification of fungi of the genus Chrysosporium are known e.g. Sutton Classification (Van Oorschot, C.A.N. (1980) "A revision of Chrysosporium and allied genera" in Studies in Mycology No. 20 of the CBS in Baarn The Netherlands p1–36). CBS is one of the depository institutes of the Budapest Treaty. According to these teachings the genus Chrysosporium falls within the family Moniliaceae which belongs to the order Hyphomycetales. The criteria that can be used are the following:

1. Signs of Hyphomycetales Order:
Conidia are produced directly on mycelium, on separate sporogenous cells or on distinct conidiophores.
2. Signs of Moniliaceae Family:
Both conidia and conidiophores (if present) are hyaline or brightly coloured; conidiophores are single or in loose clusters.
3. Signs of Chrysosporium Corda 1833 Genus:
Colonies are usually spreading, white, sometimes cream-coloured, pale brown or yellow, felty and/or powdery. Hyphae are mostly hyaline and smooth-walled, with irregular, more or less orthotopic branching. Fertile hyphae exhibit little or no differentiation. Conidia are terminal and lateral, thallic, borne all over the hyphae, sessile or on short protrusions or side branches, subhyaline or pale yellow, thin- or thick-walled, subglobose, clavate, pyriform, orobovoid, 1-celled, rarely 2-celled, truncate. Intercalary conidia are sometimes present, are solitary, occasionally catenate, subhyaline or pale yellow, broader than the supporting hyphae, normally 1-celled, truncate at both ends. Chlamydospores are occasionally present.

Another source providing information on fungal nomenclature is ATCC (US). Their website may be accessed on the World Wide Web (HTTP protocol) at atcc.org. CBS also has a website located on the World Wide Web (HTTP protocol) at cbs.knaw.nl providing relevant information. VKM in Moscow is also a reliable source of such information, located on the World Wide Web (HTTP protocol) at bdt.org.br.bdt.msdn.vkm/general. Another source is the United States Department of Agriculture, Agricultural Research Service website (located on an NT webserver rather than the World Wide Web) at ars-grin.gov/fungaldatabases. All these institutions can provide teaching on the distinguishing characteristics of a Chrysosporium.

Strains defined as being of *Myceliophthora thermophila* are not considered to define Chrysosporium strains according to the definition of the invention. In the past there has been considerable confusion over the nomenclature of some Myceliophthora strains. Preferably the Chrysosporium according to the invention are those which are clearly distinguishable as such and cannot be confused with Myceliophthora, Sporotrichum or *Phanerochaete chrysosporium*.

The following strains are defined as Chrysosporium but the definition of Chrysosporium is not limited to these strains: *C. botryoides, C. carmichaelii, C. crassitunicatum, C. europae, C. evolceannui, C. farinicola, C. fastidium, C. filiforme, C. georgiae, C. globiferum, C. globiferum var. articulatum, C. globiferum var. niveum, C. hirundo, C. hispanicum, C. holmii, C. indicum, C. inops, C. keratinophilum, C. kreiselii, C. kuzurovianum, C. lignorum, C. lobatum, C. lucknowense, C. lucknowense Garg* 27K, *C. medium, C. medium var. spissescens, C. mephiticum, C. merdarium, C. merdarium var. roseum, C. minor, C. pannicola, C. parvum, C. parvum var. crescens, C. pilosum, C. pseudomerdarium, C. pyriformis, C queenslandicum, C.*

*sigleri, C. sulfureum, C. synchronum, C. tropicum, C. undulatum, C. vallenarense, C. vespertilium, C. zonatum.*

*C. lucknowense* forms one of the species of Chrysosporium that have raised particular interest as it has provided a natural high producer of cellulase proteins (WO 98/15633 and related U.S. Pat. No. 5,811,381, as well as U.S. Pat. No. 6,015,707). The characteristics of this *Chrysosporium lucknowense* are:

Colonies attain 55 mm diameter on Sabouraud glucose agar in 14 days, are cream-coloured, felty and fluffy; dense and 3–5 mm high; margins are defined, regular, and fimbriate; reverse pale yellow to cream-coloured. Hyphae are hyaline, smooth- and thin-walled, little branched. Aerial hyphae are mostly fertile and closely septate, about 1–3.5 μm wide. Submerged hyphae are infertile, about 1–4.5 μm wide, with the thinner hyphae often being contorted. Conidia are terminal and lateral, mostly sessile or on short, frequently conical protrusions or short side branches. Conidia are solitary but in close proximity to one another, 1–4 conidia developing on one hyphal cell, subhyaline, fairly thin- and smooth-walled, mostly subglobose, also clavate orobovoid, 1-celled, 2.5–11×1.5–6 μm, with broad basal scars (1–2 μm). Intercalary conidia are absent. Chlamydospores are absent. ATCC 44006, CBS 251.72, CBS 143.77 and CBS 272.77 are examples of *Chrysosporium lucknowense* strains and other examples are provided in WO 98/15633 and U.S. Pat. No. 5,811,381.

A further strain was isolated from this species with an even higher production capacity for cellulases. This strain is called C1 by its internal notation and was deposited with the International Depository of the All Russian Collection of micro-organisms of the Russian Academy of Sciences Bakrushina Street 8, Moscow, Russia 113184 on Aug. 29, 1996, as a deposit according to the Budapest Treaty and was assigned Accession Number VKM F-3500D. It is called *Chrysosporium lucknowense* Garg 27K. The characteristics of the C1 strain are as follows:

Colonies grow to about 55–66 mm diameter in size on potato-dextrose agar in about 7 days; are white-cream-coloured, felty, 2–3 μm high at the center; margins are defined, regular, fimbriate; reverse pale, cream-coloured. Hyphae are hyaline, smooth- and thin-walled, little branched. Aerial hyphae are fertile, septate, 2–3 mm wide. Submerged hyphae are infertile. Conidia are terminal and lateral; sessile or on short side branches; absent; solitary, but in close proximity to one another, hyaline, thin- and smooth-walled, subglobose, clavate or obovoid, 1-celled, 4–10 μm. Chlamydo-spores are absent. Intercalary conidia are absent.

The method of isolation of the C1 strain is described in WO 98/15633 and U.S. Pat. No. 5,811,381. Strains exhibiting such morphology are included within the definition of Chrysosporium according to the invention. Also included within the definition of Chrysosporium are strains derived from Chrysosporium predecessors including those that have mutated somewhat either naturally or by induced mutagenesis. In particular the invention covers mutants of Chrysosporium obtained by induced mutagenis, especially by a combination of irradiation and chemical mutagenesis.

For example strain C1 was mutagenised by subjecting it to ultraviolet light to generate strain UV13-6. This strain was subsequently further mutated with N-methyl-N'-nitro-N-nitrosoguanidineto generate strain NG7C-19. The latter strain in turn was subjected to mutation by ultraviolet light resulting in strain UV18-25. During this mutation process the morphological characteristics have varied somewhat in culture in liquid or on plates as well as under the microscope. With each successive mutagenesis the cultures showed less of the fluffy and felty appearance on plates that are described as being characteristic of Chrysosporium, until the colonies attained a flat and matted appearance. A brown pigment observed with the wild type strain in some media was also less prevalent in mutant strains. In liquid culture the mutant UV18-25 was noticeably less viscous than the wild type strain C1 and the mutants UV13-6 and NG7C-19. While all strains maintained the gross microscopic characteristics of Chrysosporium, the mycelia became narrower with each successive mutation and with UV18-25 distinct fragmentation of the mycelia could be observed. This mycelial fragmentation is likely to be the cause of the lower viscosity associated with cultures of UV18-25. The ability of the strains to sporulate decreased with each mutagenic step. The above illustrates that for a strain to belong to the genus Chrysosporium there is some leeway from the above morphological definition. At each mutation step production of cellulase and extracellular proteins has in addition also increased, while several mutations resulted in decrease of protease expression. Criteria with which fungal taxonomy can be determined are available from CBS, VKMF and ATCC for example.

In particular the anamorph form of Chrysosporium has been found to be suited for the production application according to the invention. The metabolism of the anamorph renders it extremely suitable for a high degree of expression. A teleomorph should also be suitably as the genetic make-up of the anamorphs and teleomorphs is identical. The difference between anamorph and teleomorph is that one is the asexual state and the other is the sexual state. The two states exhibit different morphology under certain conditions.

It is preferable to use non-toxic Chrysosporium strains of which a number are known in the art as this will reduce risks to the environment upon large scale production and simplify production procedures with the concomitant reduction in costs.

An expression-regulatingregion is a DNA sequence recognised by the host Chrysosporium strain for expression. It comprises a promoter sequence operably linked to a nucleic acid sequence encoding the polypeptide to be expressed. The promoter is linked such that the positioning vis-à-vis the initiation codon of the sequence to be expressed allows expression. The promoter sequence can be constitutive or inducible. Any expression regulating sequence or combination thereof capable of permitting expression of a polypeptide from a Chrysosporium strain is envisaged. The expression regulating sequence is suitably a fungal expression-regulatingregion e.g. an ascomycete regulating region. Suitably the fungal expression regulating region is a regulating region from any of the following genera of fungi: Aspergillus, Trichoderma, Chrysosporium (preferred), Hansenula, Mucor, Pichia, Neurospora, Tolypocladium, Rhizomucor, Fusarium, Penicillium, Saccharomyces, Talaromyces or alternative sexual forms thereof like Emericella, Hypocrea e.g. the cellobiohydrolase promoter from Trichoderma, glucoamylase promoter from Aspergillus, glyceraldehyde phosphate dehydrogenase promoter from Aspergillus, alcohol dehydrogenase A and alcohol dehydrogenase R promoter of Aspergillus, TAKA amylase promoter from Aspergillus, phosphoglycerate and cross-pathway control promoters of Neurospora, aspartic proteinase promoter of *Rhizomucor miehei*, lipase promoter of *Rhizomucor miehei* and beta-galactosidase promoter of *Penicillium canescens*. An expression regulating sequence from the same genus as the host strain is extremely suitable, as it is most likely to be specifically adapted to the specific host. Thus preferably the expression regulating sequence is one from a Chrysosporium strain.

We have found particular strains of Chrysosporium to express proteins in extremely large amounts and natural expression regulating sequences from these strains are of particular interest. These strains are internally designated as Chrysosporium strain C1, strain UV13-6, strain NG7C-19 and strain UV18-25. They have been deposited in accordance with the Budapest Treaty with the All Russian Collection (VKM) depository institute in Moscow. Wild type C1 strain was deposited in accordance with the Budapest Treaty with the number VKM F-3500 D, deposit date Aug. 29, 1996, C1 UV13-6 mutant was deposited with number VKM F-3632 D, and deposit date Sep. 02, 1998, C1 NG7c-19 mutant was deposited with number VKM F-3633 D and deposit date Sep. 02, 1998 and C1 UV18-25 mutant was deposited with number VKM F-3631 D and deposit date Sep. 02, 1998.

Preferably an expression-regulating region enabling high expression in the selected host is applied. This can also be a high expression-regulatingregion derived from a heterologous host, such as are well known in the art. Specific examples of proteins known to be expressed in large quantities and thus providing suitable expression regulating sequences for the invention are without being limited thereto hydrophobin, protease, amylase, xylanase, pectinase, esterase, beta-galactosidase, cellulase (e.g. endo-glucanase, cellobiohydrolase) and polygalacturonase. The high production has been ascertained in both solid state and submerged fermentation conditions. Assays for assessing the presence or production of such proteins are well known in the art. The catalogues of Sigma and Megazyme for example provide numerous examples. Megazyme is located at Bray Business Park, Bray, County Wicklow in Ireland. Sigma Aldrich has many affiliates world wide e.g. USA P.O. Box 14508 St. Louis Mo. For cellulase we refer to commercially available assays such as CMCase assays, endoviscometric assays, Avicelase assays, beta-glucanase assays, RBBCMCase assays, Cellazyme C assays. Xylanase assays are also commercially available (e.g. DNS and Megazyme). Alternatives are well known to a person skilled in the art and can be found from general literature concerning the subject and such information is considered incorporated herein by reference. By way of example we refer to "Methods in Enzymology Volume 1, 1955 right through to volumes 297–299 of 1998. Suitably a Chrysosporium promoter sequence is applied to ensure good recognition thereof by the host.

We have found that heterologous expression-regulating sequences work as efficiently in Chrysosporium as native Chrysosporium sequences. This allows well known constructs and vectors to be used in transformation of Chrysosporium as well as offering numerous other possibilities for constructing vectors enabling good rates of expression in this novel expression and secretion host. For example standard Aspergillus transformation techniques can be used as described for example by Christiansen et al in Bio/Technol. 6:1419–1422 (1988). Other documents providing details of Aspergillus transformation vectors, e.g. U.S. Pat. Nos. 4,816,405, 5,198,345, 5,503,991, 5,364,770 and 5,578,463, EP-B-215.594 (also for Trichoderma) and their contents are incorporated by reference. As extremely high expression rates for cellulase have been ascertained for Chrysosporium strains, the expression regulating regions of such proteins are particularly preferred. We refer for specific examples to the previously mentioned deposited Chrysosporium strains.

A nucleic acid construct comprising a nucleic acid expression regulatory region from Chrysosporium, preferably from *Chrysosporium lucknowense* or a derivative thereof forms a separate embodiment of the invention as does the mutant Chrysosporium strain comprising such operably linked to a gene encoding a polypeptide to be expressed. Suitably such a nucleic acid construct will be an expression regulatory region from Chrysosporium associated with cellulase or xylanase expression, preferably cellobiohydrolase expression, more specifically expression of a 55 kDa cellobiohydrolase. The Chrysosporium promoter sequences of an endoglucanase of 25 kDa (C1-EG5) and of an endoglucanase of 43 kDa (C1-EG6), wherein the molecular weights are determined according to SDS PAGE (with the molecular weights according to amino acid sequence data being 21.9 kDa and 39.5 kDa), are provided by way of example. Thus, the Chrysosporium promoter sequences of hydrophobin, protease, amylase, xylanase, esterase, pectinase, beta-galactosidase, cellulase (e.g. endoglucanase, cellobiohydrolase)and polygalacturonase are considered to also fall within the scope of the invention. Any of the promoters or regulatory regions of expression of enzymes disclosed in Table A or B can be suitably employed. The nucleic acid sequence according to the invention can suitably be obtained from a Chrysosporium strain according to the invention, such strain being defined elsewhere in the description. The manner in which promoter sequences can be determined are numerous and well known in the art. Nuclease deletion experiments of the region upstream of the ATG codon at the beginning of the relevant gene will provide such sequence. Also for example analysis of consensus sequences can lead to finding a gene of interest. Using hybridisation and amplification techniques one skilled in the art can readily arrive at the corresponding promoter sequences.

The promoter sequences of C1 endoglucanases were identified in this manner, by cloning the corresponding genes, and are given in SEQ ID No.'s 5 (EG5) and 6 (EG6), respectively. Other preferred promoters according to the invention are the 55 kDa cellobiohydrolase (CBH1) promoter and the 30 kDa xylanase (XylF) promoters, as the enzymes are expressed at high level by their own promoters. The corresponding promoter sequences can be identified in a straightforward manner by cloning as described below for the endoglucanase promoters, using the sequence information given in SEQ ID No. 1 (for CBH1) and SEQ ID No. 2 (for XylF), respectively. The promoters of the carbohydrate-degradingenzymes of Chrysosporium, especially C1 promoters, can advantageously be used for expressing desired polypeptides in a host organism, especially a fungal or other microbial host organism. Promoter sequences having at least 60%, preferably at least 70%, most preferably at least 80% nucleotide sequence identity with the sequence given in SEQ ID No's 1 and 2, or with the sequences found for other Chrysosporium genes, are part of the present invention.

For particular embodiments of the recombinant strain and the nucleic acid sequence according to the invention we also refer to the examples. We also refer for the recombinant strains to prior art describing high expression promoter sequences in particular those providing high expression in fungi e.g. such as are disclosed for Aspergillus and Trichoderma. The prior art provides a number of expression regulating regions for use in Aspergillus e.g. U.S. Pat. No. 5,252,726 of Novo and U.S. Pat. No. 5,705,358 of Unilever. The contents of such prior art are hereby incorporated by reference.

The hydrophobin gene is a fungal gene that is highly expressed. It is thus suggested that the promoter sequence of a hydrophobin gene, preferably from Chrysosporium, may be suitably applied as expression regulating sequence in a suitable embodiment of the invention. *Trichoderma reesei* and *Trichoderma harzianum* gene sequences for hydrophobin have been disclosed for example in the prior art as well as a gene sequence for *Aspergillus fumigatus* and *Aspergillus nidulans* and the relevant sequence information is hereby incorporated by reference (Munoz et al, Curr. Genet. 1997, 32(3):225–230; Nakari-Setala T. et al, *Eur. J Biochem.* 1996 15:235 (1–2):248–255, M. Parta et al, *Infect. Immun.* 1994 62 (10):4389–4395 and Stringer M. A. et al. *Mol. Microbiol.* 1995 16(1):33–44). Using this sequence information a person skilled in the art can obtain the expression regulating sequences of Chrysosporium hydrophobin genes without undue experimentation following standard techniques as suggested already above. A recombinant Chrysosporium strain according to the invention can comprise a hydrophobin-regulatingregion operably linked to the sequence encoding the polypeptide of interest.

An expression regulating sequence can also additionally comprise an enhancer or silencer. These are also well known in the prior art and are usually located some distance away from the promoter. The expression regulating sequences can also comprise promoters with activator binding sites and repressor binding sites. In some cases such sites may also be modified to eliminate this type of regulation. Filamentous fungal promoters in which creA sites are present have been described. Such creA sites can be mutated to ensure the glucose repression normally resulting from the presence of the non-mutated sites is eliminated. Gist-Brocades' WO 94/13820 illustrates this principle. Use of such a promoter enables production of the polypeptide encoded by the nucleic acid sequence regulated by the promoter in the presence of glucose. The same principle is also apparent from WO 97/09438. These promoters can be used either with or without their creA sites. Mutants in which the creA sites have been mutated can be used as expression regulating sequences in a recombinant strain according to the invention and the nucleic acid sequence it regulates can then be expressed in the presence of glucose. Such Chrysosporium promoters ensure derepression in an analogous manner to that illustrated in WO 97/09438. The identity of creA sites is known from the prior art. Alternatively, it is possible to apply a promoter with CreA binding sites that have not been mutated in a host strain with a mutation elsewhere in the repression system e.g. in the creA gene itself, so that the strain can, notwithstanding the presence of creA binding sites, produce the protein or polypeptide in the presence of glucose.

Terminator sequences are also expression-regulating sequences and these are operably linked to the 3' terminus of the sequence to be expressed. Any fungal terminator is likely to be functional in the host Chrysosporium strain according to the invention. Examples are *A. nidulans* trpC terminator (1), *A. niger* alpha-glucosidase terminator (2), *A. niger* glucoamylase terminator (3), *Mucor miehei* carboxyl protease terminator (U.S. Pat. No. 5,578,463) and the *Trichoderma reesei* cellobiohydrolase terminator. Naturally Chrysosporium terminator sequences will function in Chrysosporium and are suitable e.g. CBH1 or EG6 terminator.

A suitable recombinant Chrysosporium strain according to the invention has the nucleic acid sequence to be expressed operably linked to a sequence encoding the amino acid sequence defined as signal sequence. A signal sequence is an amino acid sequence which when operably linked to the amino acid sequence of the expressed polypeptide allows secretion thereof from the host fungus. Such a signal sequence may be one normally associated with the heterologous polypeptide or may be one native to the host. It can also be foreign to both host and the polypeptide. The nucleic acid sequence encoding the signal sequence must be positioned in frame to permit translation of the signal sequence and the heterologous polypeptide. Any signal sequence capable of permitting secretion of a polypeptide from a Chrysosporium strain is envisaged. Such a signal sequence is suitably a fungal signal sequence, preferably an ascomycete signal sequence.

Suitable examples of signal sequences can be derived from yeasts in general or any of the following specific genera of fungi: Aspergillus, Trichoderma, Chrysosporium, Pichia, Neurospora Rhizomucor, Hansenula, Humicola, Mucor, Tolypocladium, Fusarium, Penicillium, Saccharomyces, Talaromyces or alternative sexual forms thereof like Emericella, Hypocrea. Signal sequences that are particularly useful are often natively associated with the following proteins a cellobiohydrolase, an endoglucanase, a beta-galactosidase,a xylanase, a pectinase, an esterase, a hydrophobin, a protease or an amylase. Examples include amylase or glucoamylase of Aspergillus or Humicola (4), TAKA amylase of *Aspergillus oryzae*, alpha-amylase of *Aspergillus niger*, carboxyl peptidase of Mucor (U.S. Pat. No. 5,578,463), a lipase or proteinase from *Rhizomucor miehei*, cellobiohydrolase of Trichoderma (5), beta-galactosidase of *Penicillium canescens* and alpha mating factor of Saccharomyces.

Alternatively the signal sequence can be from an amylase or subtilisin gene of a strain of Bacillus. A signal sequence from the same genus as the host strain is extremely suitable as it is most likely to be specifically adapted to the specific host thus preferably the signal sequence is a signal sequence of Chrysosporium. We have found particular strains of Chrysosporium to excrete proteins in extremely large amounts and naturally signal sequences from these strains are of particular interest. These strains are internally designated as Chrysosporium strain C1, strain UV13-6, strain NG7C-19 and strain UV18-25. They have been deposited in accordance with the Budapest Treaty as described elsewhere in this description. Signal sequences from filamentous fungi, yeast and bacteria are useful. Signal sequences of non-fungal origin are also considered useful, particularly bacterial, plant and mammalian.

A recombinant Chrysosporium strain according to any of the embodiments of the invention can further comprise a selectable marker. Such a selectable marker will permit easy selection of transformed or transfected cells. A selectable marker often encodes a gene product providing a specific type of resistance foreign to the non-transformed strain. This can be resistance to heavy metals, antibiotics and biocides in general. Prototrophy is also a useful selectable marker of the non-antibiotic variety. Non-antibiotic selectable markers can be preferred where the protein or polypeptide of interest is to be used in food or pharmaceuticals with a view to speedier or less complicated regulatory approval of such a product. Very often the GRAS indication is used for such markers. A number of such markers are available to the person skilled in the art. The FDA e.g. provides a list of such. Most commonly used are selectable markers selected from the group conferring resistance to a drug or relieving a nutritional defect e.g the group comprising amdS (acetamidase), hph (hygromycin phosphotransferase), pyrG (orotidine-5'-phosphatedecarboxylase), trpC (anthranilate synthase), argB (ornithine carbamoyltransferase), sC (sulphate adenyltransferase), bar (phosphinothricin acetyltransferase), glufosinate resistance, niaD (nitrate reductase), a bleomycin resistance gene, more specifically Sh ble, sulfonylurea resistance e.g. acetolactate synthase mutation ilv1. Selection can also be carried out by virtue of cotransformation where the selection marker is on a separate vector or where the selection marker is on the same nucleic acid fragment as the polypeptide-encoding sequence for the polypeptide of interest.

As used herein the term heterologous polypeptide is a protein or polypeptide not normally expressed and secreted by the Chrysosporium host strain used for expression according to the invention. The polypeptide can be of plant or animal (vertebrate or invertebrate) origin e.g. mammalian, fish, insect, or micro-organism origin, with the proviso it does not occur in the host strain. A mammal can include a human. A micro-organism comprises viruses, bacteria, archaebacteria and fungi i.e. filamentous fungi and yeasts. Bergey's Manual for Bacterial Determinology provides adequate lists of bacteria and archaebacteria. For pharmaceutical purposes quite often a preference will exist for human proteins thus a recombinant host according to the invention forming a preferred embodiment will be a host wherein the polypeptide is of human origin. For purposes such as food production suitably the heterologous polypeptide will be of animal, plant or algal origin. Such embodiments are therefore also considered suitable examples of the invention. Alternative embodiments that are useful also include a heterologous polypeptide of any of bacterial, yeast, viral, archaebacterial and fungal origin. Fungal origin is most preferred.

A suitable embodiment of the invention will comprise a heterologous nucleic acid sequence with adapted codon usage. Such a sequence encodes the native amino acid sequence of the host from which it is derived, but has a different nucleic acid sequence, i.e. a nucleic acid sequence in which certain codons have been replaced by other codons encoding the same amino acid but which are more readily used by the host strain being used for expression. This can lead to better expression of the heterologous nucleic acid sequence. This is common practice to a person skilled in the art. This adapted codon usage can be carried out on the basis of known codon usage of fungal vis-à-vis non-fungal codon usage. It can also be even more specifically adapted to codon usage of Chrysosporium itself. The similarities are such that codon usage as observed in Trichoderma, Humicola and Aspergillus should enable exchange of sequences of such organisms without adaptation of codon usage. Details are available to the skilled person concerning the codon usage of these fungi and are incorporated herein by reference.

The invention is not restricted to the above mentioned recombinant Chrysosporium strains, but also covers a recombinant Chrysosporium strain comprising a nucleic acid sequence encoding a homologous protein for a Chrysosporium strain, said nucleic acid sequence being operably linked to an expression-regulatingregion and said recombinant strain expressing more of said protein than the corresponding non-recombinant strain under the same conditions. In the case of homologous polypeptide of interest such is preferably a neutral or alkaline enzyme like a hydrolase, a protease or a carbohydrate degrading enzyme as already described elsewhere. The polypeptide may also be acidic. Preferably the recombinant strain will express the polypeptide in greater amounts than the non-recombinant strain. All comments mentioned vis-à-vis the heterologous polypeptide are also valid (mutatis mutandis) for the homologous polypeptide cellulase.

Thus the invention also covers genetically engineered Chrysosporium strains wherein the sequence that is introduced can be of Chrysosporium origin. Such a strain can, however, be distinguished from natively occurring strains by virtue of for example heterologous sequences being present in the nucleic acid sequence used to transform or transfect the Chrysosporium, by virtue of the fact that multiple copies of the sequence encoding the polypeptide of interest are present or by virtue of the fact that these are expressed in an amount exceeding that of the non-engineered strain under identical conditions or by virtue of the fact that expression occurs under normally non-expressing conditions. The latter can be the case if an inducible promoter regulates the sequence of interest contrary to the non-recombinant situation or if another factor induces the expression than is the case in the non-engineered strain. The invention as defined in the preceding embodiments is not intended to cover naturally occurring Chrysosporium strains. The invention is directed at strains derived through engineering either using classical genetic technologies or genetic engineering methodologies.

All the recombinant strains of the invention can comprise a nucleic acid sequence encoding a heterologous protein selected from carbohydrate-degrading enzymes (cellulases, xylanases, mannanases, mannosidases, pectinases, amylases, e.g. glucoamylases, -amylases, alpha- and beta-galactosidases, -and -glucosidases, -glucanases, chitinases, chitanases), proteases (endoproteases, amino-proteases, amino-and carboxy-peptidases, keratinases), other hydrolases (lipases, esterases, phytases), oxidoreductases (catalases, glucose-oxidases) and transferases (transglycosylases, transglutaminases, isomerases and invertases).

TABLE A pH range where enzymes retain activity and/or stability

| | pH range retaining > 50% enzymatic activity | | | pH range retaining > 70% enzymatic activity | | | Stability |
|---|---|---|---|---|---|---|---|
| Sample | CMCase | RBB-CMC-ase | Other substrates | CMC-ase | RBB-CMCase | Other substrates | (20 h, 50° C.) % from max pH 7.5/8 |
| 30 Kd protease (alkaline) 30 kD | — | — | 12.5 | — | — | 12.0 | — |
| Xyl (alkaline) | — | — | 10.0 | — | — | 8.5 | 80 |
| 51 kD Xyl | — | — | 8.0 | — | — | 7.5 | — |
| 60 kD Xyl | — | — | 9.5 | — | — | 9.0 | 85 |
| 45 kD endo | 7.0 | 8.0 | — | 6.5 | 7.0 | — | 75 |
| 55 kD endo | 8.0 | 8.0 | — | 7.0 | 7.0 | — | 55 |
| 25 kD (21.8 kD*) endo | 7.5 | 10.0 | — | 6.5 | 9.0 | — | 80 |
| 43 kD (39.6 kD*) endo | 8.0 | 8.0 | — | 7.2 | 7.2 | — | — |

TABLE A-continued

| | pH range where enzymes retain activity and/or stability | | | | | | |
|---|---|---|---|---|---|---|---|
| | pH range retaining > 50% enzymatic activity | | | pH range retaining > 70% enzymatic activity | | | Stability |
| Sample | CMC ase | RBB-CMC-ase | Other substrates | CMC ase | RBB-CMC ase | Other substrates | (20 h, 50° C.) % from max pH 7.5/8 |
| 45 kD, β-Gal/β-Gluc | — | — | 6.8 | — | — | 5.7 | — |
| 48 kD CBH with β-Gluc traces | 5.2 | 7.5 | 8.0 | 5.0 | 6.8 | — | — |
| 55 kD CBH | 8.0 | 9.0 | — | 7.4 | 8.5 | — | 70 |
| 65 kD PGU | — | — | 8.0 | — | — | 7.3 | — |
| 90 kD protease | — | — | 9.0 | — | — | 9.0 | — |
| 100 kD esterase | — | — | 9.0 | — | — | 9.0 | — |

*molecular weights (by MALDI)

Note:
all other molecular weights by SDS PAGE
enzymes were taken in equal protein contents
xyl = xylanase
endo = endoglucanase
gal = galactosidase
gluc = glucosidase
CBN = cellbiohydrolase
PGU = polygalacturonase

TABLE B

Activities of enzymes isolated from ultrafiltrate from 18–25 strain toward different substrates (pH 5), units/mg protein

| Sample | pI | CMC 50° C. | RBB-CMC 40° C. | CMC-41 40° C. | FP 50° C. | CMC (visc) 40° C. | b-Glucan 50° C. | pNP-a-G 40° C. | pNP-b-G 40° C. | Cellobiose 40° C. | Avicel 40° C. | MUF-cellobioside 40° C. |
|---|---|---|---|---|---|---|---|---|---|---|---|---|
| 30 kD protease | 8.9 | 0 | 0 | 0 | 0 | 0 | 0 | — | 0 | 0 | 0 | 0 |
| 30 kD Xyl | 9.1 | 0.1 | 2 | 0.1 | 0.16 | 0.1 | 0 | — | 0 | — | 0 | 0 |
| 51 kD Xyl | 8.7 | 0.1 | 4.2 | — | 0.19 | — | 0 | — | 0 | — | 0 | 0 |
| 60 kD Xyl | 4.7 | 0 | — | — | 0 | — | 0 | — | 0 | — | 0 | 0.14 |
| 45 kD endo | 6 | 51 | 86 | 7.6 | 0.2 | 47 | 36 | — | 0 | — | 0.5 | 0 |
| 55 kD endo | 4.9 | 47 | 94 | 7.7 | 0.3 | 39 | 25 | — | 0 | — | 0.5 | 0 |
| 25 kD (21.8 kD*) endo | 4.1 | 19 | 15 | 3.9 | 0.3 | 11 | 3.8 | — | 0 | 0 | 0.05 | 0 |
| 43 kD (39.6 kD*) endo | 4.2 | 0.43 | 0.2 | 0.1 | 0 | 0.2 | 0.2 | — | 0 | 0 | 0 | 0 |
| 45 kD a,b-Gal/b-Gluc | 4.2 | 0 | 0 | 0 | 0 | 0.01 | 0.01 | 0 | 0.4 | 0.06 | 0 | 0 |
| 48 kD CBH with b-Gluc traces + glucono-d-lactone | 4.4 | 0.67 | 1.3 | 1.2 | 0.4 | 0.8 | 0.77 | 0 | 1.7 0 | 0.08 | 0 | 0.2 |
| 55 kD CBH with b-Gluc traces – glucono-d-lactone | 4.4 | 0.7 | 0.16 | 0.27 | 0.4 | 0.1 | 0.1 | — | 0.05 0 | 0.08 | 0.46 | 0.2 0.14 |
| 65 kD PGU | 4.4 | 0 | 0 | 0 | 0 | 0 | 0 | — | 0 | 0 | 0 | 0 |
| 90 kD protease | 4.2 | — | — | — | — | — | — | — | — | — | — | — |
| 100 kD esterase | 4.5 | 0 | 0 | 0 | 0 | 0 | — | 0 | 0 | 0 | 0 | 0 |

| Sample | MUF-lactoside 40° C. | MUF-xyloside 40° C. | Lactose 40° C. | Xylan 50° C. | Polygalacturonic acid 50° C. | MUF-glucoside 40° C. | Galactomannan 50° C. | pNP-a-galactoside 40° C. | pNP-b-galactoside 40° C. | Dyed casein** 50° C. | pNP butyrate 60° C. |
|---|---|---|---|---|---|---|---|---|---|---|---|
| 30 kD protease | 0 | 0 | 0 | 0 | 0 | 0 | 0 | 0 | 0 | 0.4 | 0 |
| 30 kD Xyl | 0 | 0 | — | 25 | 0 | 0 | 0 | 0 | — | 0 | 0 |
| 51 kD Xyl | 0 | 0 | — | 19 | 0 | 0 | 0 | 0 | — | 0 | 0 |
| 60 kD Xyl | 0.02 | 0.04 | — | 16.3 | 0 | 0 | 0 | 0 | 0 | 0 | 0 |
| 45 kD endo | 0 | 0 | — | 1 | — | 0 | 1.8 | 0 | — | 0 | 0 |
| 55 kD endo | 0 | 0 | — | 0 | — | 0 | 0.4 | 0 | — | 0 | 0 |
| 25 kD (21.8 kD*) endo | 0 | — | 0 | 0.03 | 0 | — | 0 | 0 | 0 | 0 | 0 |
| 43 kD (39.6 kD*) endo | 0 | — | 0 | 0 | 0 | 0 | 0 | 0 | 0 | 0 | 0 |
| 45 kD a,b-Gal/b-Gluc | 0 | — | 0.01 | 0 | 0.1 | 0.1 | 0.2 | 0.2 | 0.3 | 0 | 1.7 |
| 48 kD CBH with b-Gluc traces + glucono-d-lactone | 0.36 0.36 | — | 0 | 0 | 0.1 | 0.4 | 0 | 0 | 0 | 0 | 2.3 |
| 55 kD CBH with b-Gluc traces – glucono-d-lactone | 0.7 0.6 | — | 0 | 0.1 | 0 | — | 0 | 0 | 0 | 0 | 0 |

TABLE B-continued

| | | | | | | | | | | | |
|---|---|---|---|---|---|---|---|---|---|---|---|
| 65 kD PGU | 0 | — | 0 | 0 | 1 | — | 0 | 0 | 0 | 0 | 0 |
| 90 kD protease | — | — | — | — | — | — | — | — | — | 0.01 | — |
| 100 kD esterase | 0 | — | 0 | 0 | 0 | 0 | 0 | 0 | 0 | 0 | 0.8 |

*molecular weights (by MALDI)
**activity toward dyed casein was expressed in arbitrary units/mg The most interesting products to be produced according to invention are cellulases, xylanases, pectinases, lipases and proteases, wherein cellulases and xylanases cleave beta-1, 4-bonds, and cellulases comprise endoglucanases, cellobiohydrolases and beta-glucosidases. These proteins are extremely useful in various industrial processes known in the art. Specifically for cellulases we refer e.g. to WO 98/15633 describing cellobiohydrolases and endoglucanases of use. The contents of said application are hereby incorporated by reference. We also refer to Tables A and B providing further details of interesting Chrysosporium proteins.

It was found according to the invention, that Chrysosporium mutants can be made that have reduced expression of protease, thus making them even more suitable for the production of proteinaceous products, especially if the proteinaceous product is sensitive to protease activity. Thus the invention also involves a mutant Chrysosporium strain which produces less protease than non-mutant Chrysosporium strain, for example less than *C. lucknowense* strain C1 (VKM F-3500 D). In particular the protease acitivity of such strains is less than half the amount, more in particular less than 30% of the amount produced by C1 strain. The decreased protease activity can be measured by known methods, such as by measuring the halo formed op skim milk plates or BSA degradation.

An embodiment of the invention that is of particular interest is a recombinant Chrysosporium according to the invention wherein the nucleic acid sequence encoding the polypeptide of interest encodes a polypeptide that is inactivated or unstable at acid pH i.e. pH below 6, even below pH 5,5, more suitably even below pH 5 and even as low as or lower than pH 4. This is a particularly interesting embodiment, as the generally disclosed fungal expression systems are not cultured under conditions that are neutral to alkaline, but are cultured at acidic pH. Thus the system according to the invention provides a safe fungal expression system for proteins or polypeptides that are susceptible to being inactivated or are unstable at acid pH.

Quite specifically a recombinant strain as defined in any of the embodiments according to the invention, wherein the nucleic acid sequence encoding the polypeptide of interest encodes a protein or polypeptide exhibiting optimal activity and/or stability at a pH above 5, preferably at neutral or alkaline pH (i.e. above 7) and/or at a pH higher than 6, is considered a preferred embodiment of the invention. More than 50%, more than 70% and even more than 90% of optimal activities at such pH values are anticipated as being particularly useful embodiments. A polypeptide expressed under the cultivation conditions does not necessarily have to be active at the cultivation conditions, in fact it can be advantageous for it to be cultured under conditions under which it is inactive as its active form could be detrimental to the host. This is the case for proteases for example. What is however required is for the protein or polypeptide to be stable under the cultivation conditions. The stability can be thermal stability. It can also be stability against specific compositions or chemicals, such as are present for example in compositions or processes of production or application of the polypeptide or protein of interest. LAS in detergent compositions comprising cellulases or lipases, etc. is an example of a chemical often detrimental to proteins. The time periods of use in applications can vary from short to long exposure so stability can be over a varying length of time varying per application. The skilled person will be able to ascertain the correct conditions on a case by case basis. One can use a number of commercially available assays to determine the optimal activities of the various enzymatic products. The catalogues of Sigma and Megazyme for example show such. Specific examples of tests are mentioned elsewhere in the description. The manufacturers provide guidance on the application.

We have surprisingly found that a Chrysosporium strain that can be suitably used to transform or transfect with the sequence of interest to be expressed is a strain exhibiting relatively low biomass. We have found that Chrysosporium strains having a biomass two to five times lower than that of *Trichoderma reesei* when cultured to a viscosity of 200–600 cP at the end of fermentation and exhibiting a biomass of 10 to 20 times lower than that of *Aspergillus niger* when cultured to a viscosity of 1500–2000 cP under corresponding conditions, i.e. their respective optimal cultivation conditions, can provide a high level of expression. This level of expression far exceeds that of the two commercial reference strains at a much lower biomass and at much lower viscosity. This means that the yield of expression of such Chrysosporium strains will be appreciably higher than from *Aspergillus niger* and *Trichoderma reesei*. Such a transformed or transfected Chrysosporium strain forms a suitable embodiment of the invention.

We find a biomass of 0.5–1.0 g/l for Chrysosporium strain C1(18–25) as opposed to 2.5–5.0 g/l for *Trichoderma reesei* and 5–10 g/l of *Aspergillus niger* under the above described conditions. In the Examples we provide details of this process.

In a suitable embodiment a recombinant Chrysosporium strain according to the invention produces protein or polypeptide in at least the amount equivalent to the production in moles per liter of cellulase by the strain UV13-6 or C-19, and most preferably at least equivalent to or higher than that of the strain UV18-25 under the corresponding or identical conditions, i.e. their respective optimal cultivation conditions.

Unexpectedly we have also found that expression and secretion rates are exceedingly high when using a Chrysosporium strain exhibiting the mycelial morphology of strain UV18-25 i.e. fragmented short mycelia. Thus a recombinant strain according to the invention will preferably exhibit such morphology. The invention however also covers non-recombinant strains or otherwise engineered strains of Chrysosporium exhibiting this novel and inventive characteristic. Also covered by the invention is a recombinant Chrysosporium strain in any of the embodiments described according to the invention further exhibiting reduced sporulation in comparison to C1, preferably below that of strain UV13-6, preferably below that of NG7C-19, preferably below that of UV18-25 under equivalent fermenter conditions. Also covered by the invention is a recombinant Chrysosporium strain in any of the embodiments described according to the invention further exhibiting at least the amount of protein production ratio to biomass in comparison to C1, preferably in comparison to that of any of strains UV13-6, NG7C-19 and UV18-25 under equivalent fermenter conditions. The invention however also covers non-recombinant strains or otherwise engineered strains of Chrysosporium exhibiting this novel and inventive characteristic as such or in combination with any of the other embodiments.

Another attractive embodiment of the invention also covers a recombinant Chrysosporium strain exhibiting a viscosity below that of strain NG7C-19, preferably below that of UV18-25 under corresponding or identical fermenter conditions. The invention however also covers non-recombinant strains or otherwise engineered strains of Chrysosporium exhibiting this novel and inventive characteristic as such or in combination with any of the other embodiments. We have determined that the viscosity of a culture of UV18-25 is below 10 cP opposed to that of *Trichoderma reesei* being of the order 200–600 cP, with that of *Aspergillus niger* being of the order 1500–2000 cP under their respective optimal culture conditions at the end of fermentation. The process used for such determination is provided in the examples.

Viscosity can be assessed in many cases by visual monitoring. The fluidity of the substance can vary to such a large extent that it can be nearly solid, sauce like or liquid. Viscosity can also readily be ascertained by Brookfield rotational viscometry, use of kinematic viscosity tubes, falling ball viscometer or cup type viscometer. The yields from such a low viscosity culture are higher than from the commercial known higher viscosity cultures per time unit and per cell.

The processing of such low viscosity cultures according to the invention is advantageous in particular when the cultures are scaled up. The subject Chrysosporium strains with the low viscosity perform very well in cultures as large as up to 150,000 liter cultures. Thus any culture size up to 150,000 litres provides a useful embodiment of the invention. Any other conventional size of fermentation should be carried out well with the strains according to the invention. The reasoning behind this is that problems can arise in large scale production with the formation of aggregates that have mycelia that are too dense and/or are unevenly distributed. The media as a result cannot be effectively utilised during the culture thus leading to an inefficient production process in particular in large scale fermentations i.e. over 150,000 liters. Aeration and mixing become problematic leading to oxygen and nutrient starvation and thus reduced concentration of productive biomass and reduced yield of polypeptide during the culture and/or can result in longer fermentation times. In addition high viscosity and high shear are not desirable in commercial fermentation processes and in current commercial processes they are the production limiting factors. All these negative aspects can be overcome by the Chrysosporium host according to the invention which exhibits much better characteristics than *Trichoderma reesei, Aspergillus niger* and *Aspergillus oryzae* that are commercially used in this respect i.e. exhibits better protein production levels and viscosity properties and biomass figures.

A Chrysosporium strain selected from C1, UV13-6, NG7C-19 and UV18-25 illustrates various aspects of the invention exceedingly well. The invention however also covers recombinant strains or otherwise engineered strains of Chrysosporium derived from the four deposited strains that also exhibit any of the novel and inventive characteristics as such or in combination. The deposit data for these strains have been presented elsewhere in the description. The invention also covers recombinant strains or otherwise engineered strains of Chrysosporium derived from the four deposited strains that also exhibit any of the novel and inventive characteristics as such or in combination. A Chrysosporium strain according to the invention also comprises a strain exhibiting under the corresponding culture conditions a biomass at least twice as low as that of *Trichoderma reesei*, suitably even more up to 5 times lower than that of *Trichoderma reesei*, specifically of a *Trichoderma reesei* exhibiting a viscosity of 200–600 cP as disclosed under the conditions of the examples. A Chrysosporium strain according to the invention also comprises a strain producing the polypeptide in at least the amount in moles per liter of cellulase by the strain C1, UV13-6, NG7C-19 or UV18-25 under the corresponding or identical conditions.

Chrysosporium strains according to the invention are further preferred if they exhibit optimal growth conditions at neutral to alkaline pH and temperatures of 25–43° C. A preference can exist for neutral and even for alkaline pH. Such production conditions are advantageous to a number of polypeptides and proteins, in particular those susceptible to attack by acidic pH or those that are inactive or unstable at low temperatures. It is however also an embodiment of the invention to include Chrysosporium strains that can be cultured at acidic pH as this can be useful for certain proteins and polypeptides. A suitable acidic pH lies from 7.0. An acidic pH lower than 6.5 is envisaged as providing a good embodiment of the invention. A pH around 5.0–7.0 is also a suitable embodiment. A neutral pH can be 7.0 or around 7 e.g. 6.5–7.5. As stated elsewhere the pH of optimal interest depends on a number of factors that will be apparent to the person skilled in the art. A pH higher than 7.5 is alkaline, suitably between 7.5–9.0 can be used.

When comparing data of strains according to the invention with other strains perhaps having other optimal conditions (e.g. Aspergillus and Trichoderma) for viscosity measurements, biomass determination or protein production comparisons should be made using the relevant optimal conditions for the relevant strain. This will be obvious to the person skilled in the art.

A Chrysosporium strain according to any of the above-mentioned embodiments of the invention, said strain further exhibiting production of one or more of the fungal enzymes selected from the carbohydrate-degrading enzymes, proteases, other hydrolases, oxidoreductase, and transferases mentioned above is considered a particularly useful embodiment of the invention. The most interesting products are specifically cellulases, xylanases, pectinases, lipases and proteases. Also useful as embodiment of the invention however is a Chrysosporium strain exhibiting production of one or more fungal enzymes that exhibit neutral or alkaline optimal stability and/or activity, preferably alkaline optimal stability and/or activity, said enzyme being selected from carbohydrate-degrading enzymes, hydrolases and proteases, preferably hydrolases and carbohydrate-degrading enzymes. In the case of non-recombinant Chrysosporium, such enzymes are suitably other than cellulase as disclosed in WO 98/15633. Enzymes of particular interest are xylanases, proteases, esterases, alpha galactosidases, beta-galactosidases, beta-glucanases and pectinases. The enzymes are not limited to the aforementioned. The comments vis-à-vis stability and activity elsewhere in the description are valid here also.

The invention also covers a method of producing a polypeptide of interest, said method comprising culturing a Chrysosporium strain in any of the embodiments according to the invention under conditions permitting expression and preferably secretion of the polypeptide and recovering the subsequently produced polypeptide of interest.

Where protein or polypeptide is mentioned, variants and mutants e.g. substitution, insertion or deletion mutants of naturally occurring proteins are intended to be included that exhibit the activity of the non-mutant. The same is valid vis-à-vis the corresponding nucleic acid sequences. Processes such as gene shuffling, protein engineering and directed evolution site directed mutagenesis and random mutagenesis are processes through which such polypeptides, variants or mutants can be obtained. U.S. Pat. No. 5,223,409, U.S. Pat. No. 5,780,279 and U.S. Pat. No. 5,770,356 provide teaching of directed evolution. Using this process a library of randomly mutated gene sequences created for example by gene shuffling via error prone PCR occurs in any cell type. Each gene has a secretion region and an immobilising region attached to it such that the resulting protein is secreted and stays fixed to the host surface. Subsequently conditions are created that necessitate the biological activity of the particular polypeptide. This occurs for a number of cycles ultimately leading to a final gene with the desired characteristics. In other words a speeded up directed process of evolution. U.S. Pat. No. 5,763,192 also describes a process for obtaining DNA, RNA, peptides, polypeptides or protein by way of synthetic polynucleotide coupling stochastically generated sequences, introduction thereof into a host followed by selection of the host cell with the corresponding predetermined characteristic.

Another application of the method of the present invention is in the process of "directed evolution", wherein novel protein-encoding DNA sequences are generated, the encoded proteins are expressed in a host cell, and those sequences encoding proteins having a desired characteristic are mutated and expressed again. The process is repeated for a number of cycles until a protein with the desired characteristics is obtained. Gene shuffling, protein engineering, error-prone PCR, site-directed mutagenesis, and combinatorial and random mutagenesis are examples of processes through which novel DNA sequences encoding exogenous proteins can be generated. U.S. Pat. Nos. 5,223,409, 5,780, 279 and 5,770,356 provide teaching of directed evolution. See also Kuchner and Arnold, Trends in Biotechnology, 15:523–530(1997); Schmidt-Dannert and Arnold, Trends in Biotech., 17:135–136 (1999); Arnold and Volkov, Curr. Opin. Chem. Biol., 3:54–59 (1999); Zhao et al., Manual of Industrial Microbiology and Biotechnology, 2nd Ed., (Demain and Davies, eds.) pp. 597–604, ASM Press, Washington DC, 1999; Arnold and Wintrode, Encyclopedia of Bioprocess Technology: Fermentation, Biocatalysis, and Bioseparation, (Flickinger and Drew, eds.) pp. 971–987, John Wiley & Sons, New York, 1999; and Minshull and Stemmer, Curr. Opin. Chem. Biol. 3:284–290.

An application of combinatorial mutagenesis is disclosed in Hu et al., Biochemistry. 1998 37:10006–10015. U.S. Pat. No. 5,763,192 describes a process for obtaining novel protein-encoding DNA sequences by stochastically generating synthetic sequences, introducing them into a host, and selecting host cells with the desired characteristic. Methods for effecting artificial gene recombination (DNA shuffling) include random priming recombination (Z. Shao, et al., Nucleic Acids Res., 26:681–683 (1998)), the staggered extension process (H. Zhao et al., Nature Biotech., 16:258–262 (1998)), and heteroduplex recombination (A. Volkov et al., Nucleic Acids Res., 27: e18 (1999)). Error-prone PCR is yet another approach (Song and Rhee, Appl. Environ. Microbiol. 66:890–894 (2000)).

There are two widely-practiced methods of carrying out the selection step in a directed evolution process. In one method, the protein activity of interest is somehow made essential to the survival of the host cells. For example, if the activity desired is a cellulase active at pH 8, a cellulase gene could be mutated and introduced into the host cells. The transformants are grown with cellulose as the sole carbon source, and the pH raised gradually until only a few survivors remain. The mutated cellulase gene from the survivors, which presumably encodes a cellulase active at relatively high pH, is subjected to another round of mutation, and the process is repeated until transformants that can grow on cellulose at pH 8 are obtained. Thermostable variants of enzymes can likewise be evolved, by cycles of gene mutation and high-temperature culturing of host cells (Liao et al., Proc. Natl. Acad. Sci. USA 83:576–580(1986); Giver et al., Proc. Natl. Acad. Sci. USA. 95:12809–12813 (1998).

An alternative to the massively parallel "survival of the fittest" approach is serial screening. In this approach, individual transformants are screened by traditional methods, such as observation of cleared or colored zones around colonies growing on indicator media, colorimetric or fluorometric enzyme assays, immunoassays, binding assays, etc. See for example Joo et al., Nature 399:670–673 (1999), where a cytochrome P450 monooxygenase not requiring NADH as a cofactor was evolved by cycles of mutation and screening; May et al., Nature Biotech. 18:317–320 (2000), where a hydantoinase of reversed stereoselectivity was evolved in a similar fashion; and Miyazaki et al., J. Mol. Biol. 297:1015–1026(2000), where a thermostable subtilisin was evolved.

Standard cloning and protein or polypeptide isolation techniques can be used to arrive at the required sequence information. Parts of known sequences can be used as probes to isolate other homologues in other genera and strains. The nucleic acid sequence encoding a particular enzyme activity can be used to screen a Chrysosporium library for example. A person skilled in the art will realise which hybridisation conditions are appropriate. Conventional methods for nucleic acid hybridisation construction of libraries and cloning techniques are described in Sambrook et al (Eeds) (1989) In "Molecular Cloning. A Laboratory Manual" Cold Spring Harbor, Press Plainview, N.Y., and Ausubel et al (Eds) "Current Protocols in Molecular Biology" (1987) John Wiley and Sons, New York. The relevant information can also be derived from later handbooks and patents, as well as from various commercially available kits in the field.

In an alternative embodiment, said method comprises culturing a strain according to the invention under conditions permitting expression and preferably secretion of the protein or poly-peptide or precursor thereof and recovering the subsequently produced polypeptide and optionally subjecting the precursor to additional isolation and purification steps to obtain the polypeptide of interest. Such a method may suitably comprise a cleavage step of the precursor into the polypeptide or precursor of interest. The cleavage step can be cleavage with a Kex-2 like protease, any basic amino acid paired protease or Kex-2 for example when a protease cleavage site links a well secreted protein carrier and the polypeptide of interest. A person skilled in the art can readily find Kex-2-like protease sequences as consensus sequence details for such are available and a number of alternatives have already been disclosed e.g. furin.

Suitably in a method for production of the polypeptide according to any of the embodiments of the invention the cultivation occurs at pH higher than 5, preferably 5–10, more preferably 6–9. Suitably in such a method the cultivation occurs at a temperature between 25–43° C., preferably 30–40° C. The Chrysosporium strain used in the method according to the invention is quite suitably a recombinant Chrysosporium strain according to any of the embodiments disclosed. The method according to the invention in such a case can further be preceded by the step of production of a recombinant Chrysosporium strain according to the invention. The selection of the appropriate conditions will depend on the nature of the polypeptide to be expressed and such selection lies well within the realm of normal activity of a person skilled in the art.

The method of production of a recombinant Chrysosporium strain according to the invention is also part of the subject invention. The method comprises stably introducing a nucleic acid sequence encoding a heterologous or homologous polypeptide into a Chrysosporium strain, said nucleic acid sequence being operably linked to an expression regulating region, said introduction occurring in a manner known per se for transforming filamentous fungi. As stated above numerous references hereof are available and a small selection has been cited. The information provided is sufficient to enable the skilled person to carry out the method without undue burden. The method comprises introduction of a nucleic acid sequence comprising any of the nucleic acid elements described in the various embodiments of the recombinant Chrysosporium according to the invention as such or in combination.

By way of example the introduction can occur using the protoplast transformation method. The method is described in the examples. Alternative protoplast or spheroplast transformation methods are known and can be used as have been described in the prior art for other filamentous fungi. Details of such methods can be found in many of the cited references and are thus incorporated by reference. A method according to the invention suitably comprises using a non-recombinant strain of Chrysosporium according to the invention as starting material for introduction of the desired sequence encoding the polypeptide of interest.

The subject invention also covers a method of producing Chrysosporium enzyme, said method comprising culturing a Chrysosporium strain according to any of the embodiments of the invention as described above in or on a cultivation medium at pH higher than 5, preferably 5–10, more preferably 6–9, suitably 6–7.5, 7.5–9 as examples of neutral and alkaline pH ranges.

The subject invention also covers such a method using a cultivation medium at a temperature between 25–43° C., preferably 30–40° C. The combination of preferred pH and temperature is an especially preferred embodiment of the method of producing Chrysosporium enzyme according to the invention.

More in general the invention further covers a method of producing enzymes exhibiting neutral or alkaline optimal activity and/or stability, preferably alkaline optimal activity and/or stability. The preferred ranges vis-à-vis pH and optimal activity as well as assays with which to determine such have been provided elsewhere in the description. The enzyme should be selected from carbohydrate-degrading enzymes, proteases, other hydrolases, oxidoreductases, and transferases, as described above, said method comprising cultivating a host cell transformed or transfected with the corresponding enzyme-encoding nucleic acid sequence. Suitably such an enzyme will be a Chrysosporium enzyme. A suitable method such as this comprises production specifically of cellulase, xylanase, pectinase, lipase and protease, wherein cellulase and xylanase cleave -1,4-bonds and cellulase comprises endoglucanase, cellobiohydrolase and -glucosidase. The method according to the invention can comprise cultivating any Chrysosporium host according to the invention comprising nucleic acid encoding such aforementioned enzymes. Suitably the production of non-recombinant Chrysosporium hosts according to the invention is directed at production of carbohydrate degrading enzymes, hydrolases and proteases. In such a case the enzyme is suitably other than a cellulase. Suitable examples of products to be produced are given in Tables A and B. Methods of isolating are analogous to those described in WO 98/15633 and are incorporated by reference.

The enzymes produced by Chrysosporium strains according to the invention are also covered by the invention. Enzymes of Chrysosporium origin as can be isolated from non-recombinant Chrysosporium strains according to the invention are also covered. They exhibit the aforementioned stability, activity characteristics. Suitably they are stable in the presence of LAS. In particular proteases with pI 4–9.5, proteases with a MW of 25–95 kD, xylanases with pI between 4.0 and 9.5, xylanases with MW between 25 and 65 kD, endoglucanases with a pI between 3.5 and 6.5, endoglucanases with MW of 25–55 kDa, β-glucosidases, α,β-galactosidases with a pI of 4–4.5, β-glucosidases, α,β-galactosidases with a MW of 45–50 kDa, cellobiohydrolases of pI 4–5, cellobiohydrolases of MW 45–75 kDa, e.g. a MW of 55 kD and pI 4.4, polygalacturonases, with a pI of 4.0–5.0 polygalacturonase of 60–70 kDa, e.g. 65 kDa, esterases with a pI 4–5, and esterases with a MW of 95–105 kDa with the afore-mentioned stability, activity characteristics are claimed. The molecular weights (MW) are those determined by SDS-PAGE. The non-recombinant i.e. natively occurring enzyme is other than cellulase as disclosed in WO 98/15633. An enzyme as disclosed in WO 98/15633 is excluded. Enzymes according to the invention are represented by the enzymes of Table B. Enzymes with combinations of the pI values and molecular weights mentioned above are also covered.

The invention is also concerned with the (over)production of non-protein products by the mutant (recombinant) strains of the invention. Such non-protein products include primary metabolites such as organic acids, amino acids, and secondary such as antibiotics, e.g. penicillins and cephalo-sporins, and other therapeutics. These products are the result of combinations of biochemical pathways, involving several fungal genes of interest. Fungal primary and secondary metabolites and procedures for producing these metabolites in fungal organisms are well known in the art. Examples of the production of primary metabolites have been described by Mattey M., The Production of Organic Acids, *Current Reviews in Biotechnology*, 12, 87–132 (1992). Examples of the production of secondary metabolites have been described by Penalva et al. The Optimization of Penicillin Biosynthesis in Fungi, *Trends in Biotechnology* 16,483–489 (1998).

EXAMPLES

Examples of Biomass and Viscosity Determinations

The following operating parameter data ranges have been determined for fungal fermentations using three different fungal organisms. The three fungal organisms compared are: *Trichoderma longibrachiatum* (formerly *T. reesei*), *Aspergillus niger* and *Chrysosporium lucknowense* (UV18-25).

Viscosity

Viscosity is determined on a Brookfield LVF viscometer using the small sample adapter and spindle number 31.

Turn the water-circulating pump on 5 minutes prior to viscometer use to equilibrate the waterjacket. The water bath temperature should be 30° C.

Obtain a fresh sample of fermentation broth and place 10 ml of the broth in the small sample spindle. Select the spindle speed to give a reading in the range 10–80. Wait four (4) minutes and take the reading from the viscometer scale. Multiply the reading by the factor given below to get the viscosity in centipoise (cP).

| Spindle Speed | Multiplication Factor |
|---|---|
| 6 | 50 |
| 12 | 25 |
| 30 | 10 |
| 60 | 5 |

The following viscosity ranges have been determined for fermentations using the specified fungal organism using the above procedure:

|  | Viscosity in cP |
|---|---|
| T. longibrachiatum | 200–600 |
| A. niger | 1,500–2,000 |
| C. lucknowense (UV18-25) | LT 10 |

Biomass

Biomass is determined by the following procedure:

Preweigh 55 cm filter paper (Whatman 54) in an aluminium weighing dish.

Filter 5.0 ml whole broth through the 5.5 cm paper on a Buchner funnel, wash the filter cake with 10 ml deionised water, place the washed cake and filter in a weighing pan and dry overnight at 60° C. Finish drying at 100° C. for 1 hour, then place in desiccator to cool.

Measure the weight of dried material. Total biomass (g/l) is equal to the difference between the initial and finals weights multiplied by 200.

The following biomass ranges have been determined for fermentations using the specified fungal organism using the above procedure:

|  | Biomass in g/l |
|---|---|
| T. longibrachiatum | 2.5–5 |
| A. niger | 5–10 |
| C. lucknowense (UV18-25) | 0.5–1 |

Protein

Protein levels were determined using the BioRad Assay Procedure from Sigma Company. Protein levels were highest for the Chrysosporium.

The data presented above represent values determined 48 hours into the fermentation process until fermentation end; All values of Aspergillus and Trichoderma are for commercially relevant fungal organisms and reflect actual commercial data.

A fungal strain such as C. lucknowense (UV18-25) has the advantage that the low viscosity permits the use of lower power input and/or shear the in the fermentation to meet oxygen demands for those cases where shear stress on the product may be detrimental to productivity due to physical damage of the product molecule. The lower biomass production at high protein production indicates a more efficient organism in the conversion of fermentation media to product. Thus the Chrysosporium provides better biomass and viscosity data whilst also delivering at least as much protein, and in fact a lot more protein than the two commercially used systems which obviously are better than for typically deposited Aspergillus or Trichoderma reesei strains in general public collections.

The high protein production with low biomass concentration produced by C. lucknowense (UV18-25) would allow development of fermentation conditions with higher multiples of increase in biomass, if increasing biomass results in increased productivity, for the desired product before reaching limiting fermentation conditions. The present high levels of biomass and viscosity produced by the T. longibrachiatum and A. niger organisms restrict the increase of biomass as the present levels of biomass and viscosity are near limiting practical fermentation conditions.

Examples of Transformation Comparing Chrysosporium, Trichoderma and Tolypocladiumgeodes Two untransformed Chrysosporium C1 strains and one Trichoderma reesei reference strain were tested on two media (Gs pH 6,8 and Pridham agar, PA, pH 6,8). To test the antibiotic resistance level spores were collected from 7 day old PDA plates. Selective plates were incubated at 32° C. and scored after 2,4 and 5 days. It followed that the C-1 strains NG7C-19 and UV18-25 clearly have a low basal resistance level both to phleomycin and hygromycin. This level is comparable to that for a reference T. reesei commonly used laboratory strain. Thus there is clear indication these two standard fungal selectable markers can be used well in Chrysosporium strains. Problems with other standard fungal selectable markers should not be expected.

Selection of Sh-ble (phleomycin-resistance) transformed Chrysosporium strains was succesfully carried out at 50 μg/ml. This was also the selection level used for T. reesei thus showing that differential selection can be easily achieved in Chrysosporium. The same comments are valid for transformed strains with hygromycin resistance at a level of 150 μg/ml.

TABLE C

|  | Gs (pH 6.8) | | | Pridham Agar (PA,pH 6.8) | | |
|---|---|---|---|---|---|---|
|  | NG7C-19 | UV18-25 | T.r.11D5 | NG7C-19 | UV18-25 | T.r.11D5 |
| Phleomycin | 7.5 μg/ml | 10 μg/ml | 5–7.5 μg/ml | 2.5 μg/ml | 10 μg/ml | 2.5 μg/ml |
| Hygromycin | 7.5–10 μg/ml | 10 μg/ml | 10 μg/ml | 15 μg/ml | 25 μg/ml | 15 μg/ml |

The protoplast transformation technique was used on Chrysosporium based on the most generally applied fungal transformation technology. All spores from one 90 mm PDA plate were recovered in 8 ml IC1 and transferred into a shake flask of 50 ml IC1 medium for incubation for 15 hours at 35° C. and 200 rpm. After this the culture was centrifuged, the pellet was washed in MnP, brought back into solution in 10 ml MnP and 10 mg/ml Caylase $C_3$ and incubated for 30 minutes at 35° C. with agitation (150 rpm).

The solution was filtered and the filtrate was subjected to centrifugation for 10 minutes at 3500 rpm. The pellet was washed with 10 ml MnPCa$^{2+}$. This was centrifuged for 10 minutes at 25° C. Then 50 microlitres of cold MPC was added. The mixture was kept on ice for 30 minutes whereupon 2.5 ml PMC was added. After 15 minutes at room temperature 500 microlitres of the treated protoplasts were mixed to 3 ml of MnR Soft and immediately plated out on a MnR plate containing phleomycin or hygromycin as selection agent. After incubation for five days at 30° C. transformants were analysed (clones become visible after 48 hours). Transformation efficiency was determined using 10 microgrammes of reference plasmid pAN8-1[19]. The results are presented in the following Table D.

TABLE D

| Transformation efficiency (using 10 g of reference plasmid pAN8-1) | | | |
| --- | --- | --- | --- |
| | T. reesei | NG7C-19 | UV18-25 |
| Viability | $10^6$/200 µl | 5 $10^6$/200 µl | 5 $10^6$/200 µl |
| Transformants Per 200 µl | 2500 | $10^4$ | $10^4$ |
| Transformants per $10^6$ viable cells | 2500 | 2000 | 2000 |

The results show that the Chrysosporium transformants viability is superior to that of Trichoderma. The transformability of the strains is comparable and thus the number of transformants obtained in one experiment lies 4 times higher for Chrysosporium than for *T. reesei*. Thus the Chrysosporium transformation system not only equals the commonly used *T. reesei* system, but even outperforms it. This improvement can prove especially useful for vectors that are less transformation efficient than pAN8-1. Examples of such less efficient transformation vectors are protein carrier vectors for production of non-fungal proteins which generally yield 10 times fewer transformants.

A number of other transformation and expression vectors were constructed with homologous Chrysosporium protein encoding sequences and also with heterologous protein encoding sequences for use in transformation experiments with Chrysosporium. The vector maps are provided in the FIGS. 6–11.

The homologous protein to be expressed was selected from the group of cellulases produced by Chrysosporium and consisted of endoglucanase 6 which belongs to family 6 (MW 43 kDa) and the heterologous protein was endoglucanase 3 which belongs to family 12 (MW 25 kDa) of Penicillium.

pF6g comprises Chrysosporium endoglucanase 6 promoter fragment linked to endo-glucanase 6 signal sequence in frame with the endoglucanase 6 open reading frame followed by the endoglucanase 6 terminator sequence. Transformant selection is carried out by using cotransformation with a selectable vector.

pUT1150 comprises *Trichoderma reesei* cellobiohydrolase promoter linked to endoglucanase 6 signal sequence in frame with the endoglucanase 6 open reading frame followed by the *T. reesei* cellobiohydrolase terminator sequence. In addition this vector carries a second expression cassette with a selection marker i.e. the phleomycin resistance gene (Sh-ble gene).

pUT1152 comprises *Aspergillus nidulans* glyceraldehyde-3-phosphate dehydrogenase A promoter linked to endoglucanase 6 signal sequence in frame with the endoglucanase 6 open reading frame followed by the *A. nidulans* anthranilate synthase (trpC) terminator sequence. In addition this vector carries a second expression cassette with a selection marker i.e. the phleomycin resistance gene (Sh-ble gene).

pUT1155 comprises *A. nidulans* glyceraldehyde-3-phosphate dehydrogenase A promoter linked to *Trichoderma reesei* cellobiohydrolase signal sequence in frame with the carrier protein Sh-ble which in turn is linked in frame to the endoglucanase 6 open reading frame followed by the *A. nidulans* trpC terminator sequence. This vector uses the technology of the carrier protein fused to the protein of interest which is known to very much improve the secretion of the protein of interest.

pUT1160 comprises *Aspergillus nidulans* glyceraldehyde-3-phosphate dehydrogenase A promoter linked to *Trichoderma reesei* cellobiohydrolase signal sequence in frame with the carrier protein Sh-ble which in turn is linked in frame to the endoglucanase 3 open reading frame of Penicillium followed by the *A. nidulans* trpC terminator sequence.

pUT1162 comprises *Trichoderma reesei* cellobiohydrolase promoter linked to endo-glucanase 3 signal sequence in frame with the endoglucanase 3 open reading frame of Penicillium followed by the *T. reesei* cellobiohydrolase terminator sequence. In addition this vector carries a second expression cassette with a selection marker i.e. the phleomycin resistance gene (Sh-ble gene).

Further examples of expression systems include a Chrysosporium endoglucanase 3 promoter fragment linked to endoglucanase 3 signal sequence in frame with the endoglucanase 3 open reading frame followed by the endoglucanase 3 terminator sequence. Transformant selection is carried out by using cotransformation with a selectable vector.

Another example is a *Chrysosporium lucknowense* cellobiohydrolase promoter linked to Penicillium endoglucanase 3 signal sequence in frame with the Penicillium endoglucanase 3 open reading frame followed by the Chrysosporium cellobiohydrolase terminator sequence. In addition this vector carries a second expression cassette with a selection marker i.e. the aceetamidase S gene (AmdS gene).

A further example comprises *Chrysosporium glyceraldehyde*-3-phosphate dehydrogenase 1 promoter linked to the *Aspergillus niger* glucoamylase signal sequence and the glucoamylase open reading frame fused to the human Interleukine 6 open reading frame. In addition this vector carries a second expression cassette with a selection marker i.e. the AmdS gene.

A still further example is a Aspergillus nidulans glyceraldehyde-3-phosphate dehydrogenase A promoter linked to the endoglucanase 5 open reading frame followed by a Aspergillus nidulans terminator sequence.

TABLE E

Comparative transformations

| Vector | Strain | Transformation | No of transf. | Tested in liquid culture |
|---|---|---|---|---|
| PUT1150 | UV18-25 | selection phleo | 285 | 5 |
| | T. geodes | selection phleo | 144 | 5 |
| PUT1152 | UV18-25 | cotransformationpAN8.1 | 398 | 5 |
| | T. geodes | cotransformationpAN8.1 | 45 | 4 |
| PF6g | UV18-25 | cotransformationpAN8.1 | 252 | 6 |
| | T. geodes | cotransformationpAN8.1 | 127 | 5 |
| PUT1162 | UV18-25 | selection phleo | >400 | |
| | T. geodes | Not done yet | | |

Table E shows the results of transformation of both Chrysosporium UV18-25 and *Tolypocladium geodes*. The transformation protocol used is described in the section for heterologous transformation.

Examples of Heterologous and Homologous Expression of Chrysosporium Transformants C1 strains (NG7C-19 and/or UV18-25) have been tested for their ability to secrete various heterologous proteins: a bacterial protein (*Streptoalloteichus hindustanus* phleomycin-resistanceprotein, Sh ble), a fungal protein (*Trichoderma reesei* xylanase II, XYN2) and a human protein (the human lysozyme, HLZ).

The details of the process are as follows:

[1] C1 secretion of Streptoalloteichushindustanus phleomycin-resistanceprotein (Sh ble).

C1 strains NG7C-19 and UV18-25 have been transformed by the plasmid pUT720 [1]. This vector presents the following fungal expression cassette:

*Aspergillus nidulans* glyceraldehyde-3-phosphate dehydrogenase (gpdA) promoter[2]

A synthetic *Trichoderma reesei* cellobiohydrolaseI (cbh1) signal sequence[1,3]

Streptoalloteichushindustanus phleomycin-resistancegene Sh ble[4]

*Aspergillus nidulans* tryptophan-synthase(trpC) terminator.[5]

The vector also carries the beta-lactamase gene (bla) and *E. coli* replication origin from plasmid pUC18[6]. The detailed plasmid map is provided in FIG. 2.

C1 protoplasts were transformed according to Durand et al.[7] adapted to C1 (media & solutions composition is given elsewhere): All spores from one 90 mm PDA plate of untransformed C1 strain were recovered in 8 mm IC1 and transferred into a shake flask with 50 ml IC1 medium for incubation 15 hours at 35° C. and 150 rpm. Thereupon, the culture was spun down, the pellet washed in MnP, resolved in 10 ml MnP+10 mg/ml Caylase $C_3$, and incubated 30 min at 35° C. with agitation (150 rpm). The solution was filtrated and the filtrate was centrifuged 10 min at 3500 rpm. The pellet was washed with 10 ml MnPCa$^{2+}$. This was spun down 10 min at 3500 rpm and the pellet was taken up into 1 ml MnPCa$^{2+}$. 10 μg of pUT720 DNA were added to 200 μl of protoplast solution and incubated 10 min at room temperature (~20° C.). Then, 50 μl of cold MPC was added. The mixture was kept on ice for 30 min whereupon 2.5 ml PMC was added. After 15 min at room temperature 500 μl of the treated protoplasts were mixed to 3 ml of MnR Soft and immediately plated out on a MnR plate containing phleomycin (50 μg/ml at pH6.5) as selection agent. After 5 days incubation at 30° C., transformants were analysed (clones start to be visible after 48 hours).

The Sh ble production of C1 transformants (phleomycin-resistant clones) was analysed as follows: Primary transformants were toothpicked to GS+phleomycin(5 μg/ml) plates and grown for 5 days at 32° C. for resistance verification. Each validated resistant clone was subcloned onto GS plates. Two subclones per transformant were used to inoculate PDA plates in order to get spores for liquid culture initiation. The liquid cultures in IC1 were grown 5 days at 27° C. (shaking 200 rpm). Then, the cultures were centrifuged (5000 g, 10 min.) and 500 μl of supernatant were collected. From these samples, the proteins were precipitated with TCA and resuspended in Western Sample Buffer to 4 mg/ml of total proteins (Lowry Method [8]). 10 μl (about 40 μg of total proteins) were loaded on a 12% acrylamide/SDS gel and run (BioRad Mini Trans-Blot system). Western blotting was conducted according to BioRad instructions (Schleicher & Schull 0.2 μm membrane) using rabbit anti-Sh ble antiserum (Cayla Cat. Ref. #ANTI-0010) as primary antibody. The results are shown in FIG. 1 and Table F:

TABLE F

Sh ble estimated production levels in C1

| | Estimated Sh ble quantity on the Western blot | Estimated Sh ble concentration in the production media |
|---|---|---|
| Untransformed NG7C-19 | Not detectable | |
| NG7C-19::720 clone 4-1 | 25 ng | 0.25 mg/l |
| NG7C-19::720 clone 5-1 | 25 ng | 0.25 mg/l |
| NG7C-19::720 clone 2-2 | 250 ng | 2.5 mg/l |
| Untransformed UV18-25 | Not detectable | |
| UV18-25::720 clone 1-2 | 500 ng | 5 mg/l |
| UV18-25::720 clone 3-1 | 250 ng | 2.5 mg/l |

These data show that:

1) The heterologous transcription/translation signals from pUT720 are functional in Chrysosporium.

2) The heterologous signal sequence of pUT720 is functional in Chrysosporium.

3) Chrysosporium can be used a host for the secretion of an heterologous bacterial protein.

[2] C1 secretion of the human lysozyme(HLZ).

C1 strains NG7C-19 and UV18-25 have been transformed by the plasmid pUT970G[9]. This vector presents the following fungal expression cassette:

*Aspergillus nidulans* glyceraldehyde-3-phosphatedehydrogenase (gpdA) promoter[2]

A synthetic *Trichoderma reesei* cellobiohydrolaseI (cbh1) signal sequence[1,3]

*Streptoalloteichus hindustanus* phleomycin-resistance gene Sh ble [4] used as carrier-protein[10]

*Aspergillus niger* glucoamylase (glaA2) hinge domain cloned from plasmid pAN56-2[11,12]

A linker peptide (LGERK) featuring a KEX2-like protease cleavage site[1]

A synthetic human lysozyme gene (hlz)[10]

*Aspergillus nidulans* tryptophan-synthase(trpC) terminator[5]

The vector also carries the beta-lactamase gene (bla) and *E. coli* replication origin from plasmid pUC18[6]. The detailed plasmid map is provided in FIG. 3.

C1 protoplasts were transformed with plasmid pUT970G following the same procedure already described in example 1. The fusion protein (Sh ble :: GAM hinge :: HLZ) is functional with respect to the phleomycin-resistance thus allowing easy selection of the C1 transformants. Moreover, the level of phleomycin resistance correlates roughly with the level of hlz expression.

The HLZ production of C1 transformants (phleomycin-resistant clones) was analysed by lysozyme-activity assay as follow: Primary transformants were toothpicked to GS+phleomycin (5 μg/ml) plates (resistance verification) and also on LYSO plates (HLZ activity detection by clearing zone visualisation[1, 10]). Plates were grown for 5 days at 32° C. Each validated clone was subcloned onto LYSO plates. Two subclones per transformant were used to inoculate PDA plates in order to get spores for liquid culture initiation. The liquid cultures in IC1 were grown 5 days at 27° C. (shaking 180 rpm). Then, the cultures were centrifuged (5000 g, 10 min.). From these samples, lysozyme activity was measured according to Mörsky et al. [13].

TABLE G

Active HLZ production levels in C1

| | Active HLZ concentration in culture media |
|---|---|
| Untransformed NG7C-19 | 0 mg/l |
| NG7C-19::970G clone 4 | 4 mg/l |
| NG7C-19::970G clone 5 | 11 mg/l |
| Untransformed UV18-25 | 0 mg/l |
| UV18-25::970G clone 1 | 8 mg/l |
| UV18-25::970G clone 2 | 4 mg/l |
| UV18-25::970G clone 3 | 2 mg/l |
| UV18-25::970G clone 2 | 2.5 mg/l |

These data show that:
1) Points 1 & 2 from example 1 are confirmed.
2) Sh ble is functional in Chrysosporium as resistance-marker.
3) Sh ble is functional in Chrysosporium as carrier-protein.
4) The KEX2-like protease cleavage site is functional in Chrysosporium (otherwise HLZ wouldn't be active).
5) Chrysosporium can be used as host for the secretion of a heterologous mammalian protein.

[3] C1 secretion of Trichoderma reesei xylanase II (XYN2).

C1 strain UV18-25 has been transformed by the plasmids pUT1064 and pUT1065.

pUT 1064 presents the two following fungal expression cassettes:

The first cassette allows the selection of phleomycin-resistanttransformants:
  *Neurospora crassa* cross-pathway control gene 1 (cpc-1) promoter[14]
  *Streptoalloteichus hindustanus* phleomycin-resistancegene Sh ble [4]
  *Aspergillus nidulans* tryptophan-synthase(trpC) terminator[5]

The second cassette is the xylanase production cassette:
  *T. reesei* strain TR2 cbh1 promoter[15]
  *T. reesei* strain TR2 xyn2 gene (including its signal sequence)[16]
  *T. reesei* strain TR2 cbh1 terminator[15]

The vector also carries an *E. coli* replication origin from plasmid pUC19[6]. The plasmid detailed map is provided in FIG. 4.

pUT1065 presents the following fungal expression cassette:
  *A. nidulans* glyceraldehyde-3-phosphatedehydrogenase (gpdA) promoter[2]
  A synthetic *T. reesei* cellobiohydrolaseI (cbh1) signal sequence[1,3]
  *S. hindustanus* phleomycin-resistancegene Sh ble [4] used as carrier-protein[10]
  A linker peptide (SGERK) featuring a KEX2-like protease cleavage site[1]
  *T. reesei* strain TR2xyn2 gene (without signal sequence)[16]
  *A. nidulans* tryptophan-synthase(trpC) terminator[5]

The vector also carries the beta-lactamase gene (bla) and an *E. coli* replication origin from plasmid pUC18[6]. The plasmid detailed map is provided in FIG. 5. C1 protoplasts were transformed with plasmid pUT1064 or pUT1065 following the same procedure already described in example 1. The fusion protein in plasmid pUT1065 (Sh ble :: XYN2) is functional with respect to the phleomycin-resistance thus allowing easy selection of the C1 transformants. Moreover, the level of phleomycin resistance correlates roughly with the level of xyn2 expression. In pUT1064, xyn2 was cloned with its own signal sequence.

The xylanase production of C1 transformants (phleomycin-resistant clones) was analysed by xylanase-activity assay as follow: Primary transformants were toothpicked to GS+phleomycin (5 μg/ml) plates (resistance verification) and also on XYLAN plates (xylanase activity detection by clearing zone visualisation[17]). Plates were grown for 5 days at 32° C. Each validated clone was subcloned onto XYLAN plates. Two subclones per transformant were used to inoculate PDA plates in order to get spores for liquid culture initiation. The liquid cultures in IC1+5 g/l KPhtalate were grown 5 days at 27° C. (shaking 180 rpm). Then, the cultures were centrifuged (5000 g, 10 min.). From these samples, xylanase activity was measured by DNS Technique according to Miller et al.[18]

TABLE H

Active XYN2 production levels in C1 (best producers)

| | Active xylanase II concentration in culture media | Xylanase II specific activity in culture media |
|---|---|---|
| Untransformed UV18-25 | 3.9 U./ml | 3.8 U./mg total prot. |
| UV18-25::1064 clone 7-1 | 4.7 U./ml | 4.7 U./mg total prot. |
| UV18-25::1064 clone 7-2 | 4.4 U./ml | 4.3 U./mg total prot. |
| UV18-25::1065 clone 1-1 | 29.7 U./ml | 25.6 U./mg total prot. |
| UV18-25::1065 clone 1-2 | 30.8 U./ml | 39.4 U./mg total prot. |

These data show that:
1) Points 1 to 4 from example 2 are confirmed.
2) C1 can be used as host for the secretion of a heterologous fungal protein.

[4] We also illustrate data from expression of transformed UV18-25 wherein the table I shows the results for the plasmids with which transformation was carried out. The Table shows good expression levels for endoglucanase and cellobiohydrolase using heterologous expression regulating sequences and signal sequences but also with homologous expression regulating sequences and signal sequences. The details of the various plasmids can be derived elsewhere in the description and from the figures. The production occurs at alkaline pH at a temperature of 35° C.

TABLE I

Expression data of transformed UV18-25 strain

| Culture | Total proteins mg/ml | CMCase u/ml | CMCase u/mg | β-glucanase u/ml | β-glucanase u/mg | pH value |
|---|---|---|---|---|---|---|
| *UV 18–25 | 100% | 100% | 100% | 100% | 100% | 7.90 |
| 1150–23 | 94% | 105% | 111% | 140% | 149% | 7.90 |
| –30 | 96% | 105% | 110% | 145% | 151% | 8.10 |
| 1152–3 | 94% | 112% | 120% | 147% | 156% | 7.85 |
| –4 | 100% | 105% | 105% | 132% | 132% | 7.90 |
| 1160–2 | 69% | 81% | 118% | 90% | 131% | 7.90 |
| –4 | 73% | 72% | 98% | 83% | 114% | 8.35 |
| –1 | 92% | 95% | 103% | 120% | 130% | 8.45 |
| 1162–1 | 102% | 105% | 103% | 145% | 142% | 8.20 |
| –11 | 112% | 109% | 98% | 115% | 103% | 8.20 |
| F6g–20 | 104% | 102% | 98% | 130% | 125% | 7.90 |
| –25 | — | — | — | — | — | — |

Culture conditions (shake flask): 88 h, 35° C., 230 rpm
*all above FIGS. are in relative % to parent UV18–25 strain Appendix to the Examples: Media

Transformation media:

Mandels Base:

| | |
|---|---|
| KH$_2$PO$_4$ | 2.0 g/l |
| (NH$_4$)$_2$SO$_4$ | 1.4 g/l |
| MgSO$_4$.7H$_2$O | 0.3 g/l |
| CaCl$_2$ | 0.3 g/l |
| Oligoelements | 1.0 ml/l |

MnP Medium:

| | |
|---|---|
| Mandels Base with Peptone | 1 g/l |
| MES | 2 g/l |
| Sucrose | 100 g/l |
| Adjust pH to 5 | |

MnR

MnP CA$^{2+}$:

| | |
|---|---|
| MnP + sucrose | 130 g/l |
| Yeast extract | 2.5 g/l |
| Glucose | 2.5 g/l |
| Agar | 15 g/l |

| | |
|---|---|
| MnP Medium + CaCl$_2$ 2H$_2$O 50 mM | |
| Adjust pH to 6.5 | |

MnR Soft: MnR with only 7.5 g/l of agar.

MPC:

| | |
|---|---|
| CaCl$_2$ | 50 mM pH 5.8 |
| MOPS | 10 mM |
| PEG | 40% |

For selection and culture

GS:

| | | |
|---|---|---|
| Glucose | 10 g/l | |
| Biosoyase | 5 g/l | [Merieux] |
| Agar | 15 g/l | pH should be 6.8 |

PDA:

| | | |
|---|---|---|
| Potato Dextrose Agar | 39 g/l | [Difco] pH should be 5.5 |

MPG:

| | |
|---|---|
| Mandels Base with K.Phtalate | 5 g/l |
| Glucose | 30 g/l |
| Yeast extract | 5 g/l |

The regeneration media (MnR) supplemented with 50 µg/ml phleomycin or 100–150 µg/ml hygromycin is used to select transformants. GS medium, supplemented with 5 µg/ml phleomycin is used to confirm antibiotic resistance.

PDA is a complete medium for fast growth and good sporulation. Liquid media are inoculated with 1/20th of spore suspension (all spores from one 90 mm PDA plate in 5 ml 0.1% Tween). Such cultures are grown at 27° C. in shake flasks (200 rpm).

Isolation and Characterisation of C1 Proteins

The process for obtaining various proteins is described as are a number of characteristics of the proteins. Tables A and B and FIG. 36 provide details of purification scheme and activities. Isolation occurs from the Chrysosporium culture filtrate using DEAE-Toyopearl ion exchange chromatography analogously to the method described in WO 98/15633, which is incorporated herein by reference. The non-bound fraction (F 60-31 CF) obtained from this chromatography was purified using Macro Prep Q™ ion exchange chromatography after equilibration to pH 7.6. The non-bound fraction (NBNB) was pooled and bound proteins were eluted in 0–1 M NaCl gradient. The NBNB fraction provided major protein bands of 19, 30, 35 and 46 kD and a minor one of 51 kD. In 0–1 M NaCl gradient protein peaks were eluted from various fractions. 39–41 included 28, 36 and 60 kD proteins, 44–48 included 28, 45 and 66 kD as major protein bands with 33, 36, 55, 60 and 67 kD proteins, the 49–51 fraction gave 30, 36, 56 and 68 kD proteins and the 52–59 fraction included, major 33 and 55 kD proteins and minor 28 and 36 kD proteins. The pooled NBNB fraction was further purified by hydrophobic chromatography on Phenyl Superose™. The NBNB fraction was equilibrated with 0.03M Na-phosphate buffer pH 7.0 containing 1.2 M (NH$_4$)$_2$SO$_4$ and applied to a column. Adsorbed proteins were eluted in 1.2–0.6 M (NH$_4$)$_2$SO$_4$ gradient. Thus homogeneous xylanase with MW 30 and 51 kD and pI 9.1 and 8.7 respectively were obtained as was a 30 kD protease with pI 8.9.

The xylanases did not possess MUF cellobiase activity and are thus true xylanases. The alkaline 30 kD xylanase (pI 9.1) possessed high activity within a very broad pH range from 5–8 maintaining 65% of maximum activity at pH 9–10; it is a member of the xylanase F family; its partial nucleotide and amino acid sequences are depicted in SEQ ID No. 7. The partial amino acid sequence depicted corresponds to about amino acids 50–170 from the N terminus of the mature protein. Xylanases according to invention have at least 60%, preferably at least 70%, most preferably at least 80% sequence identity of the partial amino acid sequence of SEQ ID No. 7. The corresponding xylanase promoter, which is a preferred embodiment of the invention, can be identified using the partial nucleotide sequence of SEQ ID No. 7. The 51 kD xylanase (pI 8.7) possessed maximum activity at pH 6 and retained at least 70% of its activity at pH 7.5 and it retained at least 50% of its activity at pH 8.0. It was not very stable with only 15% activity at pH 5.5 and 4% at pH 7.5. The Michaelis constant toward birch xylan was 4.2 g/l for 30 kD xylanase and 3.4 g/l for 51 kD xylanase. Temperature optimum was high and equal to 70° C. for both xylanases.

The 30 kD protease activity measured towards proteins of the NBNB fraction appeared to be equal to $0.4 \times 10_{-3}$ units/ml at 50° C. and pH 7.90 kD. The fraction exhibited activity toward dyed casein of 0.4 arbitrary units/mg (pH 7). Addition of urea as chaotropic agent resulted in 2–3 times increase of protease activity. The effect of the protease on xylanase activity was significant. Only 30% xylanase activity remained at pH 10.3 and 50° C. after 30 minutes of incubation. At pH 8 95% of the xylanase activity remained. LAS addition resulted in a dramatic decrease of xylanase activity at pH 8 and 10.3 with only 50% xylanase activity after 10 minutes of incubation with or without protease inhibitor PMSF. The 30 kD protease was alkaline with pH optimum at pH 10–11. The activity is inhibited by phenylmethylsulfonyl fluoride (PMSF) and not by iodoacetic acid, pepstatin A and EDTA which characterises it as a serine type protease. The protease is not active towards C1 proteins at neutral pH and 50° C. without chaotropic agents. Increase of pH and the addition of chaotropic agents such as LAS, SDS and urea significantly increase proteolysis.

The 39–41 fraction was purified by hydrophobic chromatography on plenol superose. Fractions were equilibrated with 0.03M Na phosphate buffer pH 7.2 containing 1.5 M $(NH_4)_2SO_4$ and applied to a column. Adsorbed proteins were eluted in 1.5–0 M $(NH_4)_2SO_4$ gradient. Thus homogenous xylanase with MW 60 kD and pI 4.7 was obtained. This xylanase possessed activities towards xylan, MUF-cellobioside, MUF-xyloside and MUF-lactoside. This xylanase probably belongs to family 10 (family F). This xylanase was stable at pH from 5 to 8 during 24 hours and retained more than 80% activity at 50° C. It retained 70% activity at pH 5–7 at 60° C. It kept 80% activity during 5 hours and 35% during 24 hours at 50° C. and pH 9. At pH 10 60% activity was retained at 50° C. and 0.5 hours of incubation. After 5 hours of incubation at pH 8 and 60° C. 45% activity was found decreasing to 0 after 24 hours. It had a pH optimum within the pH range of 6–7 and kept 70% activity at pH 9 and 50% of its activity at pH 9.5. The Michaelis constant toward birch xylan was 0.5 g/l. Temperature optimum was high and equal to 80° C.

Fraction 44–48 was then purified by chromatofocusing on Mono P. A pH gradient from 7.63–5.96 was used for the elution of the proteins. As a result 45 kD endoglucanase was isolated with a pI of 6. The 45 kD endo had maximum activity at pH 5 toward CMC and at pH 5–7 toward RBB-CMC. The 45 kD endo retained 70% of its maximal activity toward CMC at pH 6.5 and 70% of its maximal activity toward RBB-CMC was retained at pH 7.0; 50% of its maximal activity toward CMC was retained at pH 7 and 50% of its maximal activity toward RBB-CMC was retained at pH 8. The Michaelis constant toward CMC was 4.8 g/l. Temperature optimum was high and equal to 80° C. Other proteins 28, 33, 36, 55, 60 and 66 kD were eluted mixed together.

Fraction 52–58 was purified by chromatofocusing on Mono P too with a pH gradient 7.6–4.5. Individual 55 kD endoglucanase with pI 4.9 was obtained. The 55 kD endo was neutral. It has a broad pH optimum from 4.5–6 and 70% activity was retained at pH 7.0 both for CMC and RBB-CMC and 50% activity was retained at pH 8 for both CMC and RBB-CMC. The Michaelis constant toward CMC was 1 g/l. Temperature optimum was high and equal to 80° C. A number of fractions also held proteins with MW of 28, 33 and 36 kD.

45, 48 and 100 kD proteins were isolated from bound DEAE Toyopearl fraction of F 60-8 UF conc of Chrysosporium culture from fractions 50–53 using Macro Prep Q chromatography.

Fraction 50–53 was equilibrated with 0.03 M imidazole HCL buffer, pH 5.75 and was applied to a column and the adsorbed proteins were eluted in 0.1–0.25 M NaCl gradient for 4 h. As a result 45 kD (pI 4.2), 48 kD (pI 4.4) and 100 kD (pI 4.5) proteins were isolated in homogenous states.

The 45 kD is supposedly a alpha beta-galactosidase by virtue of its activity toward p-nitrophenyl alpha-galactoside and p-nitrophenyl beta-galactoside. The pH optimum was 4.5 70% activity was maintained at pH 5.7 and 50% of its activity was retained at pH 6.8. The temperature optimum was 60° C.

The 48 kD protein was a cellobiohydrolase having high activity toward p-nitrophenyl beta-glucoside and also activities toward MUF cellobioside, MUF lactoside and p-nitrophenyl butyrate. The 48 kD protein had a pH optimum of 5 toward CMC and 5–6 toward RBB-CMC.

The 100 kD protein with pI 4.5 possessed activity only toward p-nitrophenyl butyrate. It is probably an esterase but is not a feruloyl esterase as it had no activity against methyl ester of ferulic acid. It had neutral/alkaline pH optimum (pH 8–9) and optimal temperature of 55–60° C.

The 90 kD protease with pI 4.2 was isolated from the bound fraction and the activity measured towards proteins of the NBNB fraction appeared to be equal to $12 \times 10_{-3}$ units/ml at 50° C. and pH 7.90 kD. The fraction exhibited activity toward dyed casein of 0.01 arbitrary units/mg (pH 7). Addition of urea as chaotropic agent resulted in 2–3 fold increase of protease activity as did addition of LAS at both pH 7 and 9 (50° C.). The 90 kD protease was neutral with pH optimum at pH 8. The activity is inhibited by phenylmethylsulfonyl fluoride (PMSF) and not by iodoacetic acid, pepstatin A and EDTA which characterises it as a serine type protease.

Also isolated from the bound fraction were 43 kD endoglucanase with pI 4.2 (fraction 33–37) and 25 kD endoglucanase with pI 4.1 (fraction 39–43), 55 kD cellobiohydrolase with pI 4.9 (fraction 39–43) and 65 kD polygalacturonase with pI 4.4 (fraction 39–43). The endoglucanases did not possess activity towards avicel or MUF cellobioside and possessed high activity toward MC, RBB-CMC, CMC41, beta-glucan and endoglucanase. The 25 kD endo did not produce glucose from CMC and the 43 kD endo did. No glucose was formed from avicel. The pH optimum for the 43 kD protein was 4.5 with 70% maximum activity maintained at pH 7.2 and 50% at pH 8. The 43 kD endo kept 70% activity at pH 5 and 6 during 25 hours of incubation. It kept only 10% at pH 7 during this incubation period. The 25 kD endo had acid pH optimum of activity at pH 5 toward CMC and broad pH optimum of activity toward RBB-CMC with 70% of the maximum activity being kept at pH 9 and with 50% of the maximum activity being at pH 10. It kept 100% activity at pH 5 and 6 and 80% at pH 7, 8, 8.6 and 9.6 during 120 hours of incubation. The 25 kD endo had a temperature optimum of activity at 70° C. The 43 kD endo had a temperature optimum of activity at 60° C. The Michaelis constants towards CMC were 62 and 12.7 g/l for 25 and 43 kD endo respectively. The poly-galacturonase is a pectinase. The Michaelis constant toward PGA was 3.8 g/l. The pH optimum of PGU activity is within pH range 5–7 and T optimum within 50–65° C.

Genes encoding *C. lucknowense* proteins were obtained using PCR and characterised by sequence analysis. The corresponding full genes were obtained by screening (partial) gene libraries using the isolated PCR fragments. The full gene of the 43 kD endoglucanase (EG6, Family 6) of the C1 strain has been cloned, sequenced and analysed (including 2.5 kb promoter region and 0.5 kb terminator region). Its nucleotide and amino acid sequences are depicted in SEQ ID No. 6. Predicted molecular weight of the mature protein is 39,427 Da and predicted pI is 4.53, which values correspond well with the measured values. Protein alignment analysis with other glycosyl hydrolases of the family 6.2 shows that C1-EG6 does not include a cellulose-binding domain (CBD) Homology analysis using SwissProt SAMBA software (Smith & Waterman algorithm, Gap penalty 12/2, alignment 10, Blosum62 matrix) shows that C1-EG6 has 51.6% identity with *Fusarium oxysporum* EG-B (over 376 amino acids), 51.0% identity with *Agaricus*

*bisporus* CBH3 (over 353 amino acids), and 50.7% identity with *Trichoderma reesei* CBH2 (over 367 amino acids). The putative signal sequence runs Met 1 to Arg 28. The promoter contains several potential CreA binding sites, so it is very likely that this promoter would be subject to glucose repression in a fungal strain with working CreA regulation.

Similarly, the full gene of the 25 kD endoglucanase (EG5, Family 45) of the C1 strain has been cloned, sequenced and analysed (including 3.3 kb promoter region and 0.7 kb terminator region). The nucleotide and amino acid sequences are depicted in SEQ ID No. 5. Predicted molecular weight of the mature protein is 21,858 Da and predicted pI is 4.66, which values correspond well with the measured values. This is the smallest fungal endoglucanase known to date. Protein alignment analysis with other glycosyl hydrolases of the family 45 shows that C1-EG5 does not include a cellulose-binding domain (CBD), nor a cohesin/dockerin domain. Homology analysis using NCBI-BLASTP2 software (Gap penalty 11/1, alignment 10, Blosum62 matrix) shows that the closest homologous protein to C1-EG5 is *Fusarium oxysporum* EG-K with 63% identity. The putative signal sequence runs Met 1 to Ala 18. The promoter contains many potential CreA binding sites, so it is very likely that this promoter would be subject to glucose repression in a fungal strain with working CreA regulation.

Furthermore, an additional endoglucanase was found by PCR based on family 12 cellulases homology analysis. The partial nucleotide and amino acid sequence of this additional endoglucanase (EG3, Family 12) is given in SEQ ID No. 8.

The 55 kD protein was a cellobiohydrolase (referred to herein as CBH1) with activity against MUF-cellobioside, MUF lactoside, FP and avicel, also against p-nitrophenyl -glucoside, cellobiose and p-nitrophenyl lactoside. Its activity toward MUF cellobioside is inhibited by cellobiose. The inhibition constant 0.4 mM was determined. The Michaelis constant toward MUF cellobioside was 0.14 mM, toward MUF lactoside was 4 mM and toward CMC was 3.6 g/l. The pH optimum is rather broad from 4.5 to 7. 50% of maximum activity toward CMC and 80% activity toward RBB-CMC is kept at pH 8. 70–80% activity within pH 5–8 is kept during 25 hours of incubation. The temperature optimum is 60–70° C. CBH1 is probably a member of the cellobiohydrolase family 7; its partial nucleotide and amino acid sequences are depicted in SEQ ID No. 9. The partial amino acid sequence depicted corresponds to about amino acids 300–450 from the N terminus of the mature protein. A cellobiohydrolase according to the invention has at least 60%, preferably at least 70%, most preferably at least 80% sequence identity of the partial amino acid sequence of SEQ ID No. 9. The corresponding CBH promoter, which is a preferred embodiment of the invention, can be identified using the partial nucleotide sequence of SEQ ID No. 9. A synergistic effect was observed between 25 kD endo and 55 kD CBH during avicel hydrolysis. Synergism coefficient was maximal at the ratio of 25 kD endo to 55 kD CBH 80:20. The $K_{syn}$ was 1.3 at its maximum.

The expression level of five main Chrysosporium genes was studied by Northern analysis. Various strains of *C. lucknowense* were grown in rich medium containing pharmedia with cellulose and lactose (medium 1) or rich medium containing pharmedia and glucose (medium 2) at 33 C. After 48 h, mycelium was harvested and RNA was isolated. The RNA was hybridised with 5 different probes: EG5, EG6, EG3, XylF and CBH. After exposure, the Northern blots were stripped and hybridised again with a probe for ribosomal L3 as a control for the amount of mRNA on the blot. Most strains showed very high response for CBH and high response for XylF in medium 1; in medium 2, half of the strain showed high response for all genes, and the other half showed low response. The order of expression strength was deducted from these data as CBH>XylF>EG5>EG3>EG6.

Tables A and B and FIG. 36 illustrate the details of the above.

Advanced Isolation and Characterisation of C1
Genes and Gene Expression Sequences of CBH1,
XYL1, EG3 and GPD Construction of a BlueSTAR Gene Library of UV18-25

Chromosomal DNA of UV18-25 was partially digested with Sau3A, fragments of 12–15 kb were isolated and ligated in a BamHI site of cloning vector BlueSTAR. Packaging of 20% of the ligation mixture resulted in a gene library of $4.6 \times 10^4$ independent clones. This library was multiplied and stored at 4° C. and −80° C. The rest of the ligation mixture was also stored at 4° C.

Screening the Gene Library of UV18-25 for Isolation of the Genes for cbh1, eg3, xyl1 and gpd1

For the isolation of the different genes, in total $\pm 7.5 \times 10^4$ individual BlueSTAR phages per probe were hybridized in duplo. Hybridisation was carried out with the PCR fragments of cbh1, eg3 and xyl1 (as described in PCT/NL99/00618) at homologous conditions (65° C.; 0.2×SSC) and with the gpd1 gene of *A. niger* at heterologous conditions (53° C.; 0.5×SSC). The number of positive signals is given in Table K. The positive clones were rescreened and for each clone two individual phages were used for further experiments. DNA of the different clones was analysed by restriction analysis to determine the number of different clones isolated from each gene (results are given in Table K).

As for each of the 4 genes, 4–6 different clones were isolated, we conclude that the primary gene library (±4–5× $10^4$ clones) represents about 5× genome of UV18-25. From this result we conclude that the complete genome of UV18-25 is represented in $9 \times 10^3$ clones. Based on an average genomic insert of 13 kb, this would indicate a genome size of ±120 Mb, which is 3 times the size of the Aspergillus genome.

PCR reactions with specific primers for the gene present on the plasmid (based on previous sequence determination from the isolated PCR fragments) and the T7 and T3 primer present in the polylinker of pBlueSTAR we were able to determine the location of the genes in a number of clones. From each gene a plasmid was used for sequence determination of the gene.

Sequence Analysis of the Cloned Genes

For the cbh1, xyl1, eg3 and the gpd1 gene, the results of the sequence determination are represented in SEQ ID No's 1, 2, 3 and 4 respectively. Also the deduced amino acid sequences of the proteins are represented in these SEQ ID No's 1–4. Some properties of the proteins are given in Table L. It should be mentioned that the position of the start of the translation and the introns is based on homology with genes from the same family (i.e. paper genetics).

CBH1

From the amino acid sequences of CBH1, we concluded that the protein is about 63 kD in size and that a cellulose binding domain (CBD) is present at the C-terminal part of the protein. Interestingly, no evidence was found for the presence of a CBD in the isolated 55 kD major protein. However, the presence of the isolated peptides from this 55 kD major protein in the encoded CBH1 protein (SEQ ID No. 1), confirms that the 55 kD protein is encoded by the cloned gene. A possible explanation of these results is that the 55 kD protein is a truncated version of the CBH1 protein lacking the CBD.

Xyl1

From the amino acid sequences of xyl1 we conclude that also here a CBD is present, in this protein at the N-terminal side. In the literature only two more xylanases with a CBD are known (*Fusarium oxysporum* and *Neocallimastix patriciarum*). The estimated size of the Xyl1 protein is 43 kD and several peptides isolated from a 30 kD xylanase originate from this protein (SEQ ID No. 2). It should be noted that a considerable number of the isolated peptides could not be found in the encoded sequence. This could indicate that alternative xylanase proteins are present in UV18-25. In previous analysis, no evidence was found for the presence of CBD in this 30 kD protein. Also from these results we hypothesized that the CBD of the protein is cleaved of by proteolysis. This hypothesis will be analysed further (by determination of activities, N-terminal sequences and sizes of the different proteins in the different C1 strains: C1 wild type, NG7C, UV13-6, UV18-25 and protease mutants of UV18-25) Also the effect of the presence or absence of the CBD on enzymatic activities has to be analysed in detail further. Overexpression of the full length genes in various C1 hosts may be considered. The presence of a cellulose binding domain (CBD) is a particular feature of this enzyme; the only other known family 10 glycolytic enzyme (xylanase) having a CBD is the *Fusarium oxysporum* XylF. The invention thus pertains to *fungal xylanases* having a CBD other than the *Fusarium oxysporum* xylanase.

EG3

From the amino acid sequence of EG3 it could be concluded that EG3 is a family 12 protein. The gene encodes a preproprotein with a dibasic (K-R) propeptide processing site. The C1EG3 protein is 62% similar and 54% identical to the B1 EG3 protein. One putative glycosylation site is present at the C-terminal part of the protein (SEQ ID No. 3).

Gpd1

The DNA sequence of the C-terminal part of the gpd1 gene is not determined, since we are primarily interested in the promoter sequences of this gene (SEQ ID No. 4).

The proteins XYL1 and EG3 of *C. lucknowense* are 54–70% identical to their closest homologue in the Genbank DATABASE (Table L). Notable is the strong homology of the CBH1 and the EG5 proteins to their related *Humicola grisea* proteins (74–82% identical). Interestingly the closest related proteins to the EG6 protein are only 46–48% identical.

Also notable is that in most cases the closest homologues originate from Fusarium, Humicola or other Pyrenomycetous fungi (Table L), whereas Chrysosporium belongs to the Plectomycetous fungi according to the NCBI taxonomy database (Table L).

TABLE K

Screening of $7.5 \times 10^4$ phages of the gene library of UV18–25 with PCR fragments of UV18–25 for the cbh1 gene, the eg3 gene and the xyl1 gene (homologous conditions) and with the gpdA gene of *A. niger* (heterologous conditions). DNA isolation and restriction analysis was used to determine the number of different clones.

| Gene | Positive in first screening | positive in rescreening | different clones | clone used for sequencing |
|---|---|---|---|---|
| cbh1 | 8 | 7 | 4 | pCBH7 |
| eg3 | 6 | 6 | 4 | pEG3-3 |
| xyl1 | 9 | 6 | 5 | pXyl5 |
| gpd1 | 12 | 12 | 6 | pGPD4 |

TABLE L

| | glycosidase family | isolated from C1 | number of amino acids | introns | remarks | related sequences (% identity/% homology) |
|---|---|---|---|---|---|---|
| CBH1 | 7 | 70 kD 55 kD | 526 (63 kD) | 1 | CBD | *Humicola grisea* (74/82) (CBH1: P15828) *Fusarium oxysporum* (58/68) (CBH: P46238) *Neurospora crassa* (60/69) (CBH1: P38676) |
| XYL1 | 10 | 30 kD | 333 (43 kD) | 3 | CBD | *Fusarium oxysporum* (67/72) (XylF: P46239) *Penicillium simplissicum* (63/72) (XylF: P56588) *Aspergillus aculeatus* (61/70) (XylF: O59859) |
| EG3 | 12 | — | 247 (30 kD + glycos) | 2 | prepro peptide | *Aspergillus aculeatus* (60/71) (Fl-CMCase: P22669) *Hypocrea jecorina* (56/73) (EG: BAA20140) *Aspergillus kawachii* (54/69) (CMCase: Q12679) |
| EG6 | 6(2) | 43 kD | 395 | 2 | no CBD | *Fusarium oxysporum* (48/59) (EGLB: P46236) *Acremonium cellulolyticus* (48/58) (CBHII: BAA74458) *Agaricus bisporus* (46/59) (CBH3: P49075) |
| EG5 | 45 | 25 kD | 225 | 3 | no CBD | *Humicola grisea* (82/91) (EG: BAA74957) *Fusarium oxysporum* (63/78) (EGL-K: P45699) *Humicola grisea* (62/78) (EG: BAA74956) |

TABLE L-continued

| glycosidase family | isolated from C1 | number of amino acids | introns | remarks | related sequences (% identity/% homology) |
|---|---|---|---|---|---|
| GPD1 | — | — | Incomplete | 2 + ? | — | Podospora anserina (85/89) (GPD: P32637) Neurospora crassa (80/86) (GPD: U67457) Cryphonectria parasitica (80/85) (GPD: P19089) |

DESCRIPTION OF THE FIGURES

FIGS. 13a–13e: pH dependencies of activity of enzymes from NB fractions of F-60-31 CF sample.

FIGS. 16a–16e: Temperature dependencies of enzymes from NB fraction of F-60-31 sample.

REFERENCES (the Contents Hereof are Incorporated)

Figure 1:
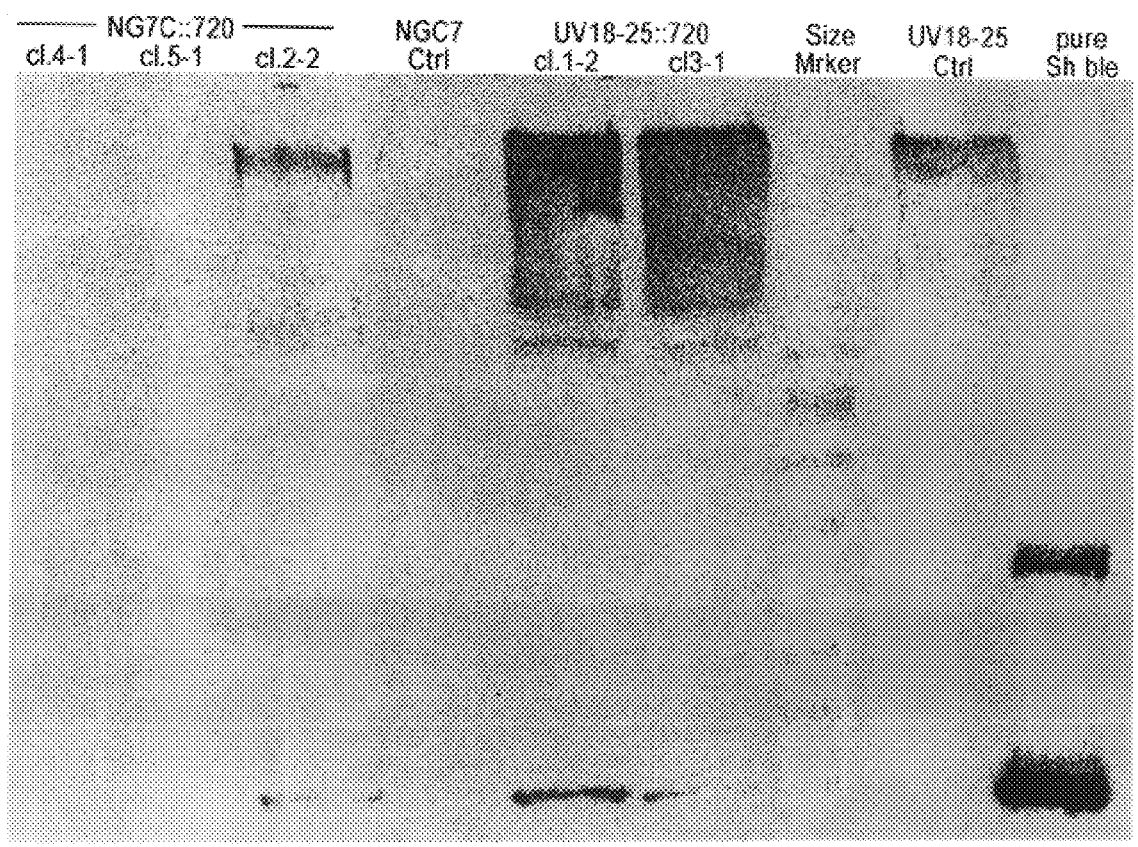
FIG. 1 is a Western blot as described in the Examples
Figure 2:
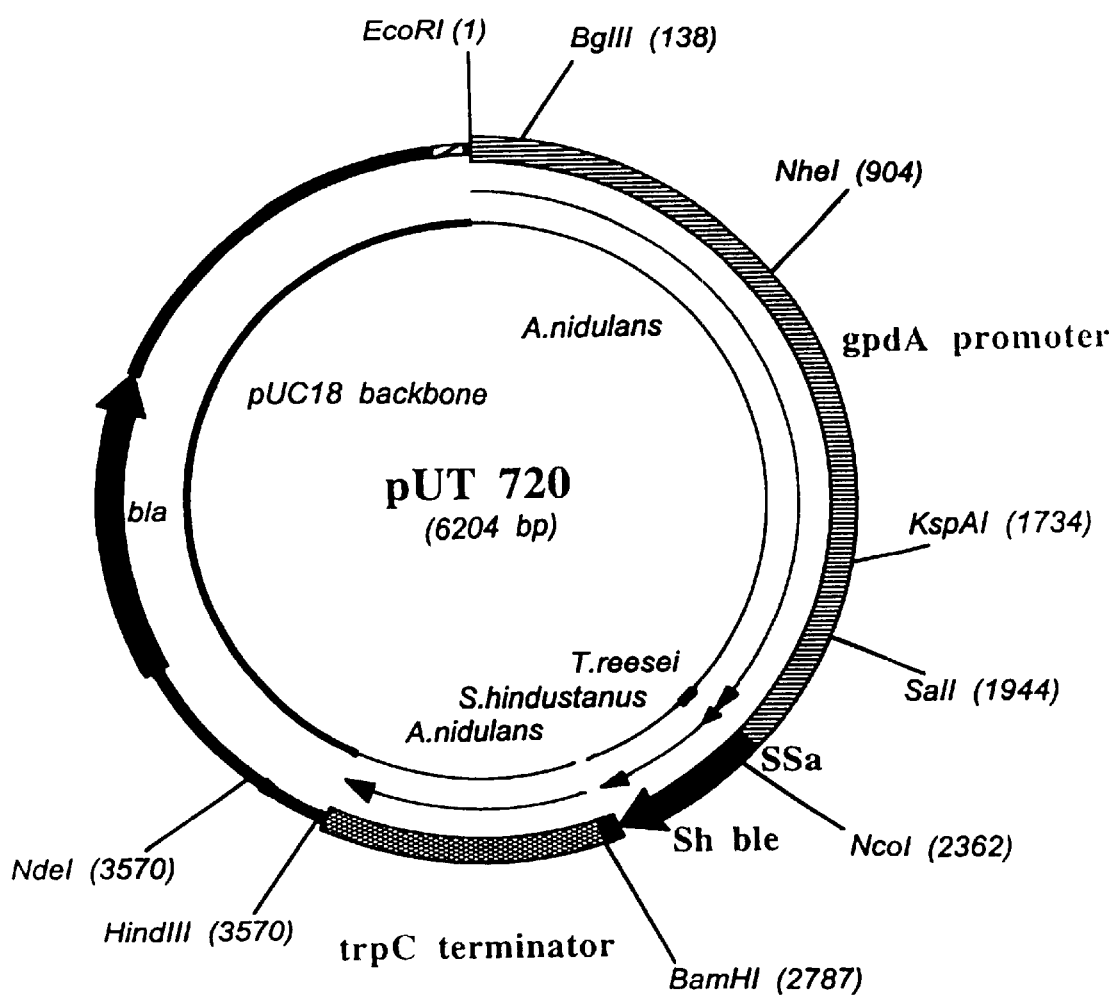
FIG. 2 is a pUT720 map
Figure 3:
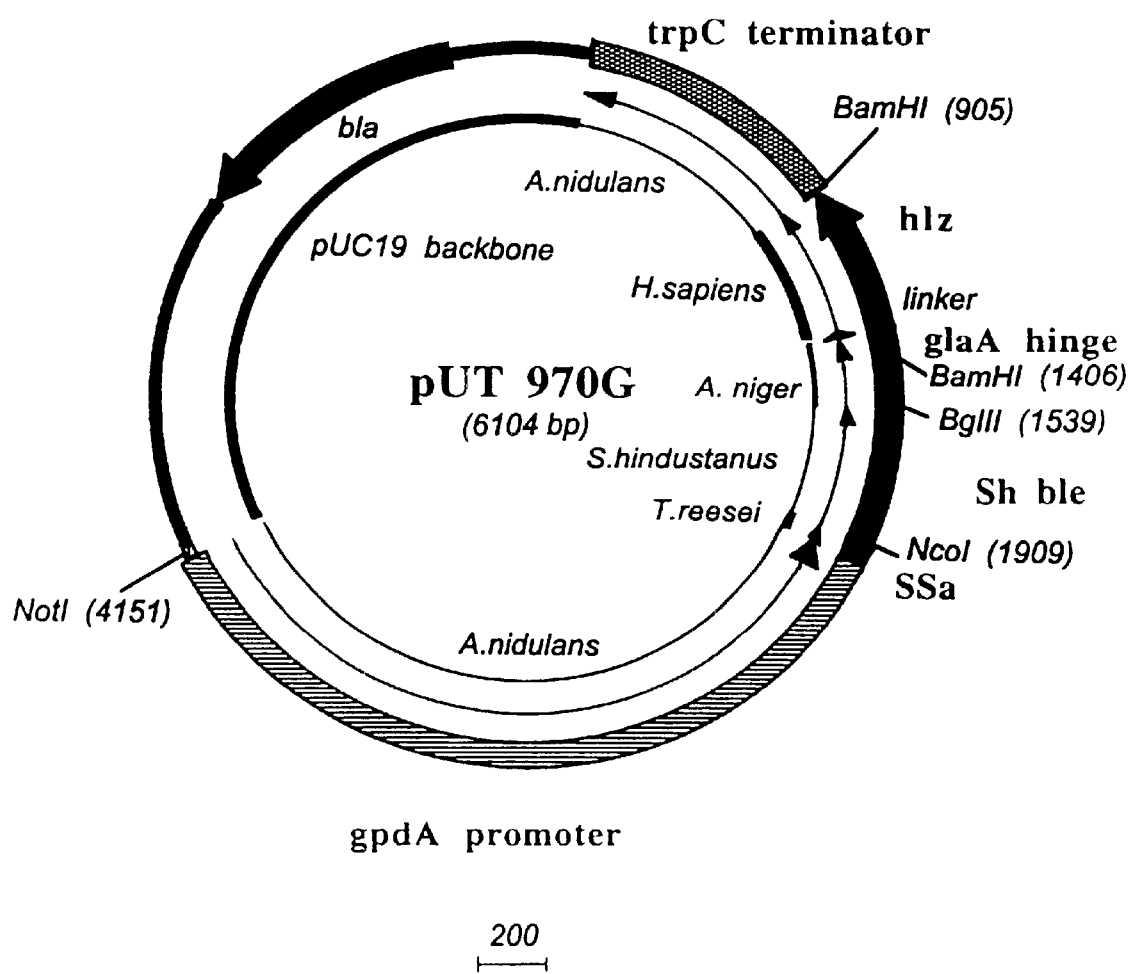
FIG. 3 is a pUT970G map
Figure 4:
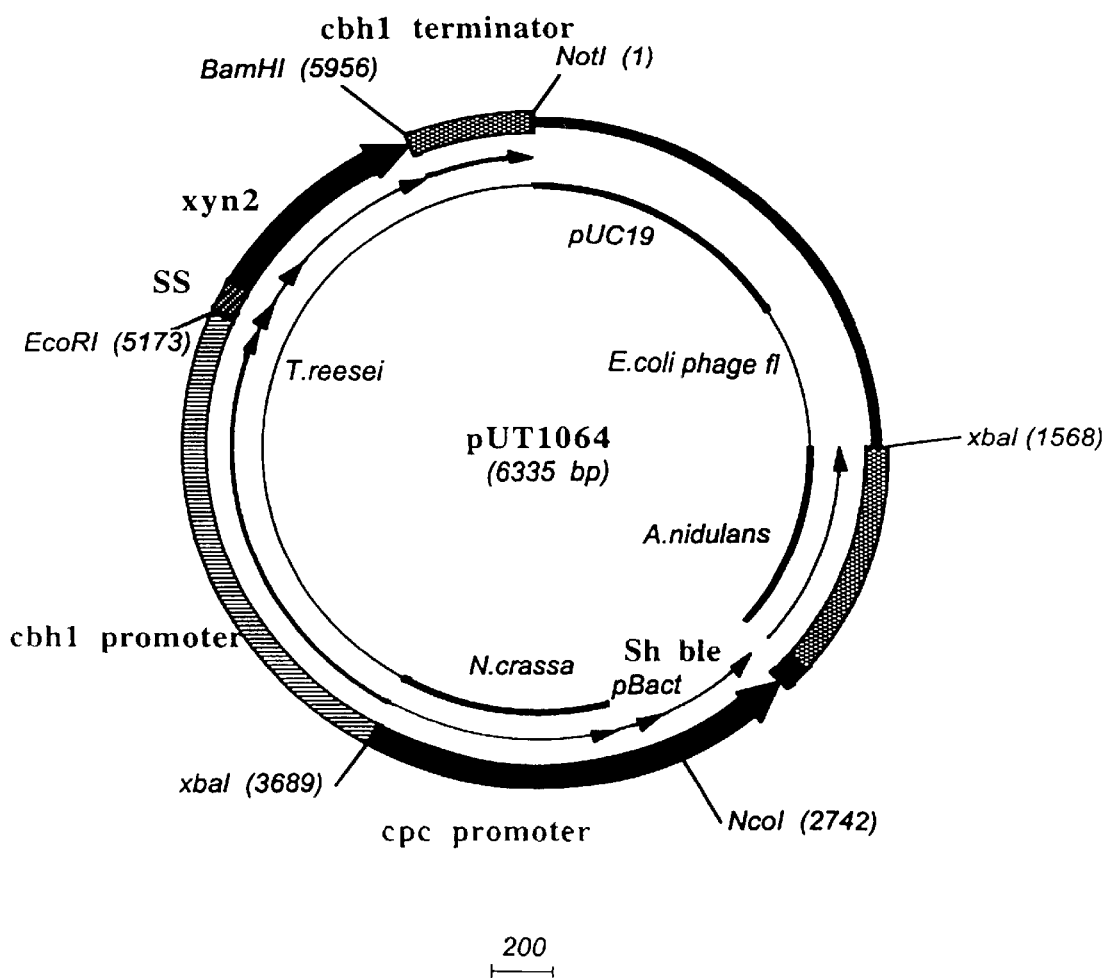
FIG. 4 is a pUT1064 map
Figure 5:
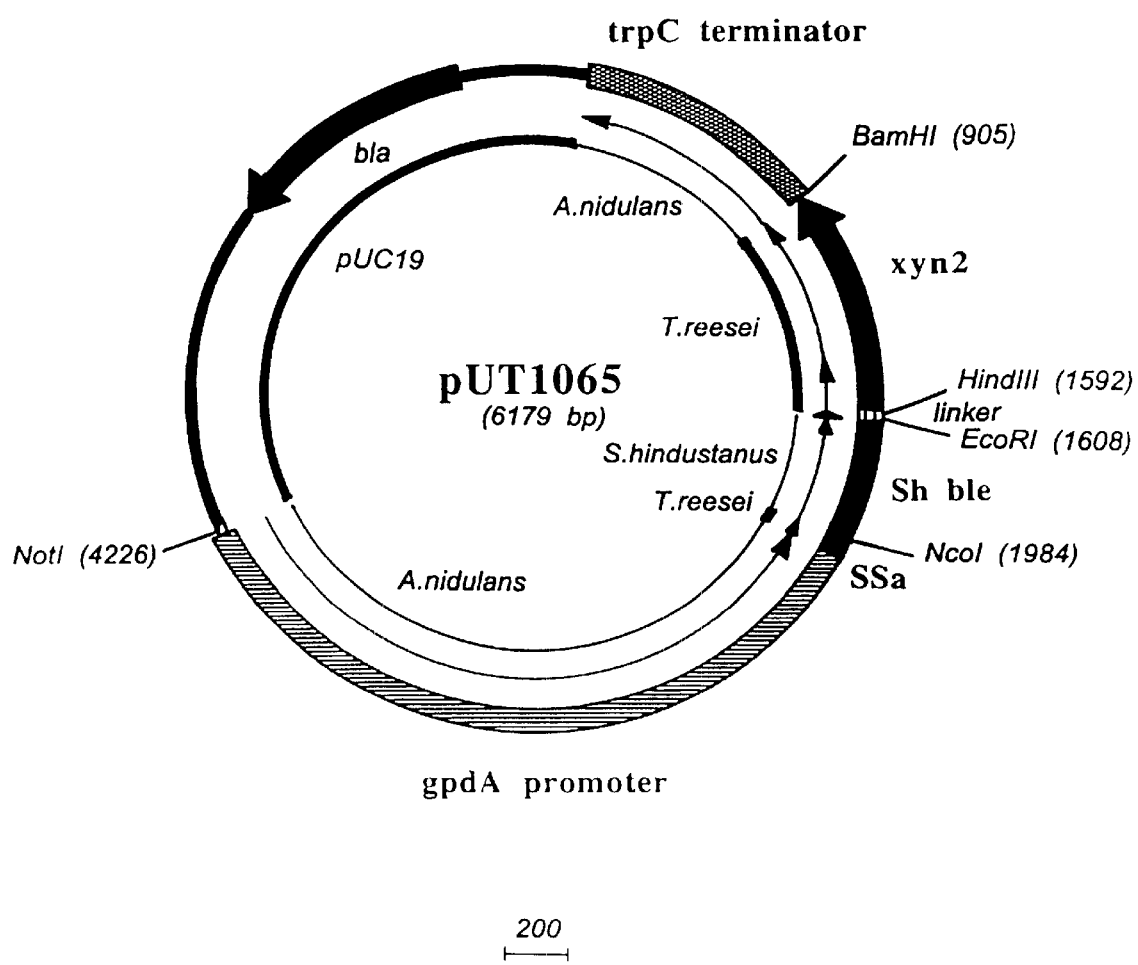
FIG. 5 is a pUT1065 map
Figure 6:
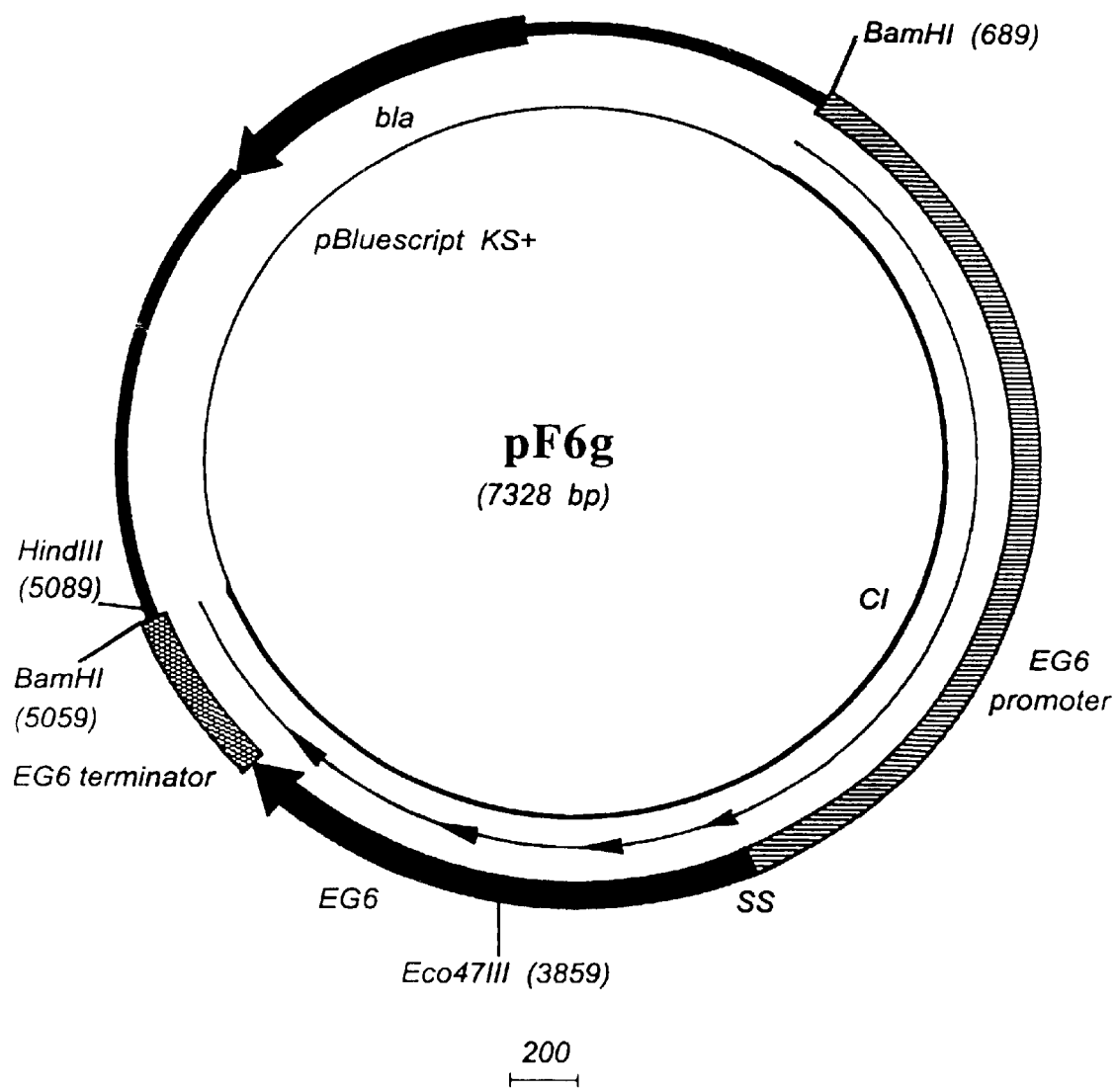
FIG. 6 is a pF6 g map
Figure 7:
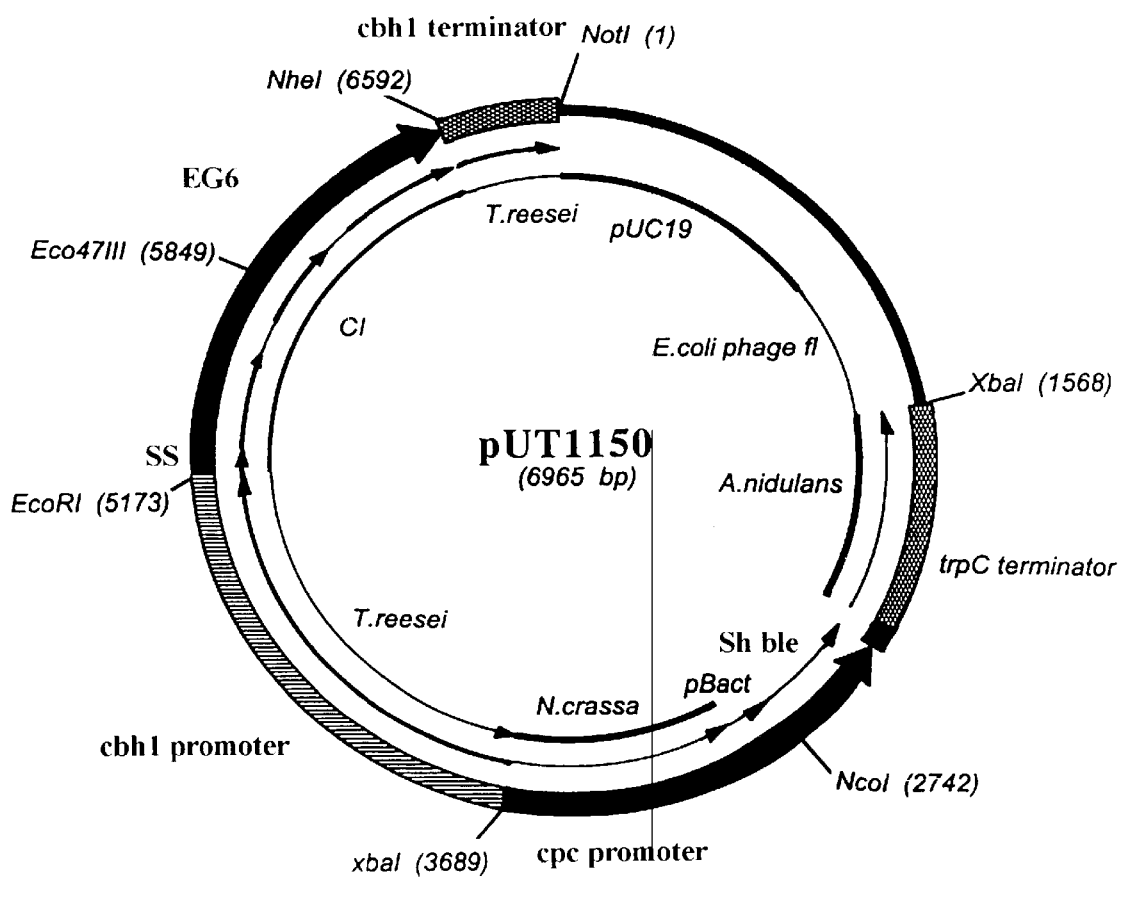
FIG. 7 is a pUT1150 map
Figure 8:
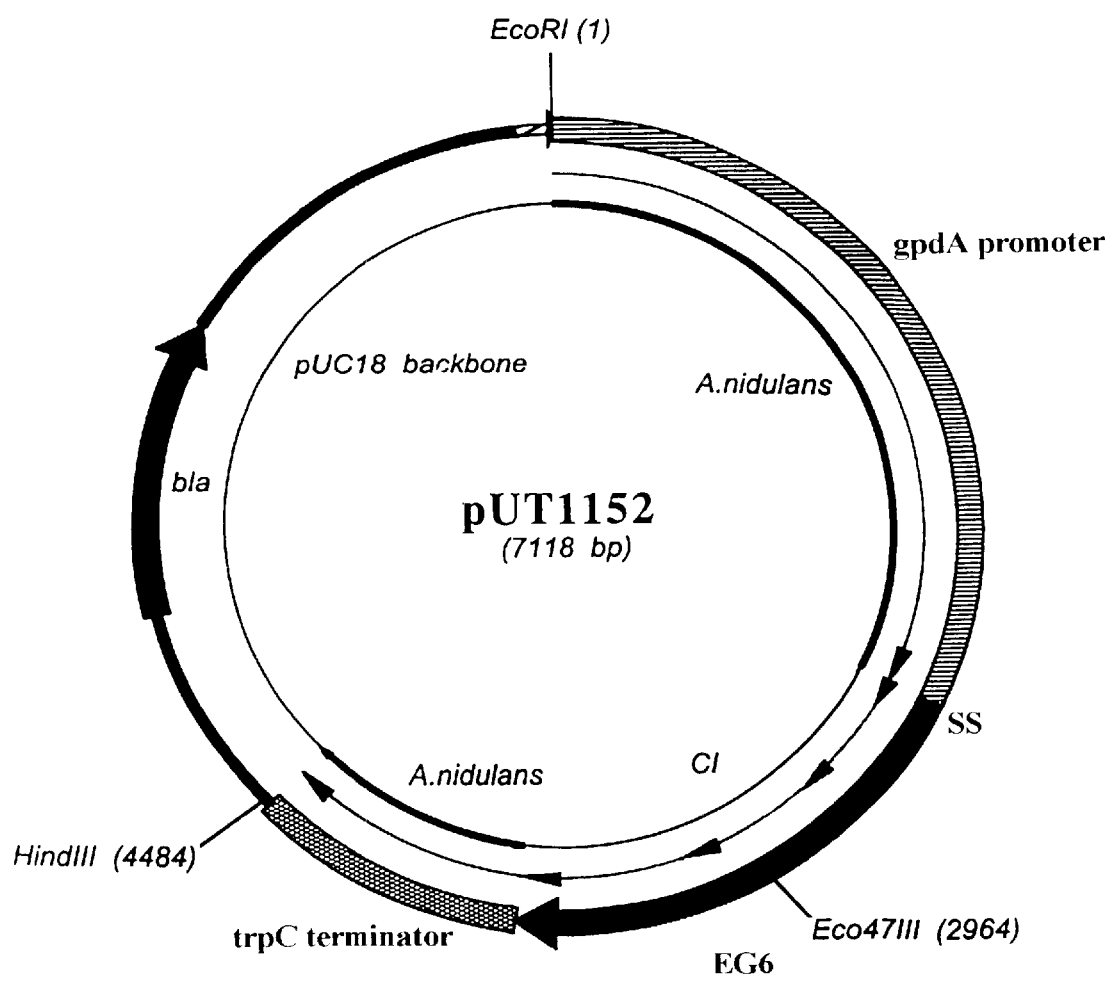
FIG. 8 is a pUT1152 map
Figure 9:
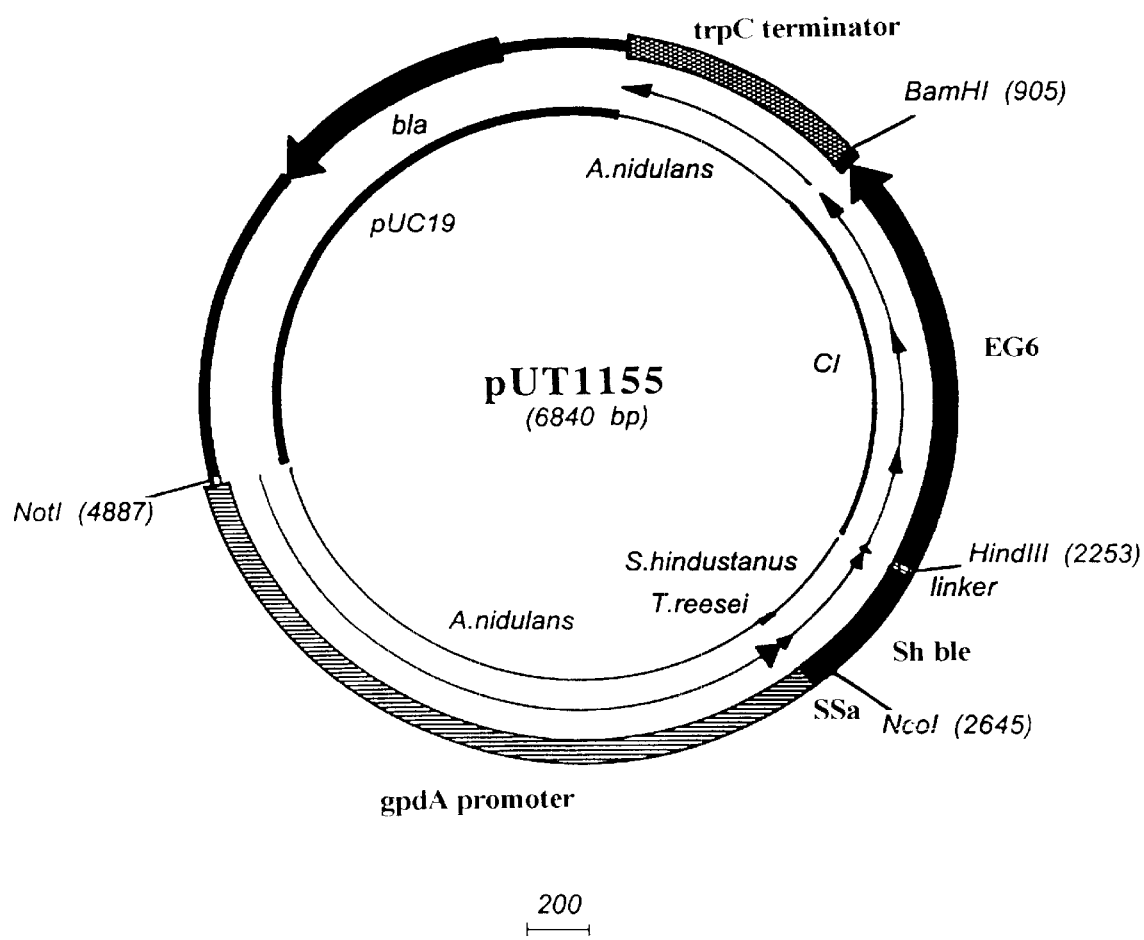
FIG. 9 is a pUT1155 map
Figure 10:
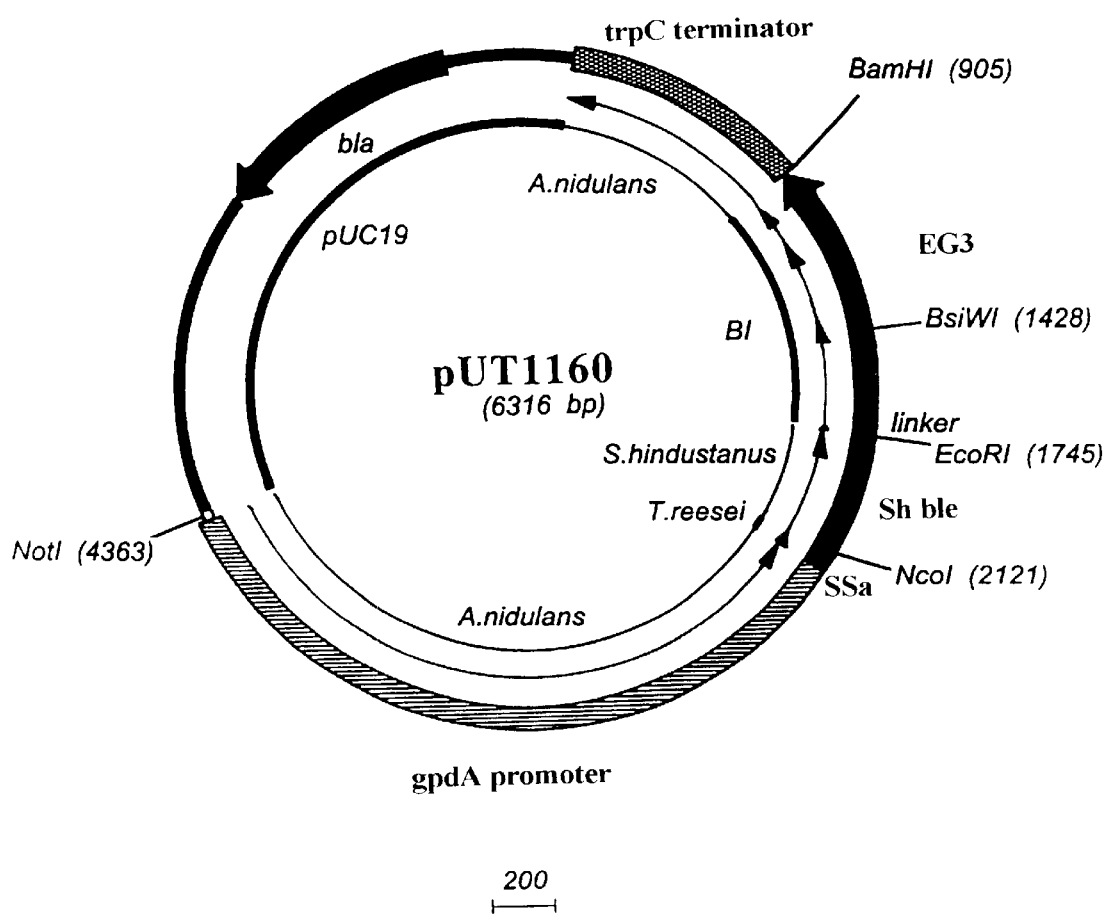
FIG. 10 is a pUT1160 map
Figure 11:
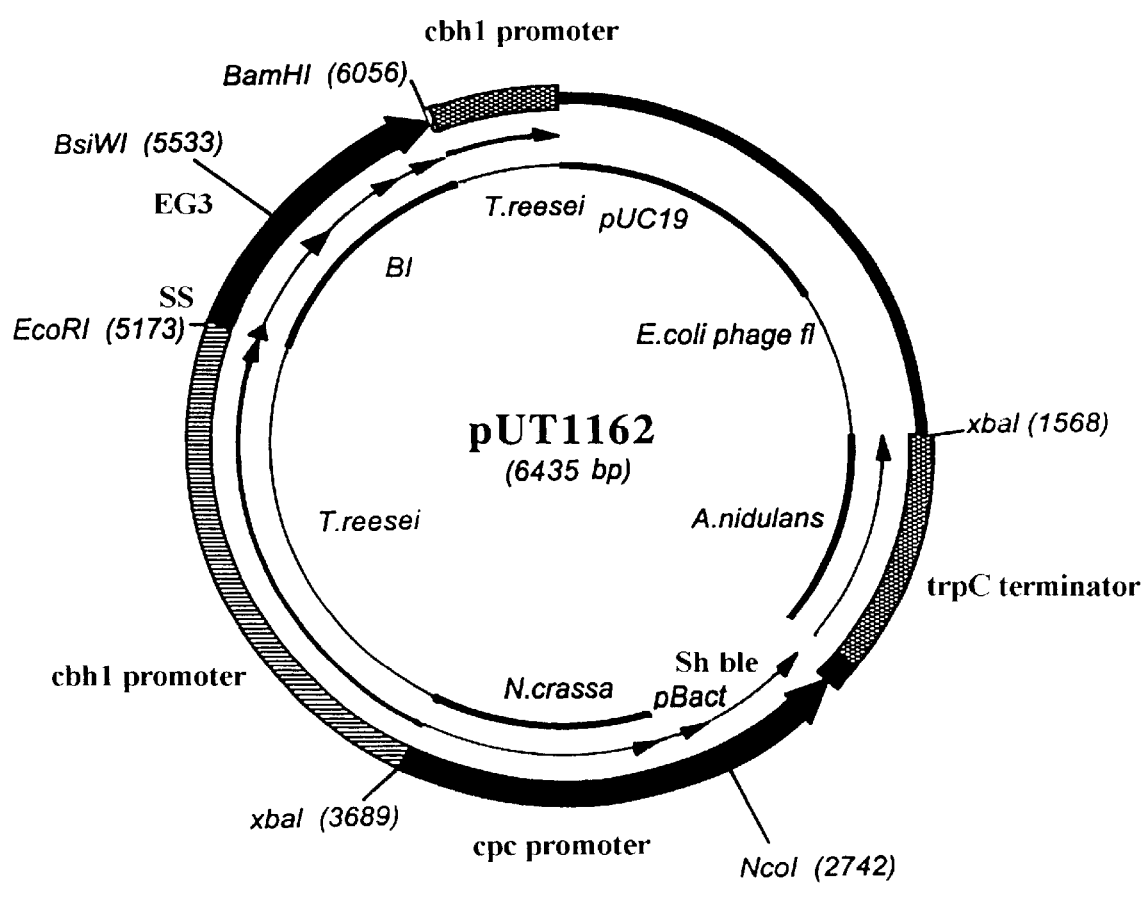
FIG. 11 is a pUT1162 map
Figure 12:
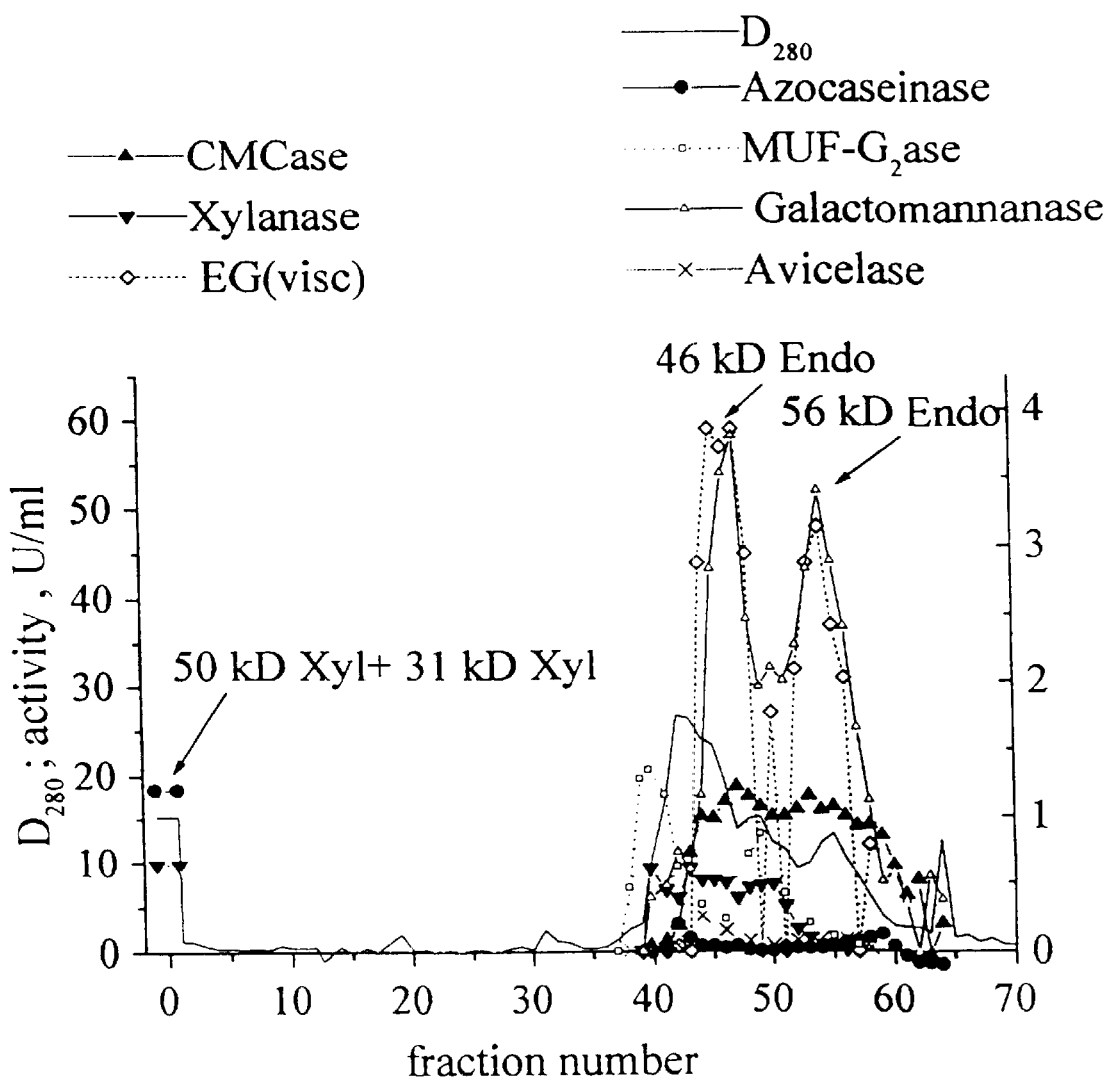
FIG. 12: Ion exchange chromatography on Macro Prep Q of NB-fraction after DEAE-Toyopearl of F-60-31 CF sample.
Figure 14A:
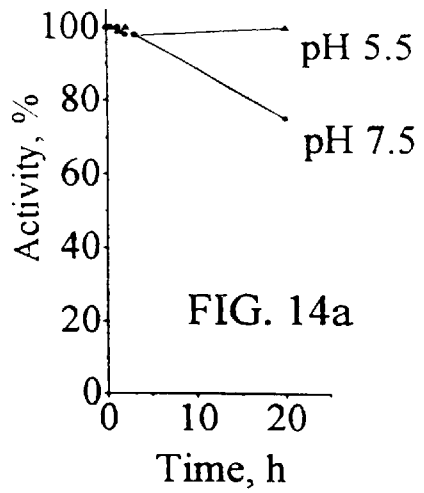
FIGS. 14a–14d: Stability of enzymes from NB fraction of F-60-31 CF sample at pH 5.5 and 7.5 (60° C.).
Figure 14B:
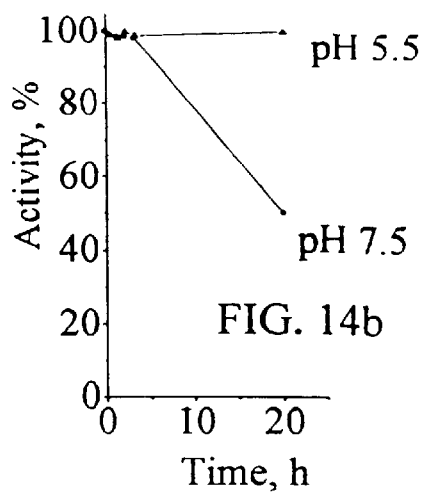
Figure 14C:
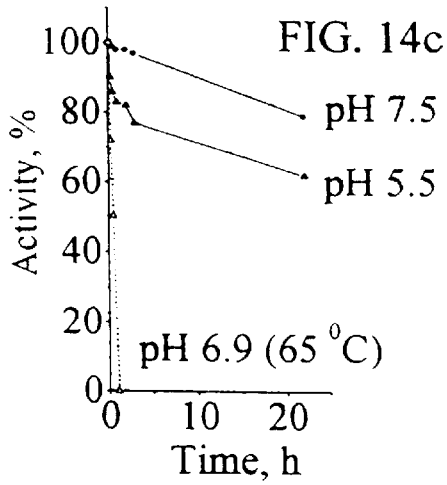
Figure 14D:
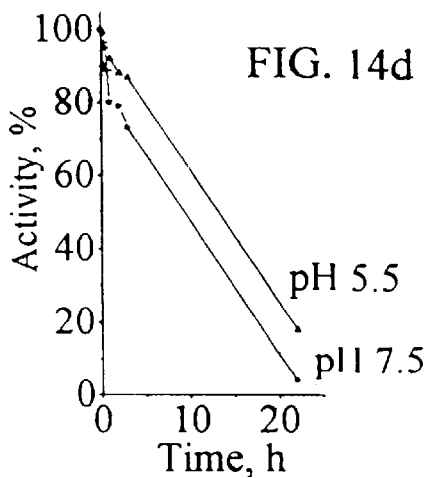
Figure 15A:
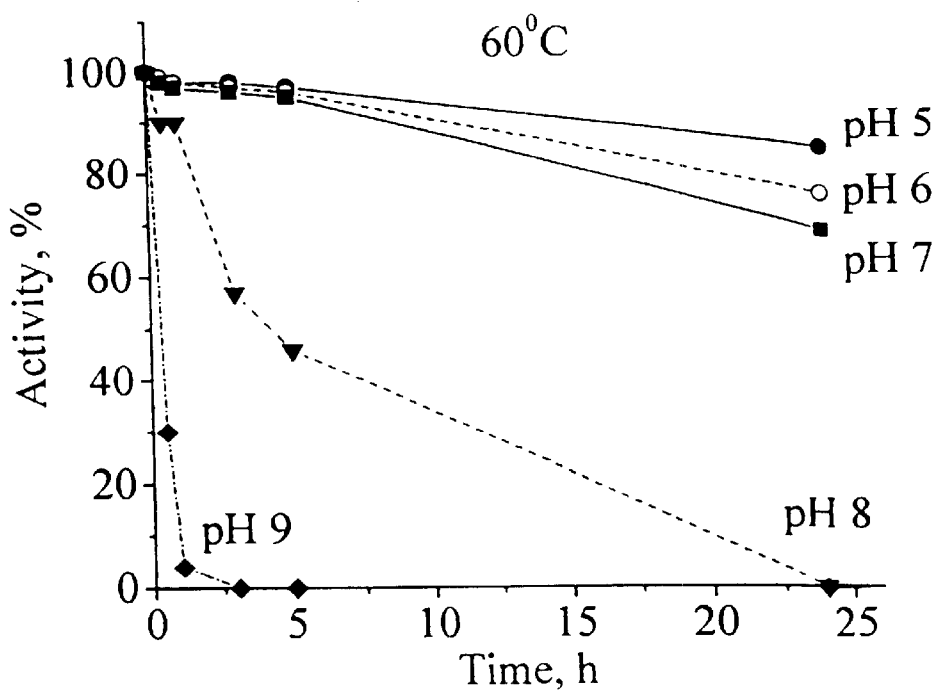
FIGS. 15a and 15b: pH stability at 60° C. and 50° C. of 60 kD Xyl (pI 4.7) from NB fraction of F-60-31 sample.
Figure 15B:
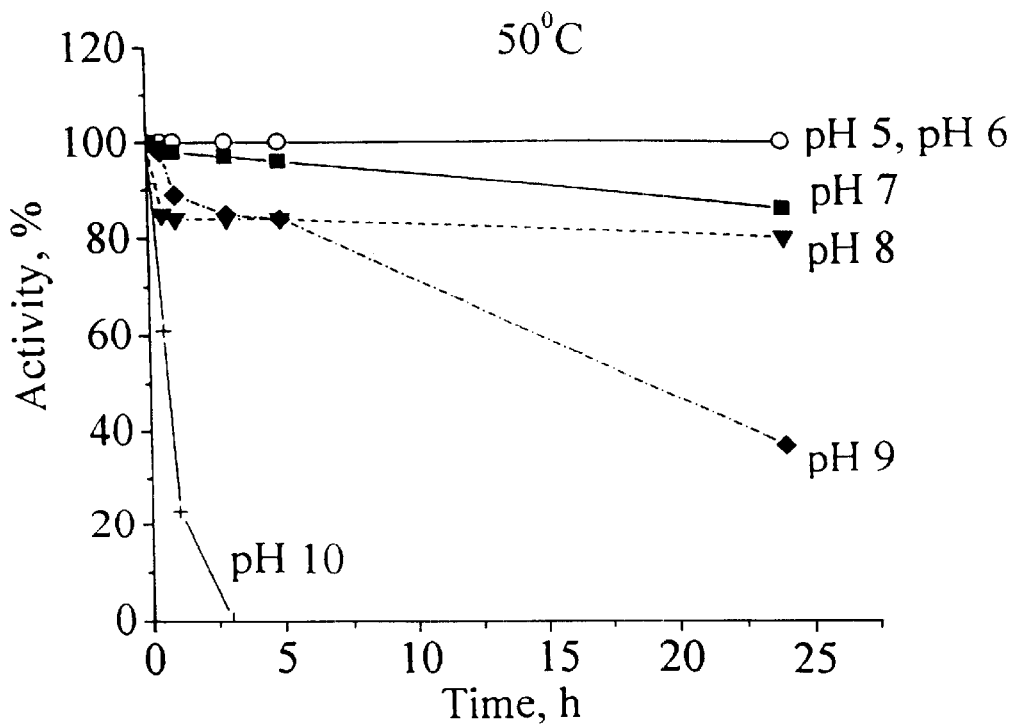
Figure 17:
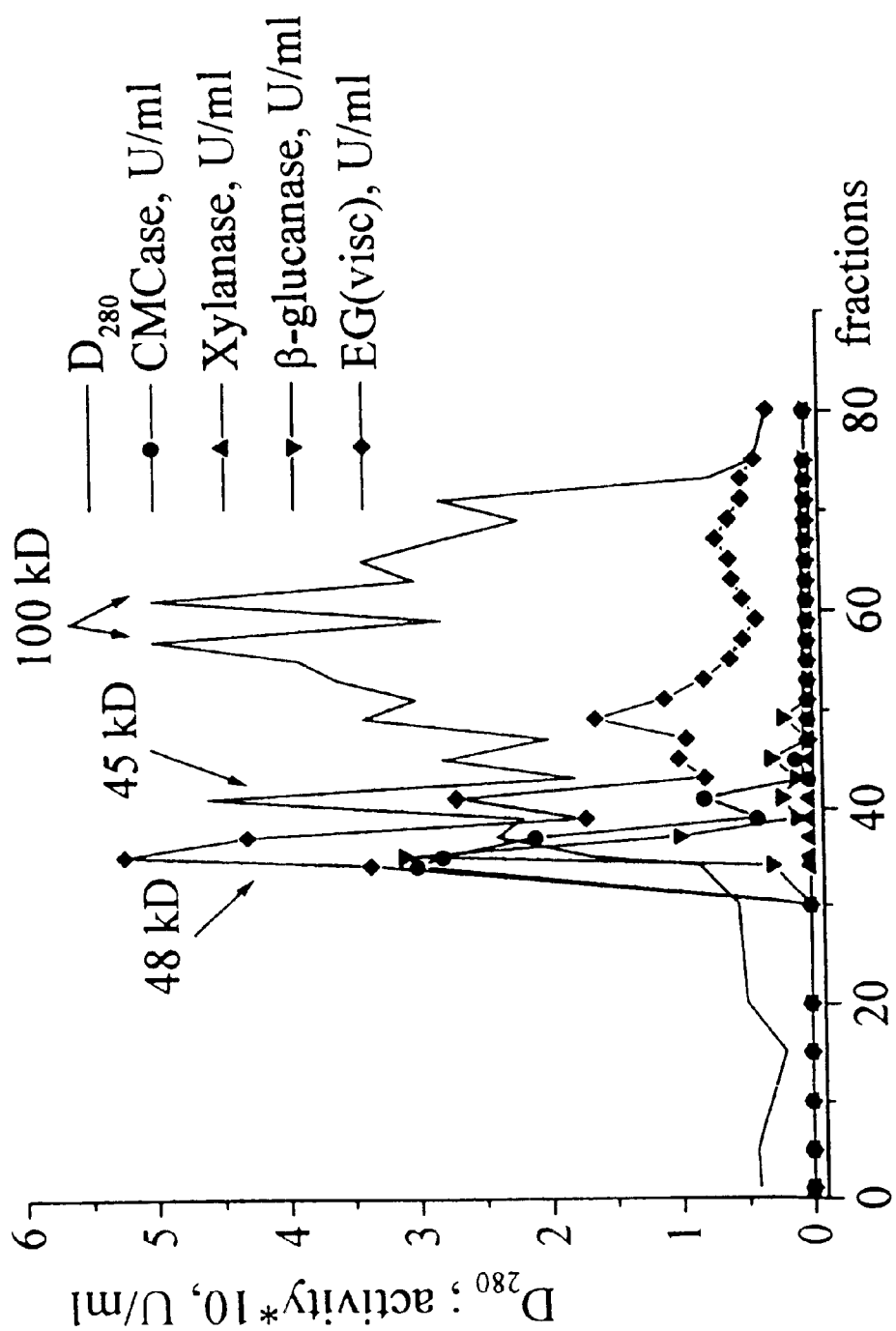
FIG. 17: Ion exchange chromatography on Macro Prep Q of bound fractions 50–53 after DEAE-Toyopearl of F-60-8 sample.
Figure 18A:
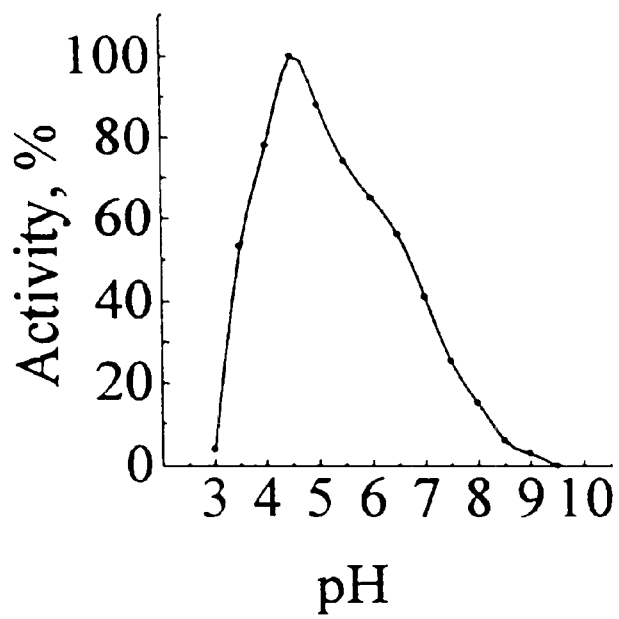
FIGS. 18a and 18b: pH and temperature dependencies of α-galactosidase activity of F-60-43, UF-conc.
Figure 18B:
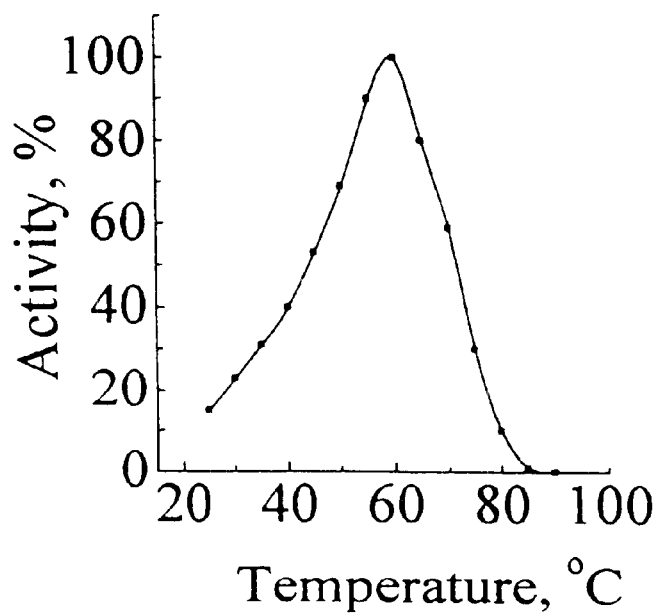
Figure 19:
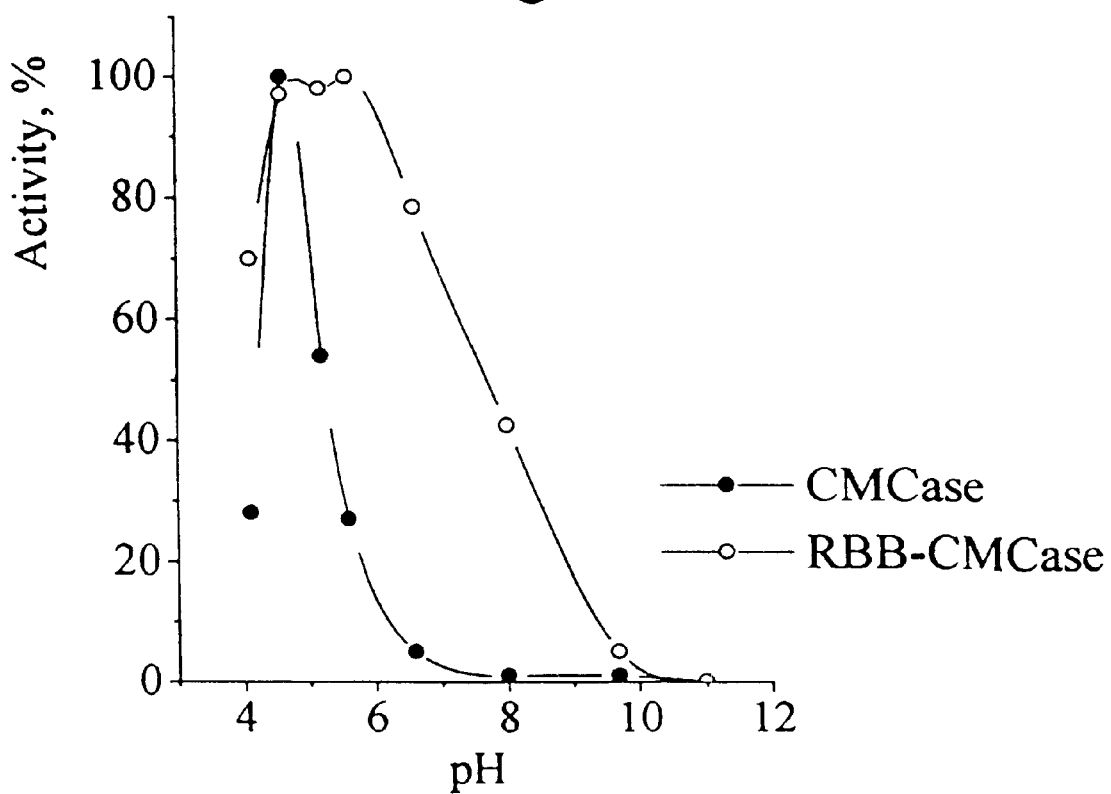
FIG. 19: pH dependencies of activity of 48 kD CBH (pI 4.4) from bound fractions of F-60-8, UF-conc.
Figure 20:
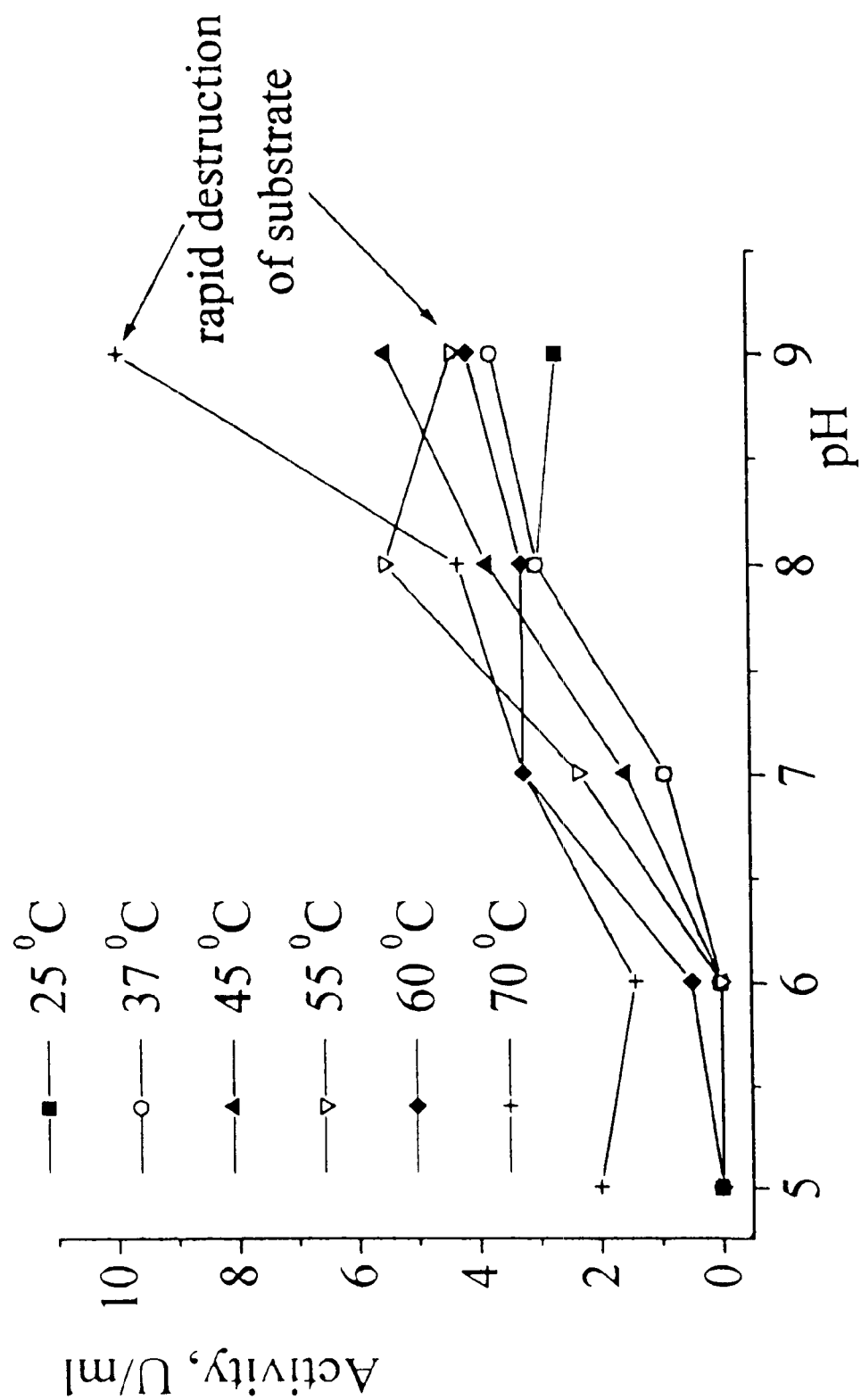
FIG. 20: Temperature dependencies of activity towards p-nitrophenyl butyrate of F-60-8 UF-conc.
Figure 21:
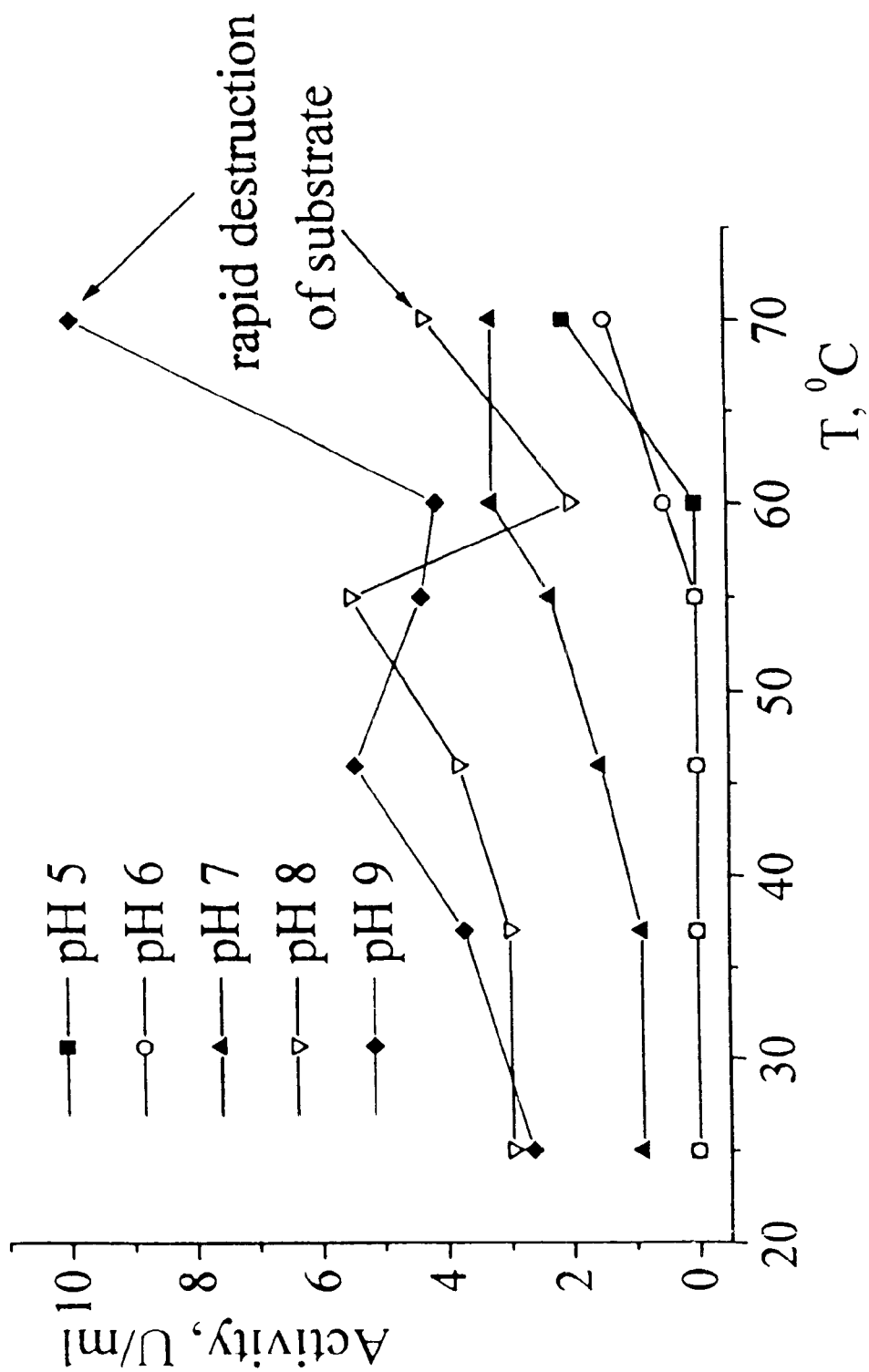
FIG. 21: pH dependencies of activity towards p-nitrophenyl butyrate of F-60-8 UF-conc.
Figure 22:
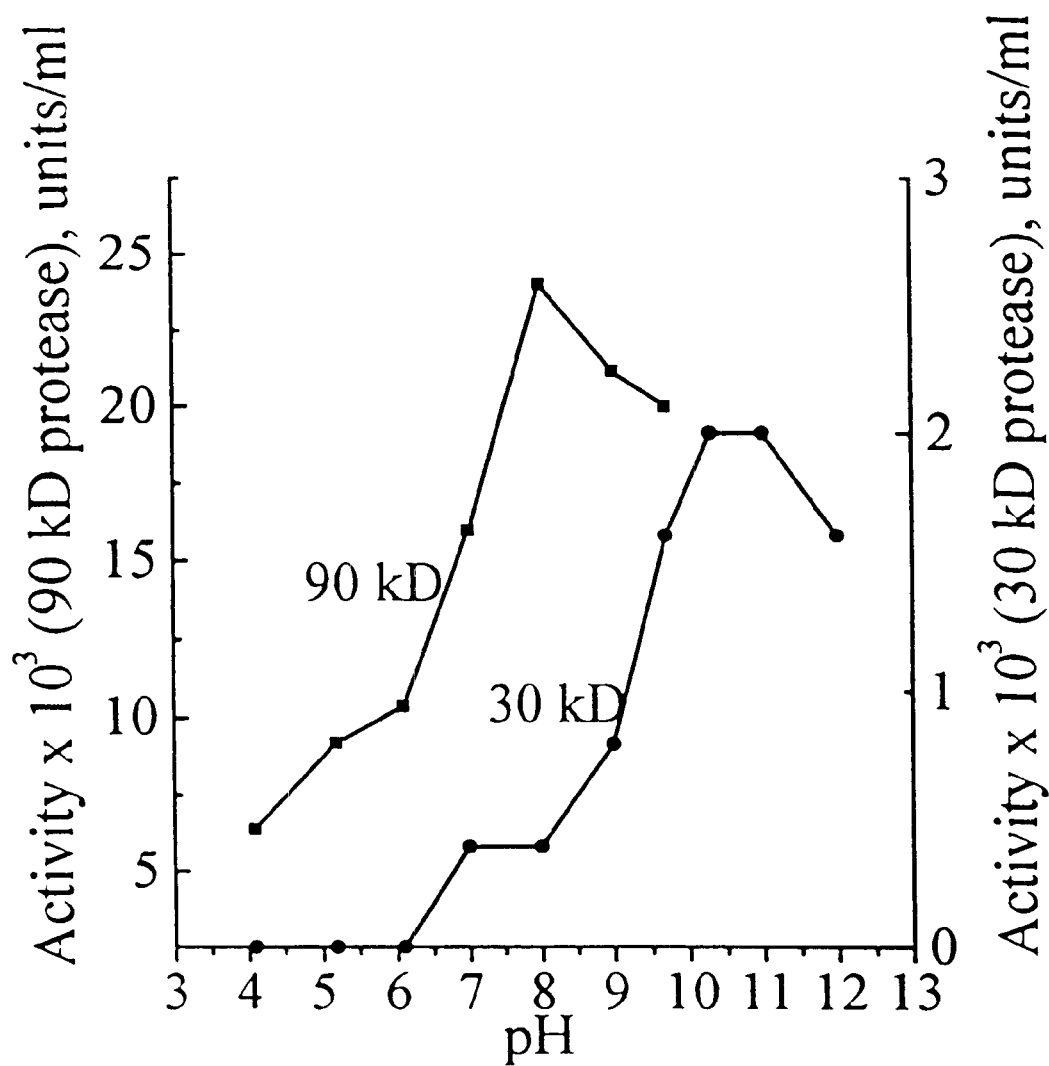
FIG. 22: pH courses of activities of 30 kD (pI 8.9) and 90 kD (pI 4.2) proteases toward C1 proteins (50° C., 30 min. incubation).
Figure 23A:
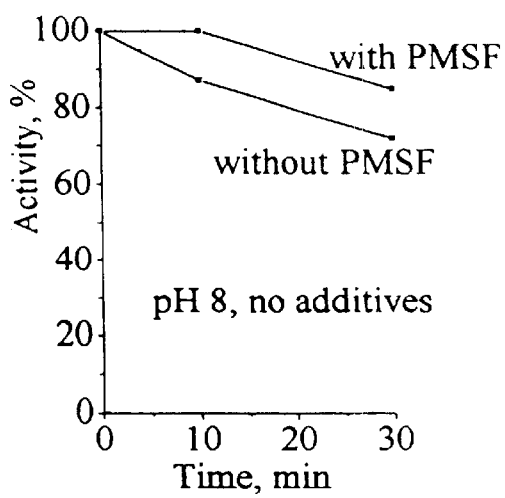
FIGS. 23a–23d: Effect of 30 kD (pI 8.9) "alkaline" protease on xylanase activity of the NBNB-fraction (Macro Prep Q(TM)) of F 60-31 CF at 50° C.
Figure 23B:
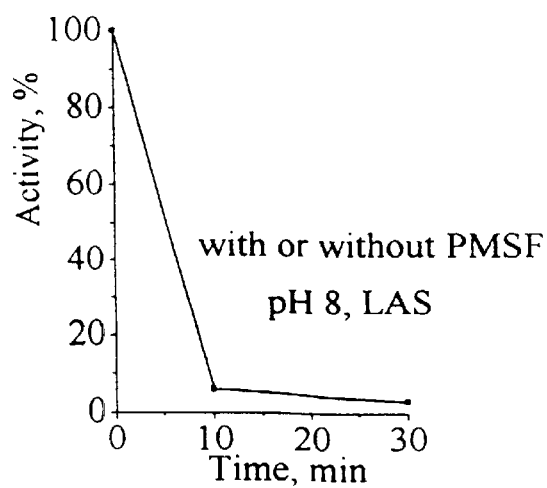
Figure 23C:
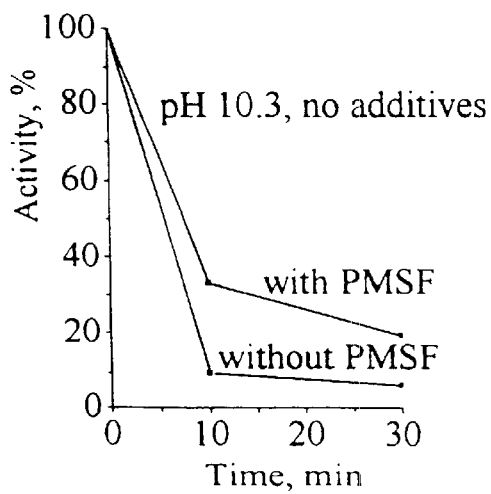
Figure 23D:
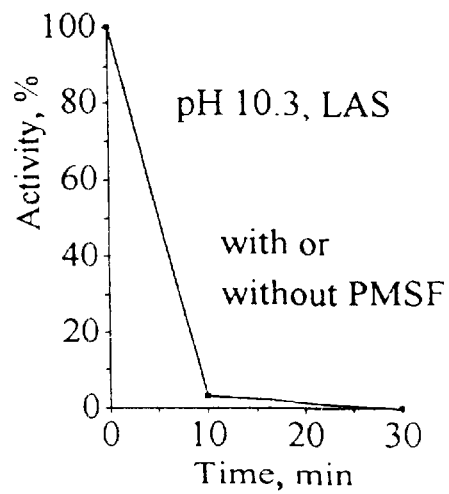
Figure 24A:
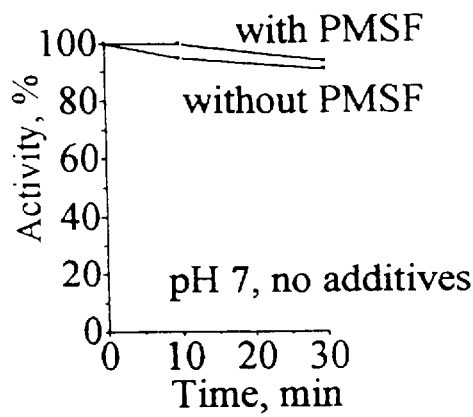
FIGS. 24a–24f: Effect of 90 kD (pI 4.2) "neutral" protease on CMCase activity of the proteins in the bound fraction #44–45 (DEAE-Toyopearl™) of F 60-8 UV-conc sample at 50° C.
Figure 24D:
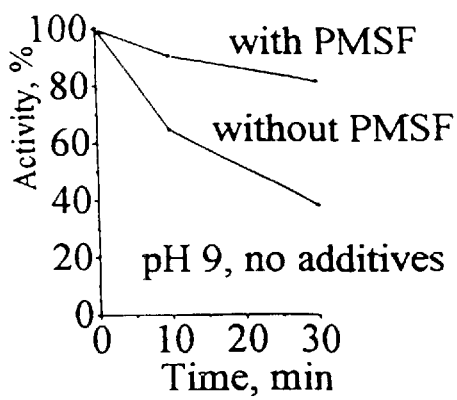
Figure 24B:
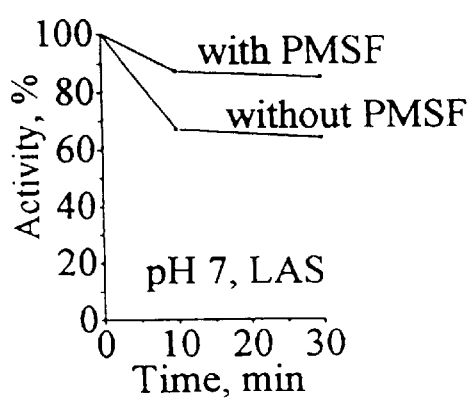
Figure 24E:
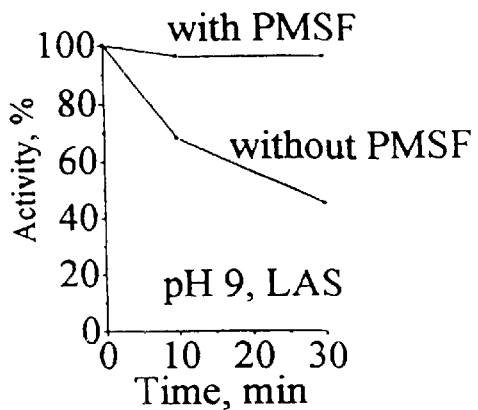
Figure 24C:
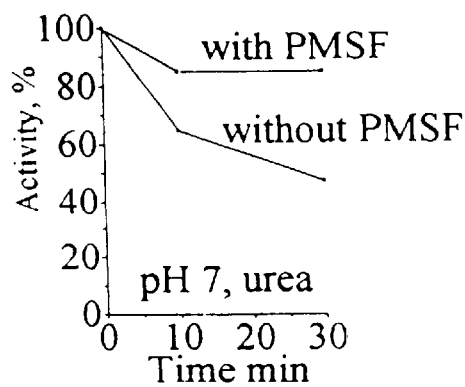
Figure 24F:
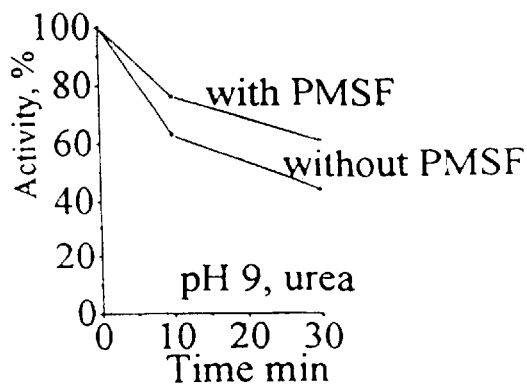
Figure 25:
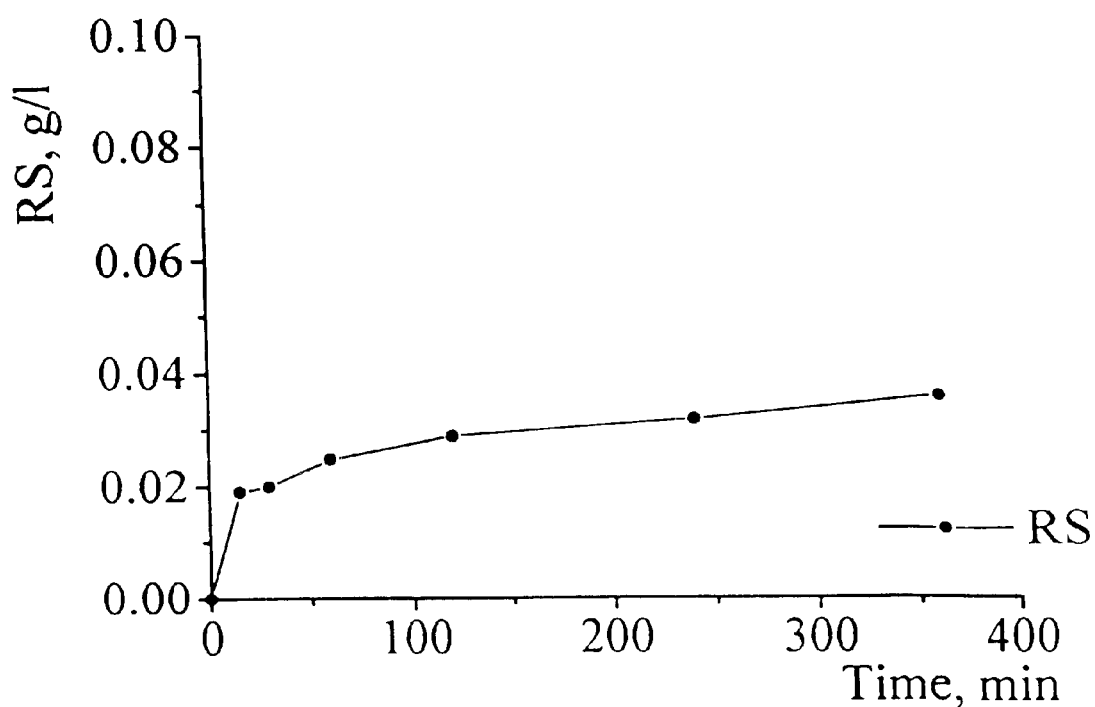
FIG. 25: Complete hydrolysis of polygalacturonic acid by 65 kD polygalacturonase (pI 4.4): 50° C., pH 4.5; concentration of PGA=5 g/l, concentration of protein=0.1 g/l.
Figure 26A:
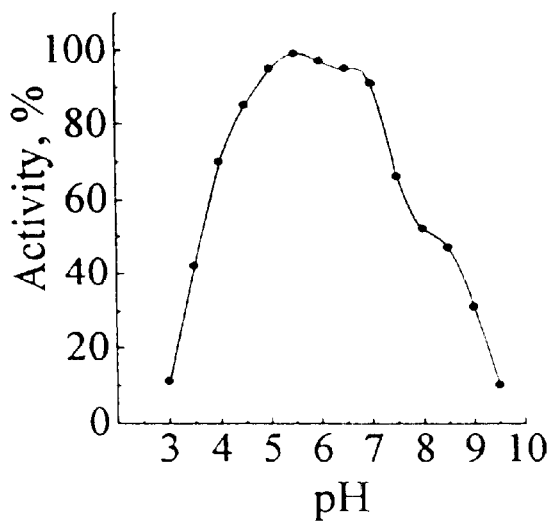
FIGS. 26a and 26b: pH- and temperature dependencies of polygalacturonase activity of F-60-43 UF-conc.
Figure 26B:
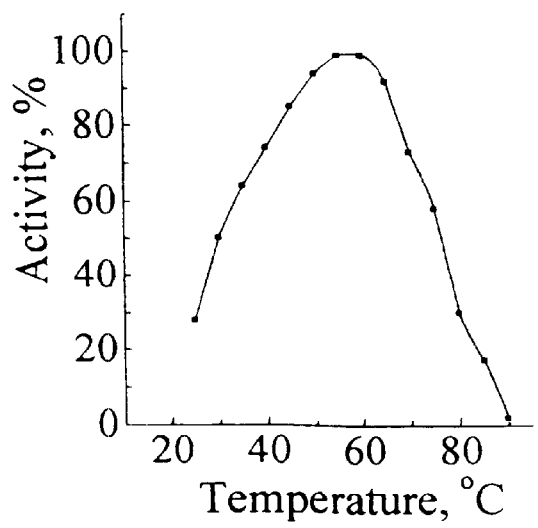
Figure 27:
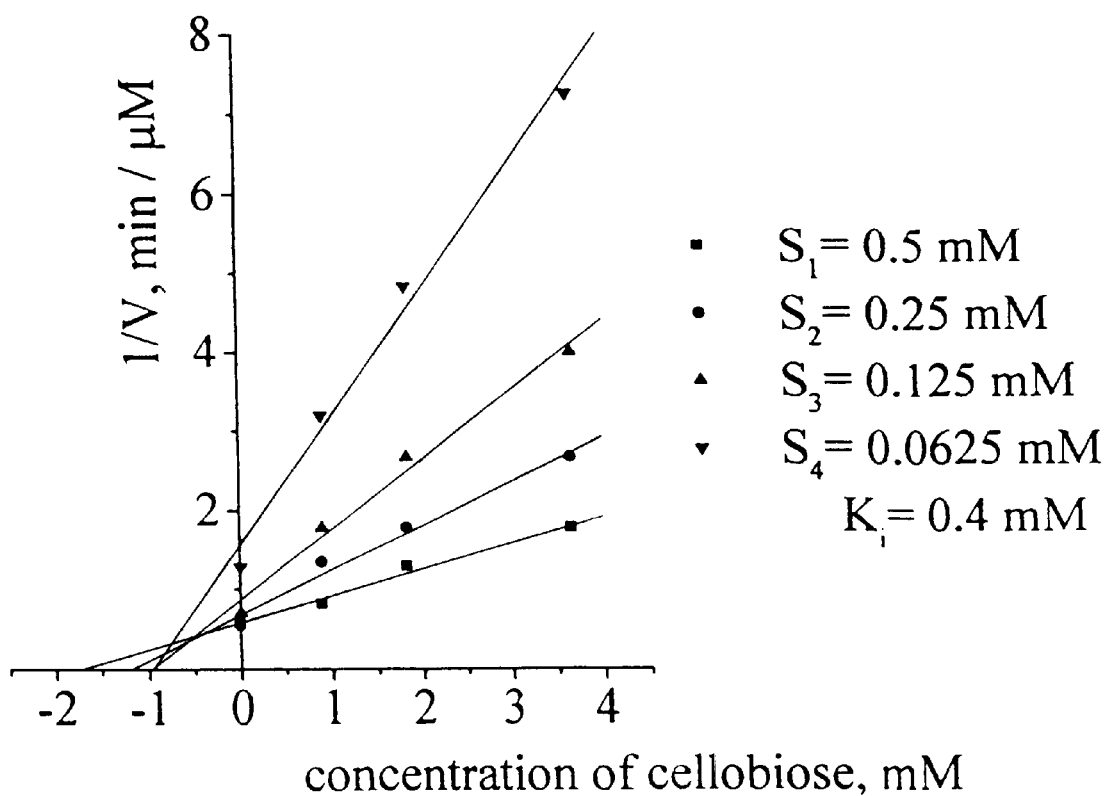
FIG. 27: Inhibition of activity toward MUF-cellobioside by cellobiose for 55 kD CBH (pI 4.4): pH 4.5, 40° C.
Figure 28:
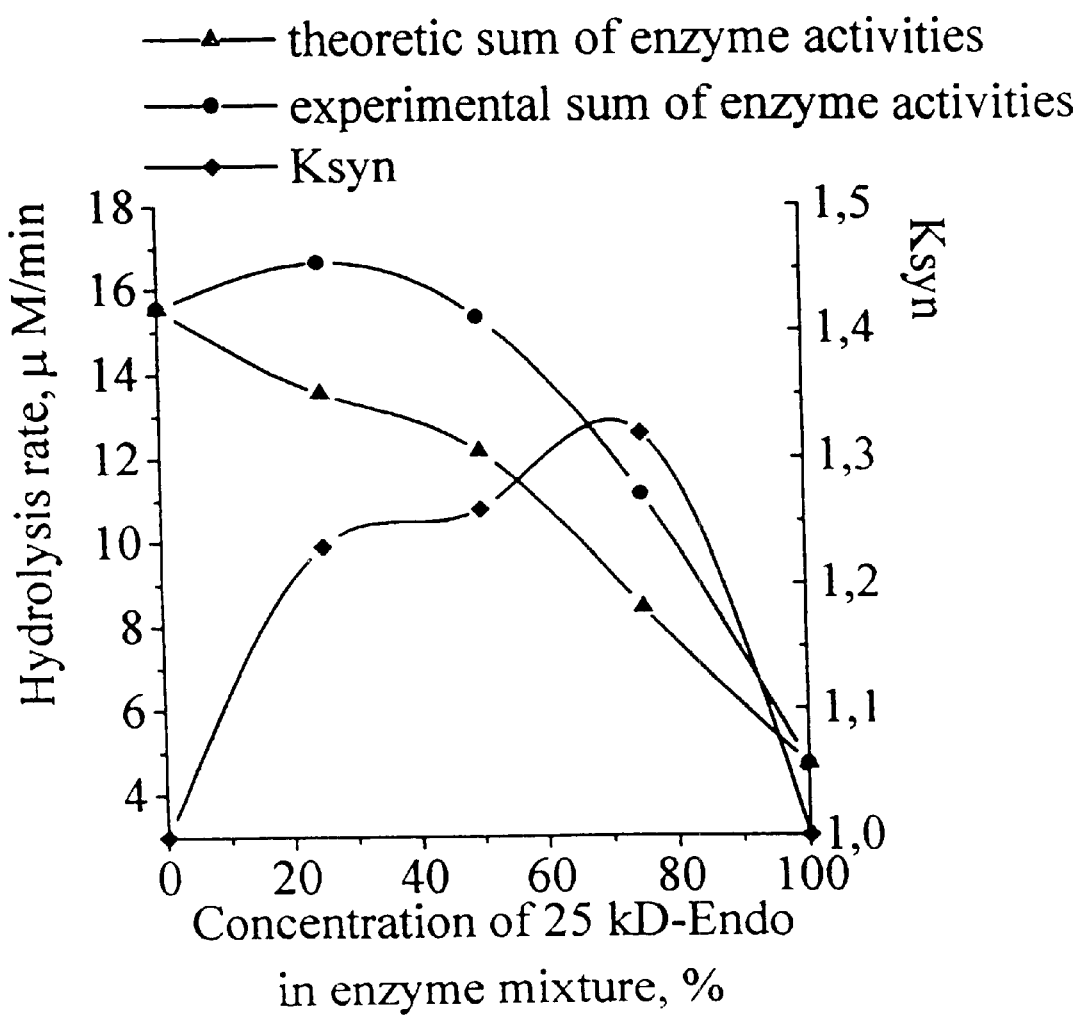
FIG. 28: Synergistic effect between 25 kD Endo (pI 4.1) and 55 kD CBH (pI 4.4) toward avicel (40° C., pH 5, 25 min)
Figure 29A:
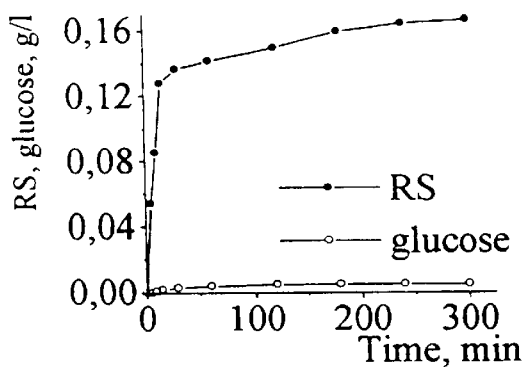
FIGS. 29a–29d: Complete hydrolysis of CMC (a) and avicel (b) by the enzymes isolated from bound fractions of F-60-8 UF-conc. sample (50° C., pH 5) concentration of CMC and avicel=5 g/l, concentration of 25 kD Endo=0–01 g/l, concentration of 43 kD Endo=0.02 g/l; 1–25 kD Endo (pI 4.1), 2–43 kD Endo (pI 4.2).
Figure 29B:
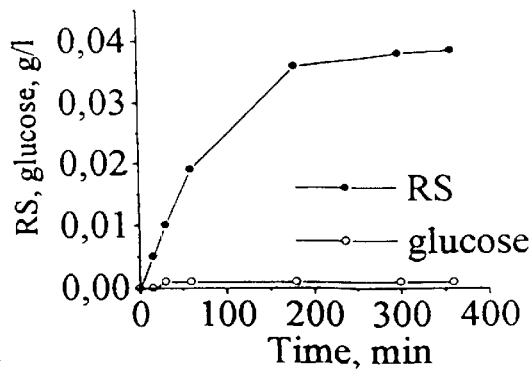
Figure 29C:
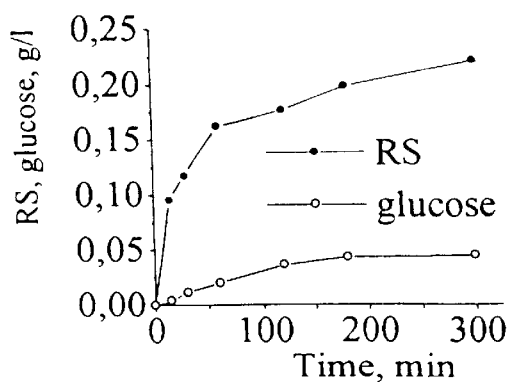
Figure 29D:
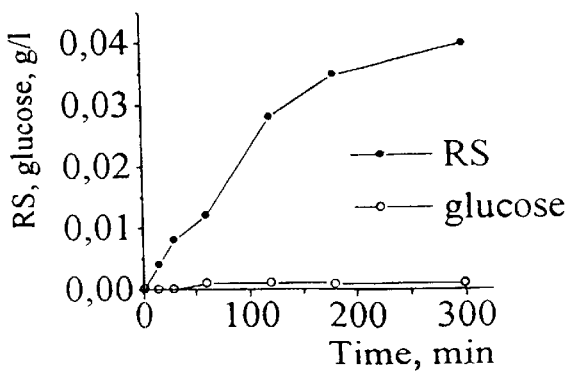
Figure 30B:
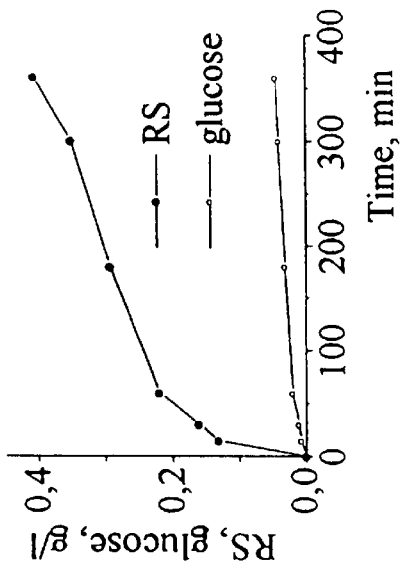
FIGS. 30a–30d: Complete hydrolysis of CMC (1) and avicel (2) by 55 kD CBH (pI 4.4) without (a) and with (b) glucono-δ-lactone (50° C., pH 4.5): concentration of CMC and avicel=5 g/l, concentration of protein=0.1 g/l, concentration of glucono-δ-lactone=5 g/l.
Figure 30D:
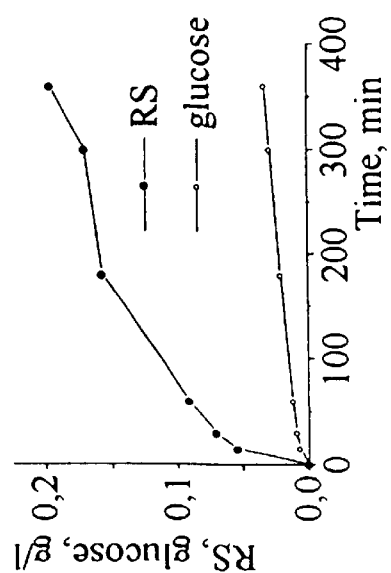
Figure 30A:
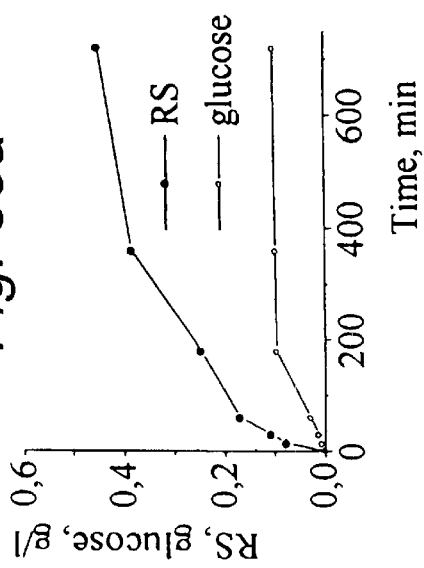
Figure 30C:
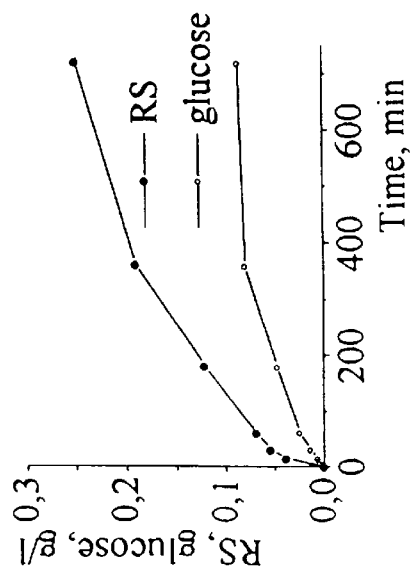
Figure 31A:
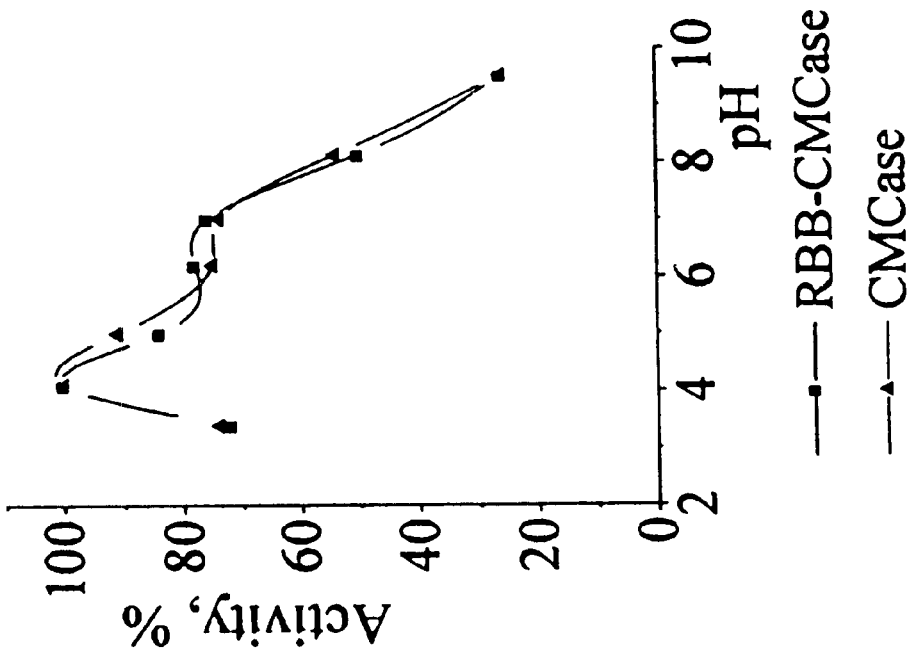
FIGS. 31a and 31b: pH-Dependence of CMCase and RBB-CMCase activities of the enzymes isolated from F-60-8 UF-conc. sample: 1–25 kD Endo (pI 4.1), 2–43 kD Endo (pI 4.2).
Figure 31B:
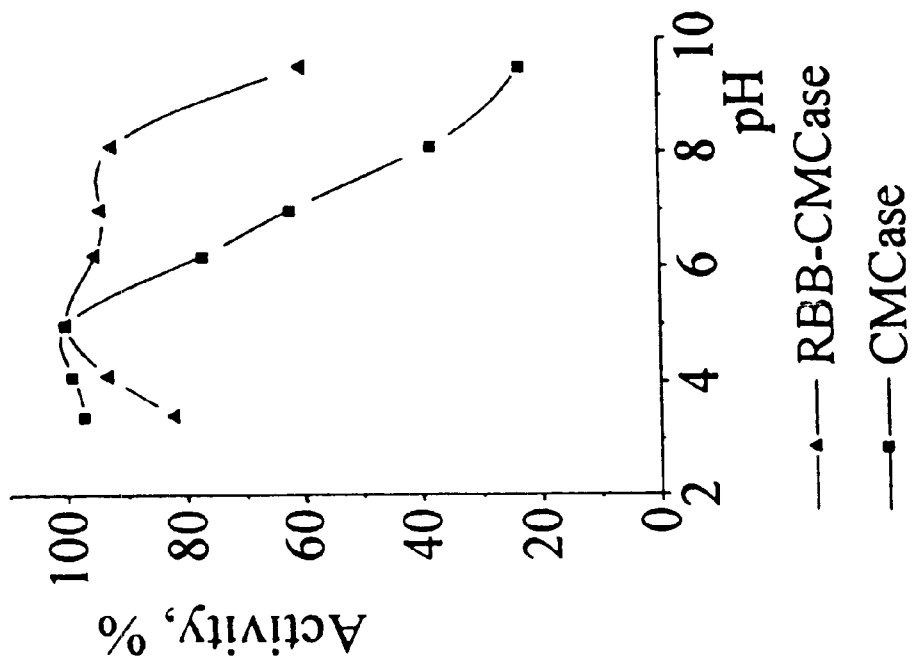
Figure 32:
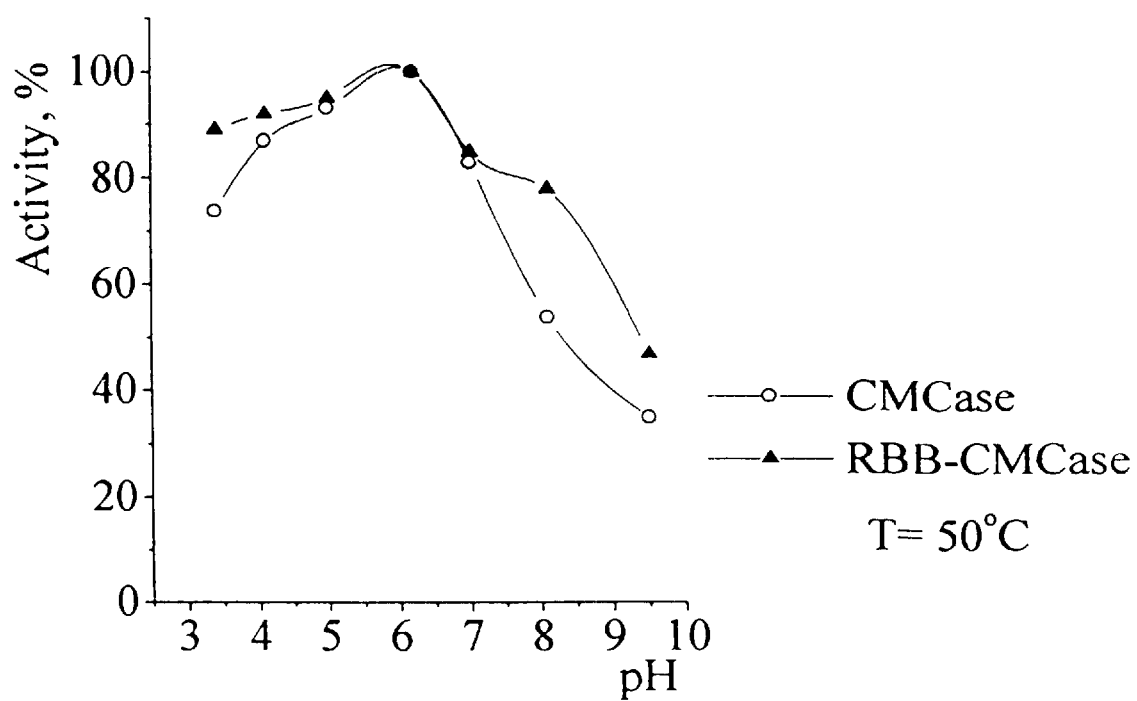
FIG. 32: pH-Dependencies of CMCase and RBB-CMCase activities of 55 kD CBH (pI 4.4).
Figure 33A:
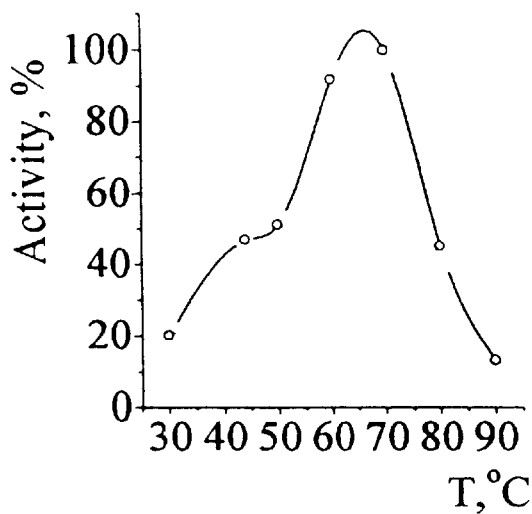
FIGS. 33a–33c: Temperature dependencies of CMCase activity (pH 4.5) of the enzymes isolated from bound fractions of F-60-8 UF-conc. sample: 1–55 kD CBH (pI 4.4), 2–25 kD Endo (pI 4.1), 3–43 kD Endo (pI 4.2).
Figure 33B:
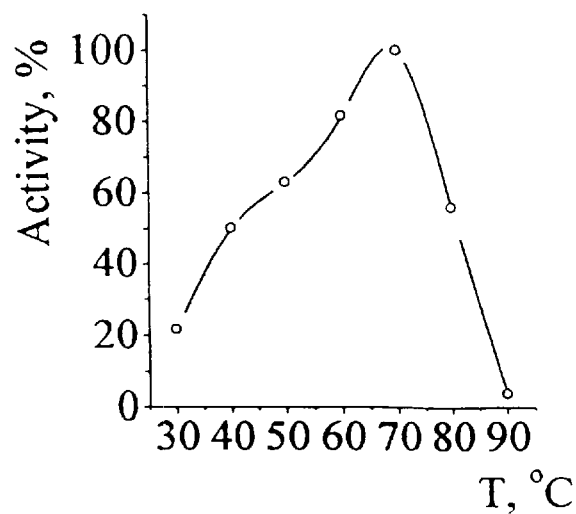
Figure 33C:
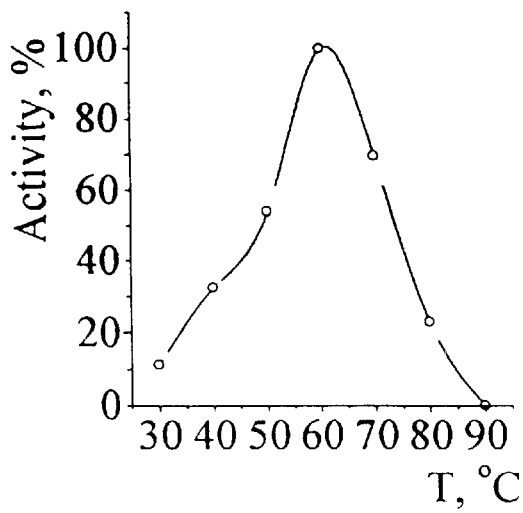
Figure 34A:
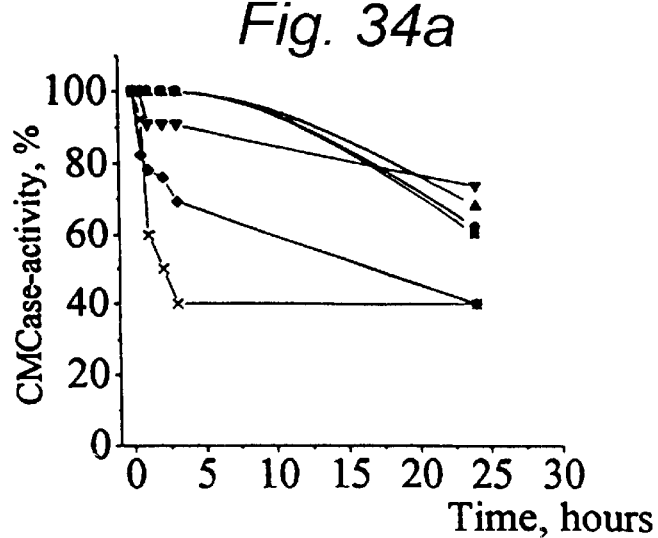
FIGS. 34a–34c: pH-stability (50° C.) of the enzymes isolated from bound fractions of F-60-8 UF-conc. sample: 1–55 kD CBH (pI 4.4), 2–25 kD Endo (pI 4.1), 3–43 kD Endo (pI 4.2).
Figure 34B:
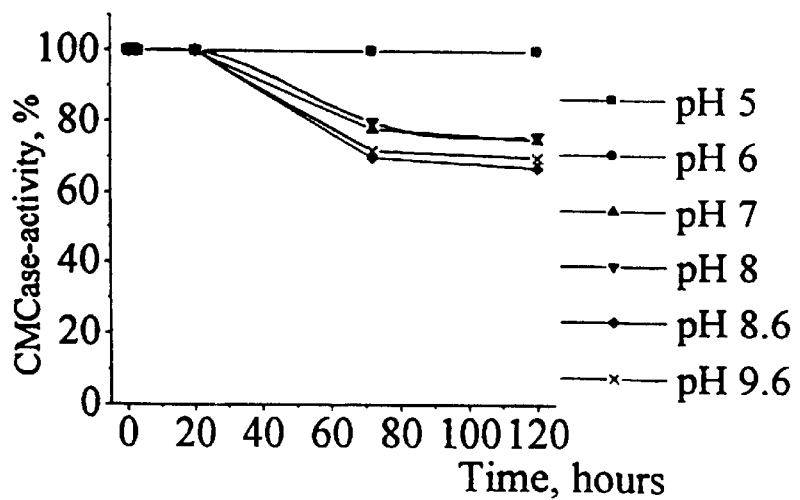
Figure 34C:
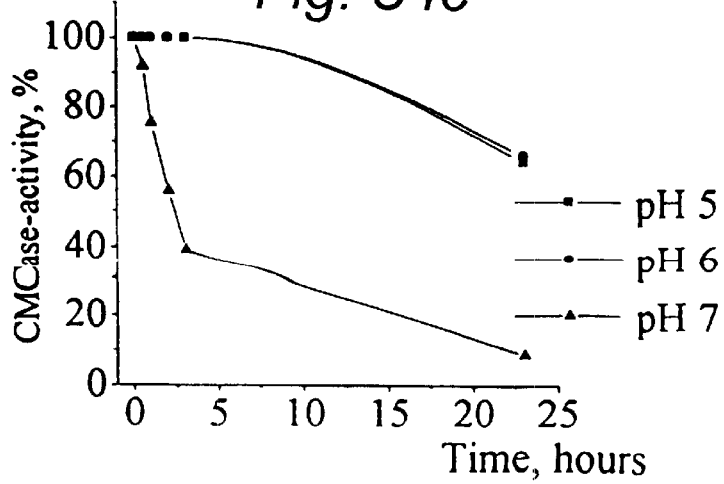
Figure 35:
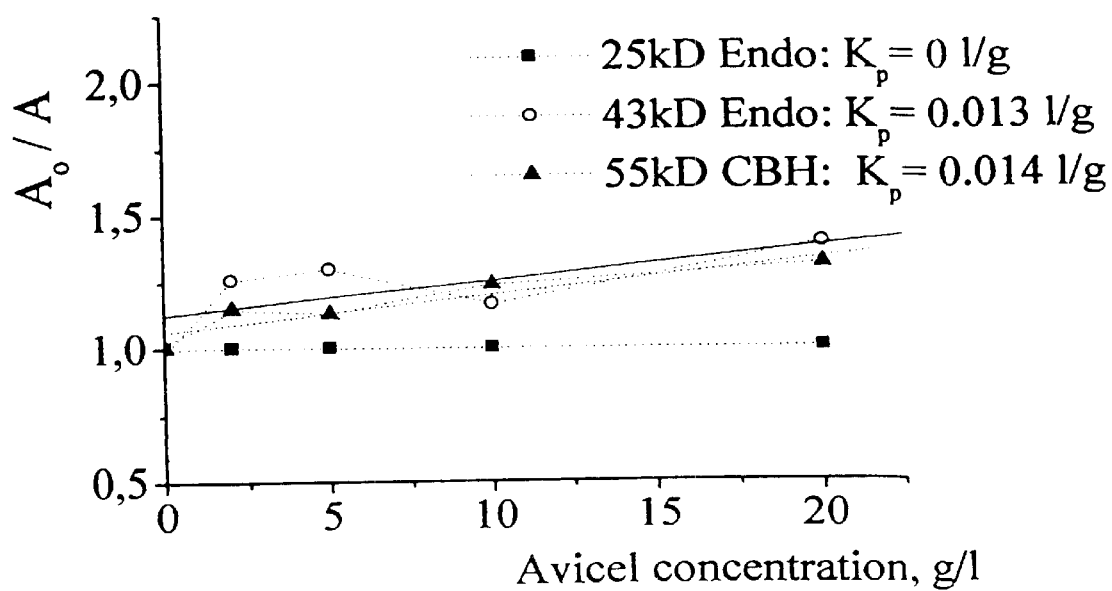
FIG. 35: Adsorption of the enzymes isolated from bound fractions of F-60-8 UF-conc. sample.
Figure 36:
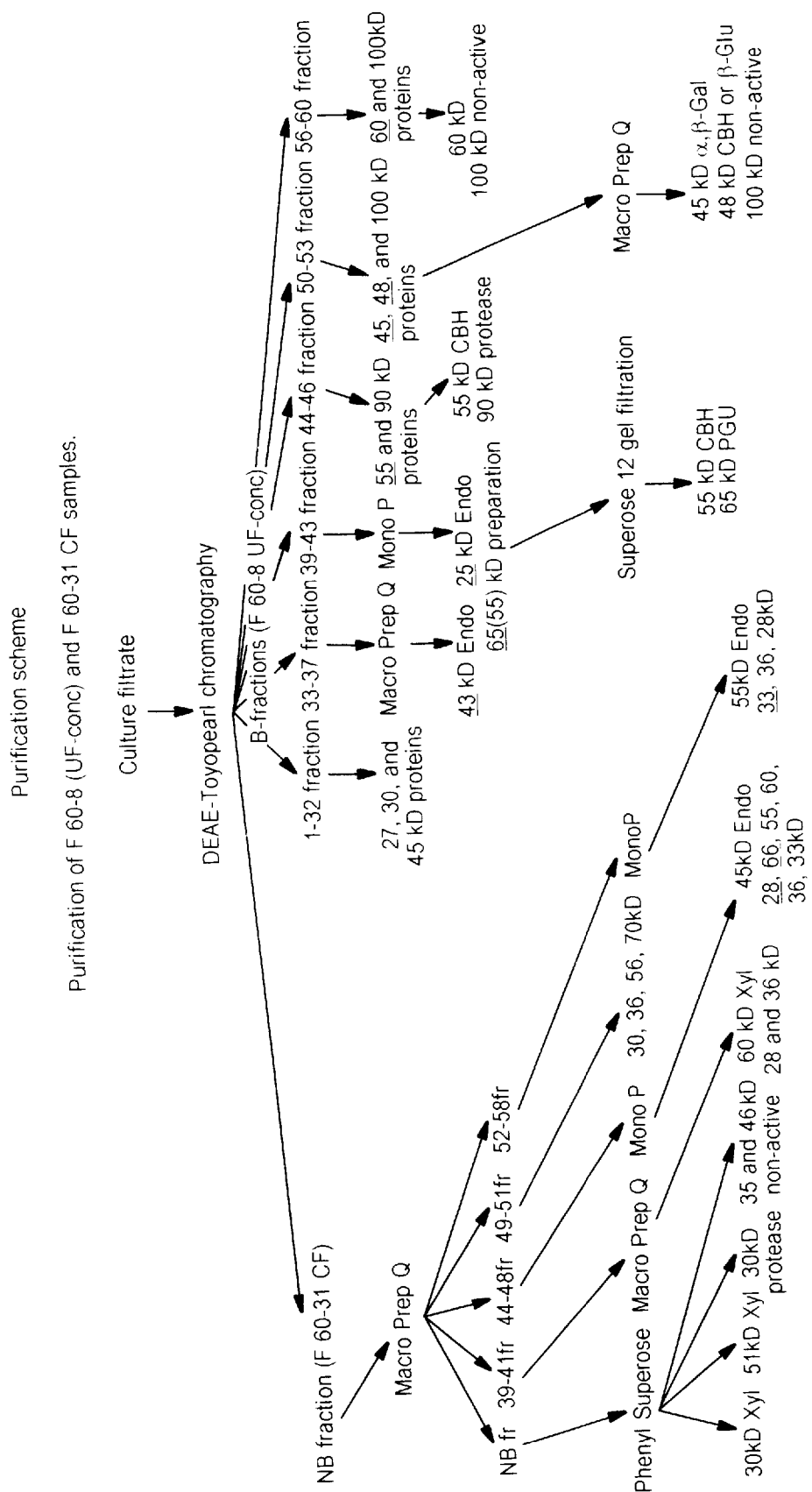
FIG. 36: Purification scheme of F-60-8 (UP-conc) and F-60-31 CF Samples for C1 Protein Isolation.

1. Calmels T. P., Martin F., Durand H., and Tiraby G. (1991) Proteolytic events in the processing of secreted proteins in fungi. J Biotechnol 17(1): p. 51–66.
2. Punt P. J., Dingemanse M. A., Jacobs-Meijsing B. J., Pouwels P. H., and van den Hondel C. A. (1988) Isolation and characterization of the glyceraldehyde-3-phosphate dehydrogenase gene of Aspergillus nidulans. Gene 69(1): p. 49–57.
3. Shoemaker S., Schweickart V., Ladner M., Gelfand D., Kwok S., Myambo K., and Innis M. (1983) Molecular cloning of exo-cellobiohydrolaseI derived from Trichoderma reesei strain L27. Bio/Technology Oct.:691–696.
4. Drocourte D., Calmels T., Reynes J. P., Baron M., and Tiraby G. (1990) Cassettes of the Streptoalloteichushindustanus ble gene for transformation of lower and higher eukaryotes to phleomycin resistance. Nucleic Acids Res 18(13): p. 4009.
5. Mullaney E. J., Hamer J. E., Roberti K. A., Yelton M. M., and Timberlake W. E. (1985) Primary structure of the trpC gene from Aspergillus nidulans. Mol Gen Genet 199(1): p. 37–45.

6. Yanisch-Perron C., Vieira J., and Messing J. (1987) Improved M13 phage cloning vectors and host strains: nucleotide sequences of the M13 mp18 and pUC19 vectors. Gene 33:103–119.
7. Durand H., Baron M., Calmels T., and Tiraby G. (1988) Classical and molecular genetics applied to Trichoderma reesei for the selection of improved cellulolytic industrial strains, in Biochemistry and genetics of cellulose degradation, J. P. Aubert, Editor. Academic Press. p. 135–151.
8. Lowry O. H., Rosebrough N. J., Farr A. L., and Randall R. J. (1951) Protein measurements with the folin phenol reagent. J. Biol. Chem. ?:193–265.
9. Parriche M., Bousson J. C., Baron M., and Tiraby G. Development of heterologous protein secretion systems in filamentous fungi. in 3rd European Conference on Fungal Genetics. 1996. Münster, Germany.
10. Baron M., Tiraby G., Calmels T., Parriche M., and Durand H. (1992) Efficient secretion of human lysozyme fused to the Sh ble phleomycin resistance protein by the fungus Tolypocladium geodes. J Biotechnol 24(3): p. 253–266.
11. Jeenes D. J., Marczinke B., MacKenzie D. A., and Archer D. B. (1993) A truncated glucoamylase gene fusion for heterologous protein secretion from Aspergillus niger. FEMS Microbiol. Lett. 107(2–3): p. 267–271.
12. Stone P. J., Makoff A. J., Parish J. H., and Radford A. (1993) Cloning and sequence-analysis of the glucoamylase gene of neurospora-crassa. Current Genetics 24(3): p. 205–211.
13. Mörsky P. (1983) Turbidimetric determination of lysozyme with Micrococcus lysodeikticus cells: Reexamination of reaction conditions. Analytical Biochem. 128:77–85.
14. Paluh J. L., Orbach M. J., Legerton T. L., and Yanofsky C. (1988) The cross-pathway control gene of Neurospora crassa, cpc-1, encodes a protein similar to GCN4 of yeast and the DNA-binding domain of the oncogene v-jun-encoded protein. Proc Natl Acad Sci U S A 85(11): p. 3728–32.
15. Nakari T., Onnela M. L., Ilmen M., Nevalainen K., and Penttilä M. (1994) Fungal promoters active in the presence of glucose, Patent #WO 94/04673, Alko.
16. Torronen A., Mach R. L., Messner R., Gonzalez R., Kalkkinen N., Harkki A., and Kubicek C. P. (1992) The two major xylanases from *Trichoderma reesei*: characterization of both enzymes and genes. Biotechnology(N Y) 10(11): p. 1461–5.
17. Farkas V. (1985) Novel media for detection of microbial producers of cellulase and xylanase. FEMS Microbiol. Letters 28:137–140.
18. Miller G. L. (1959) Use of dinitrosalicylic acid reagent for determination of reducing sugar. Anal. Chem. 31:426–428.
1. 19.Punt P. J., Mattern I. E., van den Hondel C. A. M. J. J. (1988)A vector for Aspergillus transformation conferring phleomycin resistance. Fungal Genetics Newsletter 35,25–30.

```
SEQ ID No. 1:
CBH1 protein sequence. Signal sequence is
given in italic, the CBD underlined in bold.

MYAKFATLAA LVAGAAAQNA CTLTAENHPS LTWSKCTSGG SCTSVQGSIT      50

IDANWRWTHR TDSATNCYEG NKWDTSYCSD GPSCASKCCI DGADYSSTYG     100

ITTSGNSLNL KFVTKGQYST NIGSRTYLME SDTKYQMFQL LGNEFTFDVD     150

VSNLGCGLNG ALYFVSMDAD GGMSKYSGNK AGAKYGTGYC DSQCPRDLKF     200

INGEAAVENW QSSTNDANAG TGKYGSCCSE MDVWEANNMA AAFTPHPC?V     250

IGQSRCEGDS CGGTYSTDRY AGICDPDGCD FNSYRQGNKT FYGKGMTVDT     300

TKKITVVTQF LKNSAGELSE IKRFYVQNGK VIPNSESTIP GVEGNSITQD     350

WCDRQKAAFG DVTD?QDKGG MVQMGKALAG PMVLVMSIWD DHAVNMLWLD     400

STWPIDGAGK PGAERGACPT TSGVPAEVEA EAPNSNVIFS NIRFGPIGST     450

VSGLPDGGSG NPNPPVSSST PVPSSSTTSS GSSGPTGGTG VAKHYEQCGG     500
```

IGFTGPTQCE SPYTCTKLND WYSQCL * 526

SEQ ID No. 2:
DNA sequence and amino acid sequence of complete Chrysosporium XylF (Xyl1) gene including promoter and terminator sequences. Position of the protein encoding part of the gene is indicated in boid with aminoacid translation below the sequence. Promoter, terminator and intron sequences are given in small case. The signal peptide is shown in italic letters and the cellulose binding domain (CBD) is shown in bold underlined letters.

```
tcatcaacttggcgtttggatgtactaatattacacgtcgtttgcnnagcggagtctgtg      60 tcatctccgtggggtcgggtgctccagacgacgcttcgggccgatcctgaattcgggaag    120 gaaacggttcggctaatcaggtcctctaaaatataacgaagcactacagagggagttcct    180
```

-continued

```
cagaggacatcgtatcaaccgaagaacgaagcgccgaaaggactgatcaaaacaggagta      240 ggtagggatgtgtgagtacctaaactttccatacctgacataaaatcatcatggtgcttc      300 agacctgtttgatgaggcgagggcggaggccgcattgtattttcgttccttccttctttt      360 tgttagtatatctnagggttccatcgtaaaatggaatcttccagctctactagtaattag      420 aacaatagttctgatgtcgtgcgccaagcttttcagatgactgccaaaaacccatcatg       480 ggtatggacaaaagcagtaatcggagtcacaacgccgcattttccttcatgatttccgtc      540 aaccggagaggtcggaggaggactccggccacatgtgatgcgaagaagtacatggcgcca      600 tggttctaacctcttatagtctgaaaatgcgcggaggccagcgaagccaagcccgggaac      660 cgttcttgtcatggtttcagtattgtttcgctaaacattctatccgattcgcgataggtg      720 cggctgccaccgaaggttgtatccttaaagctttggtaagtacggagtacggaaatggaa      780 acgcgccgcagtcctggttccatcggtatcctccgcatgctccgccaaaaaagaaaacc      840 cgggtatgtttacaaaggatataagagacaagatgcaccacccgcccccttcccatctgc      900 cggttgcccacgtcgccgtcgactgcttgtccgcttcctacctgcagcctcttcagaga      960 ccatcaaacATGCGTACTCTTACGTTCGTGCTGGCAGCCGCCCCGGTGGCTGTGCTTGCC     1020
           M   R   T   L   T   F   V   L   A   A   A   P   V   A   V   L   A CAATCTCCTCTGTGGGGCCAGTgtatgtaattgccttactcggaaaatagtcaccactag     1080
 Q   S   P   L   W   G   Q   C agggacttaagctcactacttcctgtttcacaatagGCGGCGGTCAAGGCTGGACAGGTC     1140
                                      G   G   Q   G   W   T   G CCACGACCTGCGTTTCtGGCGCAGTATGCCAATTCGTCAAgtcagtaactgcttttatt     1200
 P   T   T   C   V   S   G   A   V   C   Q   F   V   N tcttttctctctgggattacgatttcgttttgcacttagcttggttctgcatttcattgt     1260 tgtattgttctcttttgtgtgtgagaggttttattaccacctaaaggccatttgctaac      1320 aaatctccccagTGACTGGTACTCCCAATGCGTGCCCGGATCGAGCAACCCTCCTACGGG     1380
             D   W   Y   S   Q   C   V   P   G   S   S   N   P   P   T   G CACCACCAGCAGCACCACTGGAAGCACCCCGGCTCCTACTGGCGGCGGCGGCAGCGGAAC     1440
 T   T   S   S   T   T   G   S   T   P   A   P   T   G   G   G   S   G   T CGGCCTCCACGACAAATTCAAGGCCAAGGGCAAGCTCTACTTCGGAACCGAGATCGATCA     1500
 G   L   H   D   K   F   K   A   K   G   K   L   Y   F   G   T   E   I   D   H CTACCATCTCAACAACAATGCCTTGACCAACATTGTCAAGAAAGACTTTGGTCAAGTCAC     1560
 Y   H   L   N   N   N   A   L   T   N   I   V   K   K   D   F   G   Q   V   T TCACGAGAACAGCTTGAAGTGGGATGCTACTGAGCgtgagtgacctctcctccttctccc     1620
 H   E   N   S   L   K   W   D   A   T   E   P gacaataatagataattacgagccggttcgaggctgacattgcgcgattctagCGAGCC      1680
                                                        S   R GCAATCAATTCAACTTTGCCAACGCCGACGCGGTTGTCAACTTTGCCCAGGCCAACGGCA     1740
 N   Q   F   N   F   A   N   A   D   A   V   V   N   F   A   Q   A   N   G   K AGCTCATCCGCGGCCACACCCTCCTCTGGCACTCTCAGCTGCCGCAGTGGGTGCAGAACA     1800
 L   I   R   G   H   T   L   L   W   R   S   Q   L   P   Q   W   V   Q   N   I TCAACGACCGCAACACCTTGACCCAGGTCATCGAGAACCACGTCACCACCCTTGTCACTC     1860
 N   D   R   N   T   L   T   Q   V   I   E   N   H   V   T   T   L   V   T   R GCTACAAGGGCAAGATCCTCCACTGGGACGTCGTTAACGAGATCTTTGCCGAGGACGGCT     1920
 Y   K   G   K   I   L   H   W   D   V   V   N   E   I   F   A   E   D   G   S CGCTCCGCGACAGCGTCTTCAGCCGCGTCCTCGGCGAGGACTTTGTCGGCATCGCCTTCC     1980
 L   R   D   S   V   F   S   R   V   L   G   E   D   F   V   G   I   A   F   R GCGCCGCCCGCGCCGCCGATCCCAACGCCAAGCTCTACATCAACGACTACAACCTCGACA     2040
 A   A   R   A   A   D   P   N   A   K   L   Y   I   N   D   Y   N   L   D   I
```

```
TTGCCAACTACGCCAAGGTGACCCGGGGCATGGTCGAGAAGGTCAACAAGTGGATCGCCC   2100
 A  N  Y  A  K  V  T  R  G  M  V  E  K  V  N  K  W  I  A  Q

AGGGCATCCCGATCGACGGCATCGGCACCCAGTGCCACCTGGCCGGGCCCGGCGGGTGGA   2160
 G  I  P  I  D  G  I  G  T  Q  C  H  L  A  G  P  G  G  W  N

ACACGGCCGCCGGCGTCCCCGACGCCCTCAAGGCCCTCGCCGCGGCCAACGTCAAGGAGA   2220
 T  A  A  G  V  P  D  A  L  K  A  L  A  A  A  N  V  K  E  I

TCGCCATCACCGAGCTCGACATCGCCGGCGCCTCCGCCAACGACTACCTCACCGTCATGA   2280
 A  I  T  E  L  D  I  A  G  A  S  A  N  D  Y  L  T  V  M  N

ACGCCTGCCTCCAGGTCTCCAAGTGCGTCGGCATCACCGTCTGGGGCGTCTCTGACAAGG   2340
 A  C  L  Q  V  S  K  C  V  G  I  T  V  W  G  V  S  D  K  D

ACAGCTGGAGGTCGAGCAGCAACCCGCTCCTCTTCGACAGCAACTACCAGCCAAAGGCGG   2400
 S  W  R  S  S  S  N  P  L  L  F  D  S  N  Y  Q  P  K  A  A

CATACAATGCTCTGATTAATGCCTTGTAAgaggaggtatattatttttagaggcaatgaa   2460
 Y  N  A  L  I  N  A  L  * gctaggaggaaagaggggaagtgaggtaattagctaggacaggcaaatctagcagcaatt   2520 ataagtcaacactatataaaatattcctataatggcttgtgcttcggtgtgcaaaaaaaa   2580 aaaaaaaaaaaaaaaaaaaaaaaaaaaaaaactcaaaaacaaaaatgatccaacatgatt   2640 cgaaatggcgaccttgcaaatgcacacctcagataataccactatacaatacaccttaaa   2700 tggcacctaaatccatttgtctgcggtcatagacggggcttaagaagcctgggatgcagg   2760 tgtcgatgcaagggttacgtcagtgtatgatatgagtatgaaccatgctgtctgggtaat   2820 tctccactttccctccccttacgactcttcgggtgtgcctctctagaaagtcgactcctg   2880 gcgcctcagatcgccctttggctctgttcggtacaatgacgtccgctggtttcttccaaa   2940 gaccaggtatttctcccgtggcaacaaagaataccaaatacctatatcgaaccgtagtct   3000 tctgataattagatgtctctcaaggcgcgg   3030

SEQ ID No. 11:
XylF protein sequence. Signal sequence is given
in italic, the CBD is underlined in bold.

1 MRTLTFVLAA APVAVLAQSP LWGQCGGQGW TGPTTCVSGAVCQFVNDWYS

51 QCVPGSSNPP TGTTSSTTGS TPAPTGGGGS GTGLHDKFKA KGKLYFGTEI

101 DHYHLNNNAL TNIVKKDFGQ VTENSLKWDA TEPSRNQFNF ANADAVVNFA

151 QANGKLIRGH TLLWHSQLPQ WVQNINDRNT LTQVIENHVT TLVTRYKGKI

201 LHWDVVNEIF AEDGSLRDSV FSRVLGEDFV GIAFRAARAA DPNAKLYIND

251 YNLDIANYAK VTRGMVEKVN KWIAQGIPID GIGTQCHLAG PGGWNTAAGV

301 PDALKALAAA NVKEIAITEL DIAGASANDY LTVMNACLQV SKCVGITVWG

351 VSDKDSWRSS SNPLLFDSNY QPKAAYNALI NAL*

SEQ ID No. 3:
DNA sequence and amino acid sequence of complete
Chrysosporium EG3 gene including promoter and terminator
sequences. Promoter, terminator and intron sequences
are given in small case. Putative glycosylation site is given
with an asterisk (*). The signal peptide is shown in italic
letters and the propeptide is shown in underlined letters.

ccgccctggagcgtggaccgtggggacaggcggcaaatgagaccctattgggggcgcatcg   60 acggtgcagaaccgaggttccgggaccttggcagagcggcccagggaccccgccatccag   120 ctatgcgcctccacagaagccgaccgatgctcggttgcatcccgagatcgtcggtatta   180 aggagagggggagaagaagaagggggggggggggggggaatgagacaacaacactcaggcg   240 cgccaattagaacttcaacgagcctccttcctgcatccagacaagaccgaggtcgagccg   300
```

-continued

```
ggtactatgcaagcgtcccgtgccgcgtgatgtcgctcgtaggtgttgacaggttctcag    360 ctgtttcttgaatcccgggaggtggactaaaggggcaagagaccatggtaagctccgtc    420 gccagccctcccgttgcggagcggaagccgaggaccgaccttcttctggagaacccgggc    480 tgcccggcggaggcgggttccgccttttttttaaccagtccgagttgttgtcgcgaact    540 gcgctcggttgcaacgtcagtgtccaatcggcaggcgtatcgcgacccggtaaggggtt    600 acggcatgtgttctcggcttccgcacatcaaaacttactcgtattcgtcctgaccttggt    660 aattaattatgtcgcaagacaaggagttgtttgagacgactccggcgcgcataattacac    720 agtggtgcagtattatatatctttctcccgtagggacgacgacaaagacccgtcagtgat    780 taataataattagtagcagtttctttctttcaagactcaagaatactcctttccgccatc    840 gtggcagcgtttagattcatcATGCAGCCGTTTCTGCTCTTGTTCCTCTCGTCGGTCACG    900
                      M  Q  P  F  L  L  L  F  L  S  S  V  T GCGGCGAGCCCCCTGACGGCGCTCGACAAGCGGCAGCAGGCGACGTTGTGCGAGCAGTAC    960
 A  A  S  P  L  T  A  L  D  K  R  Q  Q  A  T  L  C  E  Q  Y GGCTACTGGTCGGGCAACGGTTACGAGGTCAACAACAACAACTGGGGCAAGGATTCGGCC   1020
 G  Y  W  S  G  N  G  Y  E  V  N  N  N  N  W  G  K  D  S  A TCGGGCGGCCATCAGTGCACCTACGTCGACAGCAGCAGCTCCAGCGGCGTCGCCTGGCAC   1080
 S  G  G  H  Q  C  T  Y  V  D  S  S  S  S  S  G  V  A  W  H ACGACCTGGCAGTGGGAAGGAGGCCAGAACCAGGTCAAGAGCTTCGCCAACTGCGGCCTG   1140
 T  T  W  Q  W  E  G  G  Q  N  Q  V  K  S  F  A  N  C  G  L CAGGTGCCCAAGGGCAGGACCATCTCGTCCATCAGCAACCTGCAGACCTCCATCTCGTGG   1200
 Q  V  P  K  G  R  T  I  S  S  I  S  N  L  Q  T  S  I  S  W TCCTACAGCAACACCAACATCCGCGCCAACGTGGCCTACGACCTCTTCACCGCGGCAGAC   1260
 S  Y  S  N  T  N  I  R  A  N  V  A  Y  D  L  F  T  A  A  D CCGAACCACGCGACCAGCAGCGGCGACTACGAGCTCATGATCTGgtcagtttttttttc   1320
 P  N  H  A  T  S  S  G  D  Y  E  L  M  I  W ttttttcttttcttctcttttcttttcttttcctttctcctgttttattttcttatccat   1380 tgcttcgccctctttccttaaccctgctgactctctcttcttgtcaatgatactgtaata   1440 gGCTGGCGAGATTCGGCGACGTCTACCCCATCGGCTCGTCCCAGGGCCACGTCAACGTGG   1500
  L  A  R  F  G  D  V  Y  P  I  G  S  S  Q  G  H  V  N  V

CCGGCCAGGACTGGGAGCTGTGGACGGGCTTCAACGGCAACATGCGGGTCTACAGCTTCG   1560
 A  G  Q  D  W  E  L  W  T  G  F  N  G  N  M  R  V  Y  S  F

TAGCGCCCAGCCCCCGCAACAGCTTCAGCGCCAACGTCAAGGACTTCTTCAACTATCTCC   1620
 V  A  P  S  P  R  N  S  F  S  A  N  V  K  D  F  F  N  Y  L

AGTCCAACCAGGGCTTCCCGGCCAGCAGCCAATACCTTCTCAgtaaggagacgagatctc   1680
 Q  S  N  Q  G  F  P  A  S  S  Q  Y  L  L  I gaacagcataccatatatgcgtgcggtacaagtgcactaaccccctttttttttcccgttc   1740 gcagTCTTCCAGGCGGGCACCGAGCCCTTCACCGGCGGCGAGACCACCCTTACCGTCAAC   1800
    F  Q  A  G  T  E  P  F  T  G  G  E  T  T  L  T  V  N AACTACTCTGCAAGGGTTGCTTAAacaggaaggccgaggatggccccaaggccgttgcg    1860
 N  Y  S  A  R  V  A  * ggttcacgagctctcttcttttcaagtgctgtacatacataattagcgtaccaagtcata   1920 gctgtttgtcagcttcaaactaagtgctcgcccacaaaagagggggagggaaaataac   1980 aaattgccgaacgcagtgataagcttctgggagcgttgaaagcagtctacagtaggtggc   2040 tgyacgaaggaaaagagtgccttattaaagctatctacaaaggagacaaaacgactgata   2100 tttatggacaaagggactggccaatgcgttaaacagcctcatacagctgtagcatatata   2160 tggctaatacgtttggaagctctatagcttccgacacaccccctagttaaacgtagtagt   2220 cgtttaactacgctttgyggtgatactgttcttggtattatatcctttgtcgctcttacc   2280
```

-continued

```
tcgatagctccttcagggggcctgccttctgtattcggaagtctaaaagagtcgagtata    2340 gtagagcgattcctttaaagctatagatcaaatatggccattataactatagtagtaata    2400 gtattactagttttaatcataatagtaataataggatgacgcctcttatgcttgaatcaa    2460 tagatgactcgttaggtctacctattacaaacactataactgctagtaggtcgactcctg    2520 ctcctataacacctcgtaagtataagtatactaaagcttctataccgtaagtgttcctat    2580 tgtccctatttgattaactttattactagttttgtagttttcttagtagttctagcgatt    2640 taagcgagtttacgtggttcggcttcttctggttaatttgatagcgactctatcacagtt    2700 tctagcgctttactagtcacgtctagatcgtttaagctgactaaatatagcaacatcgaa    2760 gctagcgagctttgtaaggtaccctatagaatatatatacggtcggctctagtaggacgt    2820 tcttttagcaaatgtcacgatcattccggcgttagctcctactattactattataccta    2880 agttcctataagtgtagggagatatacgttaatcgcctatacgtctaatagctcttataa    2940 tacttatactaactataatggtagtcttgcttcttatattaggtcggctaaggacttaac    3000 gaaggctctaatggatagagctaaggcttctataag    3036
```

SEQ ID No. 12:
EG3 protein sequence. Signal (prepro)sequence is given in italic, the putative pro sequence underlined italic

```
  1  MQPFLLLFLS SVTAASPLTA LDKRQQATLC EQYGYWSGNG YEVNNNNWGK

51  DSASGGHQCT YVDSSSSSGV AWHTTWQWEG GQNQVKSFAN CGLQVPKGRT

101  ISSISNLQTS ISWSYSNTNI RANVAYDLFT AADPNHATSS GDYELMIWLA

151  RFGDVYPIGS SQGHVNVAGQ DWELWTGFNG NMRVYSFVAP SPRNSFSANV
                                                       *

201  KDFFNYLQSN QGFPASSQYL LIFQAGTEPF TGGETTLTVN NYSARVA*
```

SEQ ID No. 4:
DNA sequence and amino acid of partial Chrysosporium GPD gene including promoter sequences. Promoter and intron sequences are given in small case. The 3' end of the gene is lacking.

```
tgagcagcaatgagcagcaatgagcattcctgggccaccgagtctgagtgccagtacgga      60 gtatcgtacttcgtaccggggtttgatttggtgacggtgcttttcacctctcgatgcccg     120 aaatcgggtctaagctgagtttgatcaaatatgtgactccaacatcgcccccttcggcaa     180 accccgtcgacacgtgtgtcatccttccattgcaagcgatcactcgcagggcgtgacgat     240 gaacgagattttttgcccggaccgattcgcggatatagcggcagccgaccagcccaccac     300 actgatggccgtgtcactagtgtatgctcccagaaccgcaagcatacactgggcaatgct     360 tggtatgcagttgaggcagctttatgtttccataccctctccacttcggctcggggactcg     420 gcggggtcgcggaagtttgacggcagccgtcgggccttaggccgagattaccgtggttgt     480 ggcccagttttagccgttcccgtccgtttcctaccggaccatgattttcgtgaaccattg     540 caatcccgaagcgcatttccgacgttaaggagttacctccgctgcccagaattcatgatc     600 gtggccggctcaaggcagcgtggcggggcatccgtgtcaagctcccaggaggaggtgcgc     660 gatttcaaatccgggccaaaacaggccaagactggctggccaaaaaaggagcgtagacg     720 gcccgggacatcggacgtcagctcgcagccacccaaaaccggtccgatctactcgcttac     780 tgtggtagttcaggtacttttgagtagtaaaaacgctacggcagggccgggggttcccc     840 ggtgacggaggtgcctctgcggtggcgaacatcccacgcactctcgagctacggtgacac     900 ctcgtgtcctgttggtcttgcaatgctgggcggcaggaaatgcgtcgcgctcctcccgg     960 ccaagacctaaaacagacagcgccgcaaagtcgctcactagcaccgcgaaacgaagatgc    1020
```

```
cccacctcaacgcaatctgtgatgcaagcaattgggaaggctcaccccacctcagcgagg     1080 ggctcaaccattttttattatcagctcatgccaccacaacatgactgttttctttccttgc    1140 tcatcccacatttgacaaaaatcgtcgattaatctctttccatacaggccgtccgcgctc    1200 tgataaccacataaaagtctcttcagtcaacagctcaaagctccctcatccctccaggta    1260 agcagccaaagagctcccccacggaccccgcactgcctcatcccgcctgtatcggacctg    1320 cgcgacccagcagagaatcccaaacctttgctgcttgctgcccggttccggactgagctg    1380 caacccaagcctttaaaaagcttttcccttctcccacggtgtcaactctgtcctatccct    1440 ccgacatccgttgagctcaacaactccccgaaccttttaccccgcgccgagctacccctc    1500 catcaaaccaccctgacagctcgctcactcacctccccacatcacagaaatcaaaATGAC    1560
                                                       M  T
```

```
TATCAAGGTCGGCATCAACGGTTTCGGCCGTATCGGCCGTATCGTCTTCCGCAACTCCAT    1620
 I  K  V  G  I  N  G  F  G  R  I  G  R  I  V  F  R  N  S  I

CGAGCACTCGGATGTCGAGATCGTTGCCGTCAACGACCCCTTCATTGAGCCCAAGTACGC    1680
 E  H  S  D  V  E  I  V  A  V  N  D  P  F  I  E  P  K  Y  A

Tgtaagtagttttttttttccttcctcgcgttctttcctgttccatcgacagtacgagat    1740

GatcttgcaggcggatcggagctaaccgcgattgtcgtacagGAGTACATGCTCAAGTAT    1800
                                            E  Y  M  L  K  Y GACTCGACCCACGGTATCTTCAACGGCACCATCGCCGTCGAGGGCAACGACCTCATTGTC    1860
 D  S  T  H  G  I  F  N  G  T  I  A  V  E  G  N  D  L  I  V AACGGCAAGAGGGTCAAGTTCTACACTGAGCGGGMCCCCGCCAACATTCCCTGGARGGAA    1920
 N  G  K  R  V  K  F  Y  T  E  R  ?  P  A  N  I  P  W  ?  E ACTGGTGCCGAGTACATMRTCGAGTCGACCGGTGTGTTCACCAMCACCSAGAAGGCTAGC    1980
 T  G  A  E  Y  I  ?  E  S  T  G  V  F  T  ?  T  ?  K  A  S GCCCACCTCAAGGGCGGCGCCAAGCGCGTCATCATCTCTGCTCCCTCGGCCGATGCCCCC    2040
 A  H  L  K  G  G  A  K  R  V  I  I  S  A  P  S  A  D  A  P ATGTACGTCATGGGCGTCAACGAGAAGACCTACGACGGCAAGGCCCAGGTCATCTCTAAC    2100
 M  Y  V  M  G  V  N  E  K  T  Y  D  G  K  A  Q  V  I  S  N GCCTCGTGCACCACCAACTGCCTGGCTCCCCTCGCCAAGGTCATCCACGACAAGTTCGGC    2160
 A  S  C  T  T  N  C  L  A  P  L  A  K  V  I  H  D  K  F  G CTCGTTGAGGGTCTCATGACCACCGTCCACTCCTACACTGCCACCCAGAAGACCGTCGAT    2220
 L  V  E  G  L  M  T  T  V  H  S  Y  T  A  T  Q  K  T  V  D GGTCCCTCTGCCAAGGACTGGCGTGGTGGCCGTGGTGCTGCTCAGAACATCATCCCCAGC    2280
 G  P  S  A  K  D  W  R  G  G  R  G  A  A  Q  N  I  I  P  S AGCACTGGCGCCGCCAAGGCCGTCGGCAAGGTCATCCCTGAGCTCAACGGCAAGCTCACC    2340
 S  T  G  A  A  K  A  V  G  K  V  I  P  E  L  N  G  K  L  T GGCATGTCCCTCCGTGTCCCCACCCCCAACGTTTCCGTTGTCGACCTCACCTGCCGCCTC    2400
 G  M  S  L  R  V  P  T  P  N  V  S  V  V  D  L  T  C  R  L GAGAAGGAGGCTACCTACGACGACATCAAGGCCGCCATCAAGGAGGCCGCCGCCGGCCCC    2460
 E  K  E  A  T  Y  D  D  I  K  A  A  I  K  E  A  A  A  G  P CTCAAGGgtgagttatctggttcctttttttttttggagaacgacacatgctgataaa    2520
 L  K  G acccagGCATCCTCGACTACACTGAGG  2547
       I  L  D  Y  T  E
```

SEQ ID No. 13:
GPD protein sequence (the C-terminus is lacking in the
sequence available).

MTIKVGINGF GRIGRIVFRN SIEHSDVEIV AVNDPFIEPK YAEYMLKYDS

THGIFNGTIA VEGNDLIVNG KRVKFYTER? PANIPW?ETG AEYI?ESTGV

FT?T?KASAH LKGGAKRVII SAPSADAPMY VMGVNEKTYD GKAQVISNAS

-continued

```
CTTNCLAPLA KVIHDKFGLV EGLMTTVHSY TATQKTVDGP SAKDWRGGRG

AAQNIIPSST GAAKAVGKVI PELNGKLTGM SLRVPTPNVS VVDLTCRLEK

EATYDDIKAA IKEAAAGPLK GILDYTE
```

SEQ ID No. 5:
C1-EG5 "25kD" (Family 45) gene obtained by PCR
based on "25kD Endo" protein sequencing and
family 45 homology analysis.

```
-3309                                      GCTTAGGAG  -3301

AATCACGAGAAGCTAATTGGGCTCTATAGTATCCGACAAGATGACCCAGAGCGAGATTGA  -3241

GGATCTCGAGGGAACCCTGAAGCAGAGCAGCAACAACGACACCAGCCTCCTCCGCGACCT  -3181

GCTCGACAAGATTCCCGATGGCCTCCTCGGCGGCAACAACAAATCCAAGCTGGACGATAT  -3121

CCAGAGCAACGCGCAGGCCGCGCAGATGGAGAACCTGAGCGTCTCGCCGCGGGAACCCGA  -3061

GGAGCTGACCAGATACGTCCAGGAAGTGTTCCGTCAGATCATGCCCGCCATCAAGTTCCA  -3001

TGACCAGCTTCTCCAGGACATCTCGGAGGCCATCGACAAGATCCCGGTGCTGCCCAAGAT  -2941

TGTGGAGCAGCTGGAGGAGCAGATGTCCATCTTTGTATTCCAGATCATGGCCCCGTTCGT  -2881 creA

GGTTCCGCTTATCGAGCAGATCAAGAACGAGCTCGCGACTGGCTCCAGCGAGATCATCCA  -2821

GAGCAGCAGGGCTGAGCAGCACAACGTCTTTGAGGACGACAACGCCACCGACCCGACTCA  -2761

CTCGATGTTGGCCAAGGACCACTTTAGTAACGTAAAGCCGACCCTAATCAGAAGCTCGCA  -2701

TGTAGAATTGAGTTAGACTGACGCGACTTGTTTCCCGTCTCTGTAGATCCTCAACGAGAT  -2641

CGGCGGTCGCGCCGCCTCCAAGGTCGTCTCCTGGGTCGTCCCGCAGCTCATGGAGGCCTG  -2581

GGACGATGACAGCGTCGACGTGGACCGCCTGCTTGACAAGATCATTTACGGAGTGTTCCA  -2521

CCATCCCGCGCAGCGCACCATGGGCCCTGAGGGGCGTCCGAGGGCCGGGAGCTCATCTT  -2461

CAACATGGTGCGCGAGTGGTGGGAGGACATGAGCGACGGGCAGCGCGACGAGTACCGGGG  -2401 creA

CAAGCTGAGCCGCGAGGGAGTCGAGAGAGGCGACAACCACCGCGAGGGCCAGCACGACTG  -2341

CGGCCACGGCTGCGGGGGCAAGCTCAAGATGCACAAGAACTTCCGGAACGAGGCGCCCCA  -2281 creA

GACGGTAGAGGACCAGATCGCGGGCGCCGCCGCGGAGGCCATCATGGGAGGCGTCAAGCA  -2221 creA

GGGCCTGTCGCAGGCCGTGCAGAACGCCGCCGGCCGCCAGGAGTCGTCGGAGAGCAGCGG  -2161

CCTGGGTGGGTTCATCAGCAGCGTCGCGGGCGGCCTCCTGGGCGGCGCCCTCAAGAGGGA  -2101

CGAGACAGAGTCGTACCAGGCCGGCGGCCGCACCGAGGACGGCGGGTACACGCAGACCAC  -2041

GACCGAGTACGGCTACTCCGGAGGCCGCTACGGCCAGGCCCAGTACACGGAGACGCAGTA  -1981

CGGCGGCGGCGGCGGCGGCCGCAGCGAGTACCGCCGCTACGAGCAGCGCGAGGATGATGA  -1921

CGGCCGGGTCCAGAGCTACGGATACACGGAACAGCGCACCGAGACGCGCTACGACAGCTA  -1861

CTCGGGTGGCTATGGCGGCCGCGAGGAGACCAGCAGCTATGGCGGCGGCGGCAGCGCGAG  -1801

CGAATACATTCGTAGCTCCCAGCAGAGTAGCTACGGTGGCAGCGGCTATGGCAGTGGGTA  -1741

CGGTCGTCGTGATGAAGAAGAGAGCAGCGGCTATGGAAGTGGTTACGGTCGTCGTGATGA  -1681

AGAGGAGAGTGGTGGTTATGGTGGCGGCTATGGCCGCCGTCAGGAAGAAGAGAGTAGCAG  -1621

CTATGGAAGCGGTTATGGTCGTCGTCGTGATGAAGAAGAGAGCGGCGGTTATGGTGGTGG  -1561

CTACGGCCGCCGTCAGGAAGAAGAGAGTAGCGGCTATGGAAGTGGTTACGGTCGTCGTGA  -1501
```

```
TGAAGAAGGGAGCGGCGGTTATGGTGGTGGCTACGGCCGCCGTCATGAGGAAGAGAGCAG    -1441

TGGTTACGGCAGCGGCTATGGTCGTCGCCATGAAGAGGAGGGCGGTGGCTACGGCAGTGG    -1381

TTACGGCCGCCGGCGCAACGACGAGGAGGAAGAGGAGGATGGCGGACGCCGGAGGTGGGG    -1321 creA

TTACTAGGGTGAACTCTTCCGGCCGGTCTCTTGTTGTGAACCTTGCTGTTGCATGGGCAG    -1261

GACCGGTGCATCATGAACAGGACGGTGCGCTGTGTTTTTTTTTCTCGGGGTCTTGATTG    -1201

TTTGTTGAATCTCCCTTTTCGAGGATACGAGCTCTCTCGGGGACGAATAGATGAAGGCAA    -1141

TCTGACAGATTTGCTCTCAAAAAAGACTGATATCTCTTCCACCATGCACTGTATGTACA    -1081 nit2

TTACATACATTATCCCCCTCCACTGGATTCGCACAACGGAAAGCAATGGCGCGCTGATTC    -1021

AAGAACCATCAGGGCTGTCATTGGCTTGTTTTGTGCCGTGGCCGCGGTGACGCCCACTAT    -961

GACTCTCTGGGCAGGCGGCAACTGGGTGCCAGATATATTAATCCGGGCATAGCGCATAT    -901 creA

CTTCCTTGATTTGTAGAGTACTAGTACACTAACCCCCTTCTCCACATGGGGCCACTGTTC    -841 nit2

GGTAGATCTGCCCGAAGTGCAAGTGCGGGGGGGGCCAAACTAGGTAATATCCTCCCGCTC    -781 creA

TCCCGAGTGCGCGGACTAACCGTCATTGCTCCCAGAGGCTTGCACTCTATCGCAGGCCTT    -721 nit2

TTCCAATAAGGATGGGCGTTCGGCGGTGATGATGCCGGTCGTGCGGGCATACGGGAG      -661 creA

GGTAGATAGAAAATAACGACGCTGGTGTTTTGGAGAGGGGAGGGGGACTATTAGGGGAGG   -601 creA    nit2

GAAATACAGGGGCAGGGGTGAGACGGGTGACGTTCCGGCGGAACCTCGCGCTTGTGAAA    -541

CAAGCAGCCCTGTTAGGTTGCTCTAGACTAGTGTACATACATACATATGTACATACTGTA   -481

TGTACTGCACATACTTTAACTTGGTGCTTCCCTGTGAGCCGCCAGGAACATCACAACTGC   -421

AAGCGGAAAAGGCCCCATATACGGGGCGGCTTGTCGGGATGGCTCCCCCCTTCGGAACGG   -361

GTCTGACTTCCGAGGATTTTACCTGCTTCATTTGGGTATTCTGCGATGGCCTGTTCAACC   -301

CTTCCCCTGGCCGAACCGTTTCTTGGCTCGATCCTAGTGTACACTACACTACTCGTAGAC   -241

TGCCTGCCCGACGATCCGCGGGAACGGGCCAGGAGTGTGGAGTGGAGACGGGCGGCGGTG   -181 creA

ATGTCGTGTAATTAAATATATAAGTGAGAGTGTTTTTTGACTGCCCCGGGTTCTGGTAGT   -121

TATA box

TGAAGGGAAGTTCGATGCTCTCTGCTGTCGTCGCTCTCGTCGCTCTCGTCGGCATCCTCC   -61

ATCCGTCCGCCTTTGATAACCCGCTCCCCGACTCAGTCAAGACGACGCATACTTGGCACC   -1

ATGCATCTCTCCGCCACCACCGGGTTCCTCGCCCTCCCGGCCCTGGCCCTGGCCCAGCTC   +60

Put.SS

M   H   L   S   A   T   T   G   F   L   A   L   P   A   L   A   L   A   Q   L    20

TCGGGCAGCGGCCAGACGACCCGGTACTGGGACTGCTGCAAGCCGAGCTGCGCCTGGCCC   +120
 S   G   S   G   Q   T   T   R   Y   W   D   C   C   K   P   S   C   A   W   P    40
```

```
                                          -continued
GGCAAGGGCCCCTCGTCTCCGGTGCAGGCCTGCGACAAGAACGACAACCCGCTCAACGAC    +180
 G  K  G  P  S  S  P  V  Q  A  C  D  K  N  D  N  P  L  N  D       60

GGCGGCTCCACCCGGTCCGGCTGCGACGCGGGCGGCAGCGCCTACATGTGCTCCTCCCAG    +240
 G  G  S  T  R  S  G  C  D  A  G  G  S  A  Y  M  C  S  S  Q       80

AGCCCCTGGGCCGTCAGCGACGAGCTGTCGTACGGCTGGGCGGCCGTCAAGCTCGCCGGC    +300
 S  P  W  A  V  S  D  E  L  S  Y  G  W  A  A  V  K  L  A  G      100

AGCTCCGAGTCGCAGTGGTGCTGCGCCTGCTACGAGCTGACCTTCACCAGCGGGCCGGTC    +360
 S  S  E  S  Q  W  C  C  A  C  Y  E  L  T  F  T  S  G  P  V      120

GCGGGCAAGAAGATGATTGTGCAGGCGACCAACACCGGTGGCGACCTGGGCGACAACCAC    +420
 A  G  K  K  M  I  V  Q  A  T  N  T  G  G  D  L  G  D  N  H      140

TTTGACCTGGCCgtgagttgcctcccCttctccccggaccgctcagattagatgagatta    +480
             Intron 1
 F  D  L  A                                                       144 gactttgctcgtaaatcggtccaagattcccttgactgaccaacaaacatcatacgggca    +540 gATCCCCGGTGGCGGTGTCGGTATTTTCAACGgtaagctggtgccccggaccCctcccc    +600
                                 Intron 2
 I  P  G  G  V  G  I  F  N                                       154 ggaccCctcccccttttcctccagcgagccgagttgggatcgccgagatcgagaactcac    +660 acaacttctctctcgacagCCTGCACCGACCAGTACGGCGCTCCCCCGAACGGCTGGGGC    +720
                    A  C  T  D  Q  Y  G  A  P  P  N  G  W  G     168

GACCGCTACGGCGGCATCCATTCCAAGGAAGAGTGCGAATCCTTCCCGGAGGCCCTCAAG    +780
 D  R  Y  G  G  I  H  S  K  E  E  C  E  S  F  P  E  A  L  K      188

CCCGGCTGCAACTGGCGCTTCGACTGgtacgttgctttgacataccggaacccaattcct    +840
                           Intron 3
 P  G  C  N  W  R  F  D  W                                       197 ccaaccccccccttttctccccaactccgggggtagtcggaatgtcgcgactgaccct     +900 atttcagGTTCCAAAACGCCGACAACCCGTCGGTCACCTTCCAGGAGGTGGCCTGCCCGT    +960
        F  Q  N  A  D  N  P  S  V  T  F  Q  E  V  A  C  P        214

CGGAGCTCACGTCCAAGAGCGGCTGCTCCCGTTAAGAGGGAAGAGAGGGGGCTGGAAGGA   +1020 t25

S  E  L  T  S  K  S  G  C  S  R  *                              225

CCGAAAGATTCAACCTCTGCTCCTGCTGGGGAAGCTCGGGCGCGAGTGTGAAACTGGTGT   +1080 t85

AAATATTGTGGCACACACAAGCTACTACAGTCCGTCTCGCCGTCCGGCTAACTAGCCTTG   +1140 t145

CTGCGGATCTGTCCATCTTCGGTCCGAACTGTCCGTTGCTGTTTTGGCTCGGTGCCTCAT   +1200 t205

CTTCTCCCAACCTAGTCAAGAATGAATCGTGAGAGAGGCTGAGAGAGATAAGATCGACTT   +1260 t265

CAGAAATCCAGGGTTGAAAGCAATAAAAAATTCCTGTGGGATGAATATCTCGTGATGC    +1320 polyA site

AACGACCCTCCTAGGAAACCTTGACGAAATTTGCTGACGGCAAATTCTTCAAAGACTCGT   +1380 t385

TAACCGGTCGCCCGTAGTGGTCCTGTTGCCCCAATCCGTTTGTGTTGAAATGACATTGCG   +1440 t445

CGTAACGCCGGACTCATATCAACTGCGTACCGAAAGCCAATCCCTCCCCAAACACGCCCT   +1500 t505
```

-continued

```
CTCTAATAAGCTCTCCCAAACAAGACCTCTTGAGACAGAAAATACGCCCAGATGCTGAGG    +1560 t565

ACTTGACAAGCCGGGGGGGGGGGGGGCTTGTCAAGTGCAAAAACTTGCCCATTTCATGC    +1620 t625

TGGTATCAAAAAAACAAAAAAAAAAAAAAACATTTCAAGTCGCGGATGCCCCATTTACAT    +1680 t685

TGCTTGCGTGCGCCAATAGAAACTTGCAACACGTCAGTGTCATCTTGCACGCCTTGG      +1737 t742
```

SEQ ID No. 14:
C1-EG5 "25 kD" Protein sequence

MHLSATTGFL ALPALALAQL SGSGQTTRYW DCCKPSCAWP GKGPSSPVQA CDKNDNPLND

GGSTRSGCDA GGSAYMCSSQ SPWAVSDELS YGWAAVKLAG SSESQWCCAC YELTFTSGPV

AGKKMIVQAT NTGGDLGDNH FDLAIPGGGV GIFNACTDQY GAPPNGWGDR YGGIHSKEEC

ESFPEALKPG CNWRFDWFQN ADNPSVTFQE VACPSELTSK SGCSR

SEQ ID No. 6:
C1-EG6 "43kD" (Family 6) was obtained by PCR based on
"43kD Endo" protein sequencing and family 6 cellulases
homology analysis.

```
-2508       GGATCCACACCTACCATACCGGATAGTATGCTACCCAAGTGACATAGG   -2461

GTTGGTAAAGTAATACGAGAACTCAGAGAGCACTGCCCATATGGCTCGCCAATGACCTCA   -2401

AGTGCCAGGTCAGCTTTGCGAGACAGACCTGAGCGCGTCGGATGTGTGACATGGAACGCG   -2341

CCGGATCGCCTTGTTGATTAATTATAGGGAAGTAGCGAGGAAGGTTTCAGCAATTGACGT   -2281

GAGCGTACATTAAAAGCTGTATGATTTCAGGAAGACGAGCCATGGACCAGGTTTCAAGGC   -2221

TGAATGGCTTGACGACTTAAGCACCGAACGAGGAATGAAAGAATGAAAAGTGGGGATCA   -2161 creA

TTCTGGCCCCTCCTCGTATGTCGAGTGTTAAAGAAGGCGGTTCTACGGAGGACCTAAAGA   -2101

GCTCCAATTTGCTCTGTTGAGCTTAAGCCACATATCTCAAGATGAATACATGTCAGGCAT   -2041

AGTCACCCTGATCTTGTTCATCAGTCCACACACTTTTCAGTTCAGCATGTTGATTCCTCA   -1981

TCCATATCACTTTCCATTACTATCTCTTTATGTCCTTGGTCAAGACTCCAAGGAACCGAT   -1921

AGGTGAGCATCGGTGAGGCTCCCTCAAGGTACCAAAGTAGCCATCATCACCGAGGTCTGG   -1861

GAATGGCGCCGTGCCCGATCTGAGTCCTCCAACTCCACGGTACGACGACAGCACGTCACA   -1801

TTGACGCACCACGGTTGAACAAGCAGAGAGGGACACGTCTTGCTACGCGAATCCTGGCAC   -1741

TGGATGGAGACGCGTGTGAGCAGGTTTCCGGAACCATGACGGCCTGGTCCGGCTTCTCGA   -1681

ACAAAGAAGTGGAACACAAAAAGAACCGAAACGGAAACGCAGGCACGGCATCGACGACCG   -1621

GATTGTCCCACGGGACCTCGGCCAGTCAAGCGTTGCCCTGGCCGTCAGCTCCCTGGCGA   -1561

CGGGGATTCAGCACATCTCACGTTATAGGCGACCTCATCCCCCTTCCGTCTTGTGCGGTC   -1501

GTTGCTCCGTGCCGAGTACCCAGGCGTGCCGGGGCCTTTAGCCGGGGCGGAATCAGAGTC   -1441 creA

AAGATGCGGCCGAATTGGACGGCAGACGAAGTTTCGTAGAGGGTCATGATCGGCACTGAC   -1381

GACACCCACCCCTGCGTGATCCCGTGGCCCTGGGCTGGGAATTGCCGGCTAATAATCTAC   -1321

GGCTTAATAGATATGCACTTTGCACGCGGTGCAGATAAATAAGCTGTGGTTTCAAACACT   -1261

GGCCTCCGTACTTTACCCACCAACTGCCGCTTAGCGCCGGGACCTGAGTCTTGGGAGTGC   -1201
```

-continued

```
GCGGAGCGGCAGCCACCTCGGGTTAGCGTACACACGACGGCTGCATGCGGGGATGCCGCG    -1141
``` creA

```
TGCATGGCTTCATAGTGTACGACAGACCGTCAAGTCCAAATCTGGGTGATGCTTGATGAG    -1081
``` creA

```
ATGACAGCGAGCCCCGTCGGCGGCACCCCGGCTATGCATCGCGAATTGACAACACTCTCA    -1021
GCTCTATTGCGACCCATCGGATAAAAGAAGAAGAAAAAAATGGACCTTGAGTACGGGCGT     -961
CAGAAACCAAAAAAAAACTCCGGAACCAAATATGTCGGGCATGGCCGGGGTGAACGACCG     -901
CTACTCCCCGTTCCCTTCTTCGCAAACAGAACGCTACAGAGGGTTTTCTGGTTTGTCAAA     -841
GAGTTCGGAGGTCCTCTGCTCCGCGAATGCGTGGTGAACCCACCAGCAGCCATTGTTCTT     -781
GCATGCGTGGCGGACCGTTAGCCGCTGATCGACATGGCGAGCTTCCCACCTCAGACCTGG     -721
``` creA

```
AGCAGACGGTTGCGAGGAGCAAGGGGCTGCCCTCCCCCTGACGGTCGGACCCCAATGACT     -661
TCCCCAAACGGGACATCGAGGGTCGTGCATGATGGTGGAAAGTAGTTGCAGTATGGGAA      -601
GTACCCCGGGTTGCCAGGAACCGTTGTTCGGCCCCCCACATTTTCTCTCTGCCATGTCAA     -541
CTGTGTGTCGTTCGAGAGTTCCTGGCTCCGGCCCCCCGTCCAATTCCCTAACGGGACCGC     -481
``` creA

```
GGGGCATCGCCTGTAACTAACTTCCAAATGAAGCCGGATATGAGGGAGGGAGATTGGATC     -421
TGGCAAGCCAGCCATTCGCTGCGATCGGCACTCGTCCGTCAGCCCCGCAGTCCATATCCC     -361
``` areA

```
CAAAGGCAACTGCTCGGCGCGGCTCAAGTCTTCTTCGGAACGTCCAGCCCGAAGGCGCGC     -301
GCCAGCACCGGCCCTATGTTCCTGATTGCGATCCTCGATCTCCAGAGACGGGTCACCTCG     -241
CCTCGAGGACGGTGCAGGGGCATCGGCTTCGCTTCCTAGAGCTCCGGGCTGTGTGTGGTC     -181
AAGGGGAGAAGGCGGCGGCGCCAAGGTGCGTCTCGGCGCACTCACCCATCGCCTTTACCC     -121
CCCTCCCCCCCAGTATATAAAAGATGGCCATCGTCTCCTCGTCTGCTTGGGAAGAAAGGA     -61
TCTCTCGACCATGCACCACAGCCTAGCTCTAACCCAGCTTGTCGTGTGTTGTTGCCCAGC     -1
``` transc.ini.

```
ATGAAGTTCGTGCAGTCCGCCACCCTGGCGTTCGCCGCCACGGCCCTCGCTGCGCCCTCG     +60
```

Putative Signal Seq

```
 M   K   F   V   Q   S   A   T   L   A   F   A   A   T   A   L   A   A   P   S      20
CGACGACTCCCCAGAAGCCCCGCCAGGCCTCGGCGGGCTGCGCGTCGGCCGTGACGCTC    +120
 R   T   T   P   Q   K   P   R   Q   A   S   A   G   C   A   S   A   V   T   L      40
GATGCCAGCACCAACGTGTTCCAGCAGTACACGCTGCACCCCAACAACTTCTACCGTGCC    +180
 D   A   S   T   N   V   F   Q   Q   Y   T   L   H   P   N   N   F   Y   R   A      60
GAGGTCGAGGCTGCCGCCGAGGCCATCTCCGACTCGGCGCTGGCCGAGAAGGCCCGCAAG    +240
 E   V   E   A   A   A   E   A   I   S   D   S   A   L   A   E   K   A   R   K      80
GTCGCCGACGTCGGTACCTTCCTGTGGCTCGACACCATCGAGAACATTGGCCGGCTGGAG    +300
 V   A   D   V   G   T   F   L   W   L   D   T   I   E   N   I   G   R   L   E     100
CCCGCGCTCGAGGACGTGCCCTGCGAGAACATCGTGGGTCTCGTCATCTACGACCTCCCG    +360
 P   A   L   E   D   V   P   C   E   N   I   V   G   L   V   I   Y   D   L   P     120
GGCCGTGACTGCGCGGCCAAGGCCTCCAACGGCGAGCTCAAGGTCGGCGAGCTCGACAGG    +420
 G   R   D   C   A   A   K   A   S   N   G   E   L   K   V   G   E   L   D   R     140
```

```
TACAAGACCGAGTACATCGACAgtgagttaacccttgtggccccttcttttcccccgag      +480
              Intron 1
 Y  K  T  E  Y  I  D                                              147 agagcgtctggttgagtggggttgtgagagagaaaatggggcgagcttaaagactgacgt     +540 gttggctcgcagAGATCGCCGAGATCCTCAAGGCCCACTCCAACACGGCCTTCGCCCTCG     +600
            K  I  A  E  I  L  K  A  H  S  N  T  A  F  A  L     163

TCATCGAGCCCGACTCGCTCCCCAACCTGGTCACCAATAGCGACCTGCAGACGTGCCAGC     +660
 V  I  E  P  D  S  L  P  N  L  V  T  N  S  D  L  Q  T  C  Q     183

AGAGCGCTTCCGGCTACCGCGAGGGTGTCGCCTATGCCCTCAAGCAGCTCAACCTCCCCA     +720
 Q  S  A  S  G  Y  R  E  G  V  A  Y  A  L  K  Q  L  N  L  P     203

ACGTGGTCATGTACATCGATGCCGGCCACGGTGGCTGGCTCGGCTGGGACGCCAACCTCA     +780
 N  V  V  M  Y  I  D  A  G  H  G  G  W  L  G  W  D  A  N  L     223

AGCCCGGCGCCCAGGAGCTCGCCAGCGTCTACAAGTCTGCTGGTTCGCCCTCGCAAGTCC     +840
 K  P  G  A  Q  E  L  A  S  V  Y  K  S  A  G  S  P  S  Q  V     243

GCGGTATCTCCACCAACGTGGCTGGTTGGAACGCCTGgtaagacactctatgtcccctc     +900
                                      Intron 2
 R  G  I  S  T  N  V  A  G  W  N  A  W                          256 gtcggtcaatggcgagcggaatggcgtgaaatgcatggtgctgacctttgatcttttccc    +960 cctcctatagGGACCAGGAGCCCGGTGAGTTCTCGGACGCCTCGGATGCCCAGTACAACA     +1020
           D  Q  E  P  G  E  F  S  D  A  S  D  A  Q  Y  N      272

AGTGCCAGAACGAGAAGATCTACATCAACACCTTTGGCGCTGAGCTCAAGTCTGCCGGCA     +1080
 K  C  Q  N  E  K  I  Y  I  N  T  F  G  A  E  L  K  S  A  G     292

TGCCCAACCACGCCATCATCGACACTGGCCGCAACGGTGTCACCGGTCTCCGCGACGAGT     +1140
 M  P  N  H  A  I  I  D  T  G  R  N  G  V  T  G  L  R  D  E     312

GGGGTGACTGGTGCAACGTCAACGGCGCCGGCTTCGGTGTGCGCCCCGACTGCCAACACTG     +1200
 W  G  D  W  C  N  V  N  G  A  G  F  G  V  R  P  T  A  N  T     332

GCGACGAGCTCGCCGACGCCTTCGTGTGGGTCAAGCCCGGTGGCGAGTCCGACGGCACCA     +1260
 G  D  E  L  A  D  A  F  V  W  V  K  P  G  G  E  S  D  G  T     352

GCGACTCGTCGGCGGCGCGCTACGACAGCTTCTGCGGCAAGCCCGACGCCTTCAAGCCCA     +1320
 S  D  S  S  A  A  R  Y  D  S  F  C  G  K  P  D  A  F  K  P     372

GCCCCGAGGCCGGTACCTGGAACCAGGCCTACTTCGAGATGCTCCTCAAGAACGCCAACC     +1380
 S  P  E  A  G  T  W  N  Q  A  Y  F  E  M  L  L  K  N  A  N     392

CGTCCTTCTAAGCTCCTCGACGGCTTCTTGCTGTCAGTCGCTCTGACGGTGGTGTGCTGG     +1440 t49

P  S  F  *                                                     395

TGGTGCCCCTGCTCCTGCTGCTGCTGCTCCGCGGGGAGGGGAGGCAACGAAAATGAAGTC     +1500 t109

CTGCTTCAAAACAAAACAGAAACAAGCGAGGCGCGGTGCAATGGTCGTGCGTTCGTCTTT     +1560 t169

TTTCATGTTCCCTTCTAGTGTAGTAGTTTGATAGTCGTACATAAGGGGTTTCAGAACCGT     +1620 t229

CTCTCTGTCTCGGTCTTTTTGCGAGTTGTTGCGACTCGTGATTATGGCCTTTGTTGCTCG     +1680 t289

TTGCGGCAGAGTAGAACCACAGCGTGTTGGGGTAGCAGCTTGCTCCGTAGGACGTAGGGA     +1740 t349

AACAACCTGAGACTCTGGAATTGCAGTCAGCCTGCGTCGCCCCTCTAGGAAACGAAGGGG     +1800 t409
```

-continued

```
AGAACCAGTAGTGGCTGCAGCTTACAAACGCGAGCATGGTGAACATCTCCGAGAAAAGGG    +1860 t469

AGGGATCC                                                        +1868 t477
    BamHI
```

SEQ ID No. 15:
C1-EG6 "43 kD" Protein sequence

```
MKFVQSATLA FAATALAAPS RTTPQKPRQA SAGCASAVTL DASTNVFQQY TLHPNNFYRA

EVEAAAEAIS DSALAEKARK VADVGTFLWL DTIENIGRLE PALEDVPCEN IVGLVIYDLP

GRDCAAAASN GELKVGELDR YKTEYIDKIA EILKAHSNTA FALVIEPDSL PNLVTNSDLQ

TCQQSASGYR EGVAYALKQL NLPNVVMYTD AGHGGWLGWD ANLKPGAQEL ASVYKSAGSP

SQVRGISTNV AGWNAWDQEP GEFSDASDAQ YNKCQNEKIY INTFGAELKS AGMPNHAIID

TGRNGVTGLR DEWGDWCNVN GAGFGVRPTA NTGDELADAF VWVKPGGESD GTSDSSAARY

DSFCGKPDAF KPSPEAGTWN QAYFEMLLKN ANPSF
```

SEQ ID No. 7 (DNA) and SEQ ID No. 16 (protein):
Chrysosporium xylanase F (partial)

```
TGACCTTCTCCTCCTTCTCCCGAACAATAATAGATAATTACGAGCCGGTTCGAGGCTGAC        1

ATTGCGCGATTCTAGCGAGCCGCAATCAATTCAACTTTGCCAACGCCGACGCGGTTGTC       61
              S   R   N   Q   F   N   F   A   N   A   D   A   V   V

AACTTTGCCCAGGCCAACGGCAAGCTCATCCGCGGCCACACCCTCCTCTGGCACTCTCAG     120
 N   F   A   Q   A   N   G   K   L   I   R   G   H   T   L   L   W   H   S   Q

CTGCCGCAGTGGGTGCAGAACATCAACGACCGCAACACCTTGACCCAGGTCATCGAGAAC     180
 L   P   Q   W   V   Q   N   I   N   D   R   N   T   L   T   Q   V   I   E   N

CACGTCACCACCCTTGTCACTCGCTACAAGGGCAAGATCCTCCACTGGGACGTCGTTAAC     240
 H   V   T   T   L   V   T   R   Y   K   G   K   I   L   H   W   D   V   V   N

GAGATCTTTGCCGAGGACGGCTCGCTCCGCGACAGCGTCTTCAGCCGCGTCCTCGGCGAG     300
 E   I   F   A   E   D   G   S   L   R   D   S   V   F   S   R   V   L   G   E

GACTTTGTCGGCATCGCCTTCCGCGCCGCCCGCGCCGCCGATCCCAACGCCAAGCTCTAC     360
 D   F   V   G   I   A   F   R   A   A   R   A   A   D   P   N   A   K   L   Y

ATCAACGACTACAGGTCGACA                                            420
 I   N   D   Y   R   S   T                                        —
```

SEQ ID No. 8 (DNA) and SEQ ID Nos. 17-18 (protein):
C1-EG3 (Family 12) gene tragment obtained by PCR based on
family 12 cellulases homology analysis.

```
GAATTCGGGGATTACGAGCTAATGATCTGgtcagttttttttttctttttt
         g   d   y   e   l   m   i   w tcttttcttcnctttctttttcttttcctttctcctgttttattttctta               100 tccattgcttcgccctctttccttaaccctgctgactctctcttcttgtc aatgatactgtaatagGCTGGCGAGATTCGGCGACGTCTACCCCATCGGC               200
                  L   A   R   F   G   D   V   Y   P   I   G TCGTCCCAGGGCCACGTCAACGTGGCCGCCAGGACTGGGAGCTGTGGAC
 S   S   Q   G   H   V   N   V   A   G   Q   D   W   E   L   W   T GGGCTTCAANGGNAACATGCGGGTCTACAGCTTCGTAGCGCCCANCCCC                299
 G   F   X   G   N   M   R   V   Y   S   F   V   A   P   X   P CGCAACAGNTTCAGCGCCAACGTCAAGGACTTCTTCAACTATCTCCAGTC
 r   n   x   f   s   a   n   v   k   d   f   f   n   y   l   q   s
```

```
                                                                      400
CAACCAGGGCTTCCCGGCCAGCAGCCAATACCTTCTCAAgtaaggagacga
 n  q  g  f  p  a  s  s  q  y  l  l  n ?

gatctcgaacagcataccatatatgcgtgcggtacaagtgcactaaccccc ttttttttcccgttcgcagtCTTCCAGTTCGGCACTG                                 487
```

SEQ ID No. 9 (DNA) and SEQ ID No. 19 (protein):
Chrysosporium cellobiohydrolase CBH1

```
        TTTNGGGCGCCGTCTTACTCCTACCTTGCACCGTGATCGGCCAGTCGCGCTGCGAGGGCG
  1     ?  G  A  V  L  L  L  P  C  T  V  I  G  Q  S  R  C  E  G

ACTCGTGCGGCGGTACCTACAGCACCGACCGCTATGCCGGCATCTGCGACCCCGACGGAT
 61     D  S  C  G  G  T  Y  S  T  D  R  Y  A  G  I  C  D  P  D  G

GCGACTTCAACTCGTACCGCCAGGGCAACAAGACCTTCTACGGCAAGGGCATGACGGTCG
121     C  D  F  N  S  Y  R  Q  G  N  K  T  F  Y  G  K  G  M  T  V

ACACGACCAAGAAGATCACGGTCGTCACCCAGTTCCTCAAGAACTCGGCCGGCGAGCTCT
181     D  T  T  K  K  I  T  V  V  T  Q  F  L  K  N  S  A  G  E  L

CCGAGATCAAGCGGTTCTACGTCCAGAACGGCAAGGTCATCCCCAACTCCGAGTCCACCA
241     S  E  I  K  R  F  Y  V  Q  N  G  K  V  I  P  N  S  E  S  T

TCCCCGGCGTCGAGGGCAACTCCATCACCCAGGACTGGTGCGACCGCCAGAAGGCCGCCT
301     I  P  G  V  E  G  N  S  I  T  Q  D  W  C  D  R  Q  K  A  A

TCGGCGACGTGACCGACTTCCAGGACAAGGGCGGCATGGTCCAGATGGGCAAGGCCCTCG
361     F  G  D  V  T  D  F  Q  D  K  G  G  M  V  Q  M  G  K  A  L

CGGGGCCCATGGTCCTCGTCATGTCCATATGGGACGACCACGCCAGTNAACA
421     A  G  P  M  V  L  V  M  S  I  W  D  D  H  A  S  ?
```

---

We claim:

1. A mutant Chrysosporium strain comprising a nucleic acid sequence encoding a polypeptide of interest, said nucleic acid sequence being operably linked to expression-regulating region selected from the group consisting of a promoter sequence associated with cellulase expression, xylanase expression, or gpdA expression; and optionally a secretion signal sequence, said mutant strain expressing said polypeptide of interest at a higher level than the corresponding non-mutant strain under the same conditions.

2. A mutant Chrysosporium strain according to claim 1, said mutant being obtained by recombinant methods comprising stable introduction of at least one heterologous nucleic acid sequence selected from heterologous polypeptide-encoding nucleic acid sequences, heterologous signal sequences and heterologous expression-regulating sequences.

3. A mutant Chrysosporium strain according to claim 2, wherein said mutant strain expresses said polypeptide of interest at a higher level than the corresponding non-mutant strain under the same conditions.

4. A mutant Chrysosporium strain according to claim 1, wherein said polypeptide of interest is a homologous polypeptide which is expressed at a higher level than in the corresponding non-mutant strain under the same conditions.

5. A mutant Chrysosporium strain according to claim 1, wherein said polypeptide of interest is selected from carbohydrate-degrading enzymes, proteases, lipases, esterases, other hydrolases, oxidoreductases and transferases.

6. A mutant Chrysosporium strain according to claim 1, wherein said polypeptide of interest is selected from fungal enzymes allowing production or overproduction of primary metabolites, organic acids, secondary metabolites, and antibiotics.

7. A mutant Chrysosporium strain according to claim 1, wherein said polypeptide of interest is inactivated at a pH below 6.

8. A mutant Chrysosporium strain according to claim 1, wherein said polypeptide of interest exhibits optimal activity and/or stability at a pH above 6, and/or has more than 70% of its activity and/or stability at a pH above 6.

9. A mutant Chrysosporium strain according to claim 1, comprising a heterologous signal sequence.

10. A mutant Chrysosporium strain according to claim 1, wherein said secretion signal sequence is a fungal signal sequence.

11. A mutant Chrysosporium strain according to claim 10, wherein the fungal signal sequence is a signal sequence of a cellulase, β-galactosidase, xylanase, pectinase, esterase, protease, amylase, polygalacturonase or hydrophobin.

12. A mutant Chrysosporium strain according to claim 1, further comprising a selectable marker.

13. A mutant Chrysosporium strain according to claim 12, wherein the selectable marker confers resistance to a drug or relieves a nutritional defect.

14. A mutant Chrysosporium strain according to claim 1, comprising a heterologous expression-regulating region.

15. A mutant Chrysosporium strain according to claim 1, comprising a fungal expression-regulating region.

16. A mutant Chrysosporium strain according to claim 15, wherein the expression-regulating region comprises is an inducible promoter.

17. A mutant Chrysosporium strain according to claim 15, wherein the expression-regulating region comprises a high expression promoter.

18. A mutant Chrysosporium strain according to claim 1, said mutant being obtained by mutagenesis steps, the steps including at least one step chosen from the group consisting of UV irradiation and chemical mutagenesis.

19. A mutant Chrysosporium strain according to claim 18, wherein the mutagenesis steps comprise a first UV irradiation step, a N-methyl-N'-nitro-N-nitrosoguanidine treatment step, and a second UV irradiation step.

20. A mutant Chrysosporium strain according to claim 1, wherein said mutant Chrysosporium strain is a mutant *Chrysosporium lucknowense* strain.

21. A mutant Chrysosporium strain according to claim 20, wherein said mutant is or is a mutant of a strain selected from the group consisting of *C. lucknowense* strain C1 (VKM F-3500 D), UV13-6 (VKM F-3632 D), NG7C-19 (VKM F-3633 D), and UV18-25 (VKM F-3631 D).

22. A mutant Chrysosporium strain according to claim 1, wherein, when *Trichoderma reesei* and said Chrysosporium strain are cultured under conditions optimal for each strain, when the Trichoderma culture attains a viscosity of 200–600 cP, said Chrysosporium strain exhibits a biomass of less than half that of the Trichoderma.

23. A mutant Chrysosporium strain according to claim 1, said strain producing at least the amount of cellulase in moles per liter as produced by any of the *Chrysosporium lucknowense* mutant strains C1 (VKM F-3500 D), UV13-6 (VKM F-3632 D), NG7C-19 (VKM F-3633 D), and UV18-25 (VKM F-3631 D).

24. A mutant Chrysosporium strain according to claim 1, said strain producing less protease than produced by the *Chrysosporium lucknowense* strain C1 (VKM F-3500 D).

25. A mutant Chrysosporium strain according to claim 24, wherein the strain produces less than half the amount of protease produced by the C1 strain.

* * * * *

UNITED STATES PATENT AND TRADEMARK OFFICE
CERTIFICATE OF CORRECTION

PATENT NO. : 6,573,086 B1  Page 1 of 1
DATED : June 3, 2003
INVENTOR(S) : Mark Aaron Emalfarb et al.

It is certified that error appears in the above-identified patent and that said Letters Patent is hereby corrected as shown below:

<u>Title page,</u>
Item [75], Inventor's name, delete "EMALFRAB", and insert therefor
-- EMALFARB --.

Signed and Sealed this

Twenty-third Day of September, 2003

JAMES E. ROGAN
*Director of the United States Patent and Trademark Office*